United States Patent
Sørensen et al.

(10) Patent No.: US 11,098,018 B2
(45) Date of Patent: Aug. 24, 2021

(54) POTASSIUM CHANNEL INHIBITORS

(71) Applicant: ACESION PHARMA ApS, Copenhagen (DK)

(72) Inventors: Ulrik Svane Sørensen, Copenhagen (DK); Antonio Mete, Leicestershire (GB)

(73) Assignee: ACESION PHARMA ApS, Copenhagen (DK)

( * ) Notice: Subject to any disclaimer, the term of this patent is extended or adjusted under 35 U.S.C. 154(b) by 0 days.

(21) Appl. No.: 16/638,590

(22) PCT Filed: Aug. 13, 2018

(86) PCT No.: PCT/EP2018/071911
§ 371 (c)(1),
(2) Date: Feb. 12, 2020

(87) PCT Pub. No.: WO2019/034603
PCT Pub. Date: Feb. 21, 2019

(65) Prior Publication Data
US 2020/0216398 A1    Jul. 9, 2020

(30) Foreign Application Priority Data
Aug. 14, 2017   (EP) .................... 17020353

(51) Int. Cl.
*C07D 235/30* (2006.01)

(52) U.S. Cl.
CPC ................. *C07D 235/30* (2013.01)

(58) Field of Classification Search
CPC ................................. C07D 235/30
See application file for complete search history.

(56) References Cited

FOREIGN PATENT DOCUMENTS

| WO | 2006/013210 A2 | 2/2006 |
|---|---|---|
| WO | 2008/113747 A1 | 9/2008 |
| WO | 2013/104577 A1 | 7/2013 |
| WO | 2017/144183 A1 | 8/2017 |

OTHER PUBLICATIONS

Chandgude, et al. Document No. 167:244963, retrieved from STN; entered in STN on Jun. 16, 2017.*
Floch, et al. Document No. 111:77911, retrieved from STN; entered in STN on Sep. 1989.*
Krasikovs, et al. Document No. 158:620995, retrieved from STN; entered in STN on Apr. 24, 2013.*
Sririam, et al. Document No. 167:151394, retrieved from STN; entered in STN on Mar. 27, 2017.*
International Search Report dated Sep. 6, 2018, in corresponding International application No. PCT/EP2018/071911; 5 pages.
Krasikovs et al., "Iodoacetic Acid is an Efficient Reagent for the Synthesis of Amino Acid Derived 2-Aminobenzimidazoles", Synthesis, vol. 45, 2013, pp. 683-693, 11 pages.
Chandgude et al., "Direct Amination of α-Hydroxy Amides", Asian Journal of Organic Chemistry Communication, vol. 6, 2017, pp. 981-983, 3 pages.
Sriram et al., "Microwave Assisted Synthesis of Trifluoro Substituted 2-Aminobenzimidazole Derivatives via Iodoacetic Acid Mediated One-pot Condensation: Trifluoro substituted 2-Aminobenzimidazole Derivatives", J. Heterocyclic Chem., vol. 54, No. 4, 2017, pp. 2440-2446, 7 pages.
Floch L et al., "2-Amino-Substituted Derivatives of Benzimidazoles From 2-Isothiocyanato Carboxylates", Collect. Czech. Chem. Commun., vol. 54, (1989), pp. 206-214, 9 pages.

* cited by examiner

*Primary Examiner* — Shawquia Jackson
(74) *Attorney, Agent, or Firm* — Maier & Maier, PLLC

(57) ABSTRACT

A compound of the general formula (I). The compounds of formula I are useful for treatment of a cardiac disease, disorder or condition in a mammal.

31 Claims, No Drawings

POTASSIUM CHANNEL INHIBITORS

FIELD

The present invention relates to novel compounds, the use of said compounds as medicament and for the manufacture of a medicament for the treatment of a cardiac disease, disorder or condition in mammals. The invention also relates to pharmaceutical compositions comprising said novel compounds.

BACKGROUND

The heart is a muscle, which pumps the blood in the circulation by contracting 1-3 times per second. The heartbeat is caused by simultaneous contraction of the individual cardiac muscle cells (cardiac myocytes). The synchronization of the cellular contraction is governed by the electrical cardiac impulse (the cardiac action potential), which is generated in the pacemaker cells of the sine node and spreads rapidly over the heart through a specific conduction system.

Disturbances in the generation of the impulse and the conduction of impulse may occur either as a consequence of a disease, a drug treatment, or electrolyte imbalances. Such disturbances in the impulse are called arrhythmia or dysrythmia and they may lead to unease, emboli, syncope or sudden death. In its simplest form, an arrhythmia covers everything different from a normal cardiac sinus rhythm. Disturbances can cover anything from simple palpitations to devastating ventricular fibrillation including bradycardia and tachycardia.

At a molecular level a group of proteins called ion channels underlie the electrical events in the heart since they are able to conduct electrical currents across the cell membrane. Different types of ion channels are thus instrumental in the generation and conduction of the cardiac action potential, in the regulation of the heart rate by the autonomic nervous system, and in the contractile process in the individual heart cells. The different types of ion channels are therefore evident targets for anti-arrhythmic cardiac drugs, and many anti-arrhythmic drugs on the market do exert their effect by interacting with ion channels.

Anti-arrhythmic drugs are usually divided into four main classes according to the so-called Singh Vaughan Williams classification: Class I compounds all inhibit the cardiac voltage-dependent sodium channel Some Class I compounds do have additional effects influencing the cardiac action potential being the basis for a further subdivision into three subclasses:

Class IA compounds are sodium channel inhibitors such as Quinidine, Procainamide or Disopyramid, which prolong the action potential;

Class IB compounds are sodium channel inhibitors such as Lidocaine, Mexiletine, Tocainide or Phenytoine, which shorten the action potential; and Class IC compounds are sodium channel inhibitors such as Flecainide, Moricizine or Propafenone, which do not change the action potential duration.

Class I compounds interact with the sodium channel during its open or inactivated state and are dissociated from the channels during its closed state (during diastole). The rate of dissociation determines whether they show a frequency-dependent channel inhibition. Some of the class I compounds also inhibit subtypes of potassium or calcium permeable channels in addition to their sodium channel inhibiting effect.

Class II compounds are β-adrenoceptor inhibitors and include drugs like Atenolol, Metoprolol, Timolol or Propranolol. β-adrenoceptor inhibitors can be selective for cardiac β1-receptors or have affinity for β1- as well as β2-receptors. Some of the compounds also have an intrinsic β-stimulating effect.

Class III compounds are potassium channel inhibitors such as Amiodarone, Dronedarone, Sotalol, Ibutilide and Dofetilide, which prolong the action potential.

Class IV compounds are inhibitors of L-type calcium channels such as Verapamil.

Small-conductance calcium-activated potassium (SK) channels belongs to the family of $Ca^{2+}$-activated $K^+$ channels. Three SK channel subtypes have been cloned: SK1, SK2 and SK3 (corresponding to KCNN1-3 using the genomic nomenclature). The activity of these channels is determined by the concentration of free intracellular calcium ($[Ca^{2+}]i$) via calmodulin that is constitutively bound to the channels. SK channels are tightly regulated by $[Ca^{2+}]i$ in the physiological range being closed at $[Ca^{2+}]i$ up to around 0.1 μM but fully activated at a $[Ca^{2+}]i$ of 1 μM. Being selective for potassium, open or active SK channels have a hyperpolarizing influence on the membrane potential of the cell. SK channels are widely expressed in the central nervous system (CNS) and in peripheral tissue, including the heart.

The hyperpolarizing action of active SK channels plays an important role in the control of firing pattern and excitability of excitable cells. SK channel inhibitors such as apamin and N-methyl bicuculline, have been demonstrated to increase excitability, whereas the SK channel opener 1-EBIO is able to reduce electrical activity. In non-excitable cells, where the amount of $Ca^{2+}$ influx via voltage-independent pathways is highly sensitive to the membrane potential, an activation of SK channels will increase the driving force, whereas an inhibitor of SK channels will have a depolarizing effect, and thus diminish the driving force for calcium.

An SK channel inhibitor is a pharmaceutical agent that impairs the conduction of potassium ions ($K^+$) through $Ca^{2+}$-activated small conductance $K^+$ channels. The impairment can be obtained by any reduction in current resulting from e.g. a direct inhibition of ion conduction to a prevention of $Ca^{2+}$ binding, that is an obligate request for channel activation, or a reduction in calcium sensitivity.

A review of SK channels and SK channel modulators may be found in Wulff H et al.: "Modulators of Small- and Intermediate-Conductance Calcium-Activated Potassium Channels and their Therapeutic Indications", Currrent Medicinal Chemistry 2007 14 1437-1457; and in Liegeois J-F et al.: "Modulation of small conductance calcium-activated potassium (SK) channels: a new challenge in medicinal chemistry", Current Medicinal Chemistry 2003 10 625-647.

Based on the important role of SK channels in linking $[Ca^{2+}]i$ and membrane potential, SK channels are interesting targets for developing novel therapeutic agents, and the potential of inhibitors of SK channels for use in anti-arrhythmic treatment has recently been established, see e.g. Nattel S; J. Physiol. 2009 587 1385-1386; Diness J G, Sørensen US, Nissen J D, Al-Shahib B, Jespersen T, Grunnet M, Hansen R S; Circ. Arrhythm. Electrophysiol. 2010 3 380-90; and Diness et al; Hypertension 2011 57 1129-1135.

WO 2006/013210 describes certain 2-amino benzimidazole derivatives and their use as modulators of small-conductance calcium-activated potassium channels.

SUMMARY

The compounds of the present invention are inhibitors or negative modulators of the small-conductance calcium activated potassium (SK) channel and have an IC50 value of below 1000 μM as demonstrated in the Automated patch clamping system described herein, and are considered potent drug candidates. Some of these compounds also have physicochemical properties suitable for a drug substance and important for making pharmaceutical formulations. Further, some of these compounds have pharmacokinetic properties making them suitable for using as pharmaceutical drugs.

In a broad aspect the present invention relates to a compound of formula (I)

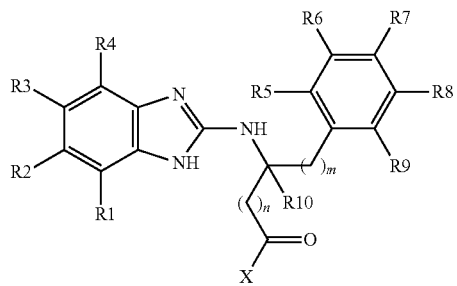

wherein
n is an integer selected from 0, 1, and 2;
m is an integer selected from 0, 1, and 2;
R1-R4 are independently a group selected from H, halogen, CN, $C_{1-6}$ alkyl, $C_{1-6}$ alkylene-OH, $C_{1-6}$ alkoxy, $OCF_3$, $C_{1-6}$ alkylene-O—$C_{1-6}$ alkyl, $C_{1-6}$ alkylene-S—$C_{1-6}$ alkyl, $C_{3-7}$ cycloalkyl, $NR^cC(=O)$—$C_{1-6}$ alkyl wherein $R^c$ is selected from H and $C_{1-6}$ alkyl, and $C_{1-6}$ alkylene-$NR^aR^b$, wherein $R^a$ and $R^b$ are independently a group selected from H, $C_{1-6}$ alkyl, $C_{1-6}$ alkylene-OH, $C_{1-6}$ alkylene-O—$C_{1-6}$ alkyl, $C(=O)$—$C_{1-6}$ alkyl, $C(=O)$—$C_{1-6}$ alkoxy, $C(=O)$—$C_{1-6}$ alkyl-CN, $C(=O)$—$C_{1-6}$ alkyl-OH, $C(=O)$—$C_{1-6}$ alkylene-S—$C_{1-6}$ alkyl, $C(=O)$—O—$C_{1-6}$ alkylene-O—$C_{1-6}$ alkyl, $C(=O)$—O—$C_{1-6}$ alkyl-CN, $C(=O)$—O—$C_{1-6}$ alkyl-OH, $C(=O)$—O—$C_{1-6}$ alkylene-S—$C_{1-6}$ alkyl, $C(=O)$—$NHC_{1-6}$ alkyl, $C(=O)$—$NHC_{1-6}$ alkylene-O—$C_{1-6}$ alkyl, $C(=O)$—$NHC_{1-6}$ alkylene-S—$C_{1-6}$ alkyl, $C(=O)$—$NHC_{1-6}$ alkyl-CN, $C(=O)$—$NHC_{1-6}$ alkyl-OH, $C(=O)$—N($C_{1-6}$ alkyl)$_2$, $SO_2$—$C_{1-6}$ alkyl, $SO_2$—$C_{1-6}$ alkylene-O—$C_{1-6}$ alkyl, $SO_2$—$C_{1-6}$ alkylene-S—$C_{1-6}$ alkyl, $SO_2$—$C_{1-6}$ alkyl-CN, $SO_2$—$C_{1-6}$ alkyl-OH, and $SO_2$—$C_{1-6}$alkyl-N($C_{1-6}$ alkyl)$_2$;
R5-R9 are independently a group selected from H, halogen, $CH_2F$, $CHF_2$, $CF_3$, CN, $C_{1-6}$ alkyl, $C_{1-6}$ alkylene-OH, OH, $C_{1-6}$ alkoxy, $C_{1-6}$ alkylene-O—$C_{1-6}$ alkyl, $C_{1-6}$ alkylene-S—$C_{1-6}$ alkyl, $C_{3-7}$cycloalkyl, $C(=O)$—O—$C_{1-6}$ alkyl, S—$C_{1-6}$ alkyl, $SCF_3$, $OCF_3$, $OCF_2H$, $OCFH_2$, $OC_{3-7}$ cycloalkyl, $SC_{3-7}$cycloalkyl;
R10 is a group selected from H and $C_{1-6}$ alkyl, $C_{1-6}$alkyl substituted with 1 to 3 Fluorine atoms, $C_{3-4}$cycloalkyl;
X is selected from
a) OR11, wherein R11 is a group selected from $C_{1-6}$ alkyl, $C_{1-6}$ alkylene-OH, $C_{1-6}$ alkylene-O—$C_{1-6}$ alkyl, $C_{1-6}$ alkylene-S—$C_{1-6}$ alkyl, $C_{1-6}$ alkylene-CN, and $C_{1-6}$ alkylene-$CF_3$; and
b) NR12R13, wherein R12 is a group selected from H, and $C_{1-6}$ alkyl; and R13 is a group selected from H, $C_{1-6}$ alkyl, OH, $C_{3-7}$ cycloalkyl, $C_{1-6}$ alkoxy, and $C_{2-6}$ alkenyl; or
a pharmaceutically acceptable salt thereof.
In one embodiment m is 0.
In another embodiment n is 1.
In a further embodiment n is 0.

In another embodiment n is 2.
In a still further embodiment m is 1.
In a further embodiment R1 is selected from H, $C_{1-6}$ alkyl, $C_{1-6}$ alkylene-OH, halogen, $C_{1-6}$ alkylene-O—$C_{1-6}$ alkyl, and $NR^cC(=O)$—$C_{1-6}$ alkyl wherein $R^c$ is selected from H and $C_{1-6}$ alkyl.
In a still further embodiment R1 is selected from H, $CH_3$, $CH_2OH$, $CH_2CH_2OH$, Cl, $CH_2$—O—$CH_3$, and NH—C($=O$)—$CH_3$.
In a further embodiment R2 is selected from H, $C_{1-6}$ alkyl, halogen, $OCF_3$ and CN.
In a still further embodiment R2 is selected from H, F, $OCF_3$, $CH_3$, and CN.
In a further embodiment R3 is selected from H, $C_{1-6}$ alkyl, $C_{1-6}$ alkylene-OH, halogen, $C_{1-6}$ alkylene-O—$C_{1-6}$ alkyl, and $NR^cC(=O)$—$C_{1-6}$ alkyl wherein $R^c$ is selected from H and $C_{1-6}$ alkyl.
In a still further embodiment R3 is selected from H, $CH_3$, $CH_2OH$, $CH_2CH_2OH$, Cl, $CH_2$—O—$CH_3$, and NH—C($=O$)—$CH_3$.
In a further embodiment R4 is selected from H, $C_{1-6}$ alkyl, $C_{1-6}$ alkylene-OH, halogen, $C_{1-6}$ alkylene-O—$C_{1-6}$ alkyl, and $NR^cC(=O)$—$C_{1-6}$ alkyl wherein $R^c$ is selected from H and $C_{1-6}$ alkyl.
In a still further embodiment R4 is selected from H, $CH_3$, $CH_2OH$, $CH_2CH_2OH$, Cl, $CH_2$—O—$CH_3$, and NH—C($=O$)—$CH_3$.
In a further embodiment R5 is selected from H.
In a still further embodiment R6 is selected from H, halogen, CN, $OCF_3$, $CF_3$, $C(=O)$—O—$C_{1-3}$ alkyl, S—$C_{1-3}$ alkyl, $SCF_3$ and $C_{1-6}$ alkyl.
In a further embodiment R6 is selected from H, Cl, F, $CF_3$, CN, $OCF_3$, $CH_3$, $C(=O)$—O—$CH_3$, S—$CH_3$, and $SCF_3$.
In a still further embodiment R7 is selected from H, halogen, and $C_{1-6}$ alkyl.
In a further embodiment R7 is selected from H, Cl, Br, F, and $CH_3$.
In a still further embodiment R8 is selected from H, halogen, $CF_3$, $C(=O)$—O—$C_{1-3}$ alkyl, S—$C_{1-3}$ alkyl, $OCF_3$ and $C_{1-6}$ alkyl.
In a further embodiment R8 is selected from H, Cl, F, $CF_3$, $CH_3$, $C(=O)$—O—$CH_3$, S—$CH_3$, and $OCF_3$.
In a still further embodiment R9 is selected from H.
In a further embodiment R10 is selected from H. In another embodiment R10 is selected from $C_{1-6}$ alkyl, such as $CH_3$.
In a still further embodiment X is selected from OR11. In an embodiment R11 is selected from $C_{1-6}$ alkyl. In a further embodiment R11 is selected from $CH_3$ and isopropyl.
In a further embodiment X is selected from NR12R13. In an embodiment R12 is selected from H and $C_{1-6}$ alkyl. In a further embodiment R12 is selected from H and $CH_3$. In an embodiment R13 is selected from H, $C_{1-6}$ alkyl, $C_{3-7}$ cycloalkyl, $C_{1-6}$ alkoxy, and $C_{2-6}$ alkenyl. In a further embodiment R13 is selected from H, $CH_3$, $CH_2CH_3$, isopropyl, isobutyl, cyclopropyl, cyclohexyl, $OCH_3$, and propenyl.
In a still further embodiment the compound of formula (I) is selected from:
2-[(1H-1,3-benzodiazol-2-yl)amino]-N,N-dimethyl-2-[3-(trifluoromethyl)phenyl]acetamide,
3-[(1H-1,3-benzodiazol-2-yl)amino]-N-methyl-3-[3 (trifluoromethyl)phenyl]propanamide,
3-[(1H-1,3-benzodiazol-2-yl)amino]-N-(prop-2-en-1-yl)-3-[3-(trifluoromethyl)phenyl]propanamide,
3-[(5-fluoro-4-methyl-1H-1,3-benzodiazol-2-yl)amino]-N-methyl-3-[3-(trifluoromethyl)phenyl]propanamide, N-methyl-3-[(4-methyl-1H-1,3-benzodiazol-2-yl)amino]-3-[3-(trifluoromethyl)phenyl]propanamide,
3-{[4-(2-hydroxyethyl)-1H-1,3-benzodiazol-2-yl]amino}-N-methyl-3-[3-(trifluoromethyl)phenyl]propanamide,
methyl 2-[(4-acetamido-1H-1,3-benzodiazol-2-yl)amino]-3-[3-(trifluoromethyl)phenyl]propanoate,
2-[(1H-1,3-benzodiazol-2-yl)amino]-N-methyl-3-[3-(trifluoromethyl)phenyl]propanamide,
3-[(1H-1,3-benzodiazol-2-yl)amino]-3-(4-fluoro-3,5-dimethylphenyl)-N-methylpropanamide,
3-[(1H-1,3-benzodiazol-2-yl)amino]-3-(4-chloro-3-methylphenyl)-N-methylpropanamide,
3-[(1H-1,3-benzodiazol-2-yl)amino]-N-methoxy-N-methyl-[3-(trifluoromethyl)phenyl]propanamide,
3-[(1H-1,3-benzodiazol-2-yl)amino]-N-methyl-3-[3-(methylsulfanyl)phenyl]propanamide,
3-[(1H-1,3-benzodiazol-2-yl)amino]-N-methyl-3-[3-(trifluoromethoxy)phenyl]propanamide,
3-[(5-fluoro-4-methyl-1H-1,3-benzodiazol-2-yl)amino]-3-[3-(trifluoromethyl)phenyl]propanamide,
2-[(1H-1,3-benzodiazol-2-yl)amino]-N-(2-methylpropyl)-2-[3-(trifluoromethyl)phenyl]acetamide,
2-[(1H-1,3-benzodiazol-2-yl)amino]-N-cyclopropyl-2-[3-(trifluoromethyl)phenyl]acetamide,
3-[(5-fluoro-1H-1,3-benzodiazol-2-yl)amino]-N-methyl-3-[3-(trifluoromethyl)phenyl]propanamide,
N-methyl-3-{[5-(trifluoromethoxy)-1H-1,3-benzodiazol-2-yl]amino}-3-[3-(trifluoromethyl)phenyl]propanamide,
3-{[4-(methoxymethyl)-1H-1,3-benzodiazol-2-yl]amino}-N-methyl-3-[3-(trifluoromethyl)phenyl]propanamide,
3-[(4-chloro-1H-1,3-benzodiazol-2-yl)amino]-N-methyl-[3-(trifluoromethyl)phenyl]propanamide,
3-{[4-(hydroxymethyl)-1H-1,3-benzodiazol-2-yl]amino}-N-methyl-3-{3-[trifluoromethyl)sulfanyl]phenyl}propanamide,
3-[(1H-1,3-benzodiazol-2-yl)amino]-3-(3,4-dichlorophenyl)-N-methylpropanamide,
3-[(1H-1,3-benzodiazol-2-yl)amino]-3-(3-cyanophenyl)-N-methylpropanamide,
methyl 3-{1-[(1H-1,3-benzodiazol-2-yl)amino]-2-(methylcarbamoyl)ethyl}benzoate, or
a pharmaceutically acceptable salt thereof.

In a further embodiment the compound of formula (I) is selected from:
4-[(1H-1,3-benzodiazol-2-yl)amino]-N-methyl-4-[3-(trifluoromethyl)phenyl]butanamide,
(−)-4-[(1H-1,3-benzodiazol-2-yl)amino]-N-methyl-4-[3-(trifluoromethyl)phenyl]butanamide,
(+)-4-[(1H-1,3-benzodiazol-2-yl)amino]-N-methyl-4-[3-(trifluoromethyl)phenyl]butanamide,
2-[(1H-1,3-benzodiazol-2-yl)amino]-N-methyl-2-[3-(trifluoromethyl)phenyl]propanamide,
(+)-2-[(1H-1,3-benzodiazol-2-yl)amino]-N-methyl-2-[3-(trifluoromethyl)phenyl]propanamide,
(−)-2-[(1H-1,3-benzodiazol-2-yl)amino]-N-methyl-2-[3-(trifluoromethyl)phenyl]propanamide, or
a pharmaceutically acceptable salt thereof.

In a further aspect the present invention relates to a compound of formula (I) as defined above for use as a medicine.

In a still further aspect the present invention relates to a pharmaceutical composition comprising a compound of formula (I) as defined above and optionally a pharmaceutically acceptable additive, such as carrier or excipient.

In a further aspect the present invention relates to a compound of formula (I) as defined above for use in a method for treating a cardiac disease, disorder or condition in a mammal, such as a human. In an embodiment a cardiac disease, disorder or condition is selected from the cardiac disease, disorder or condition wherein the disease, disorder or condition is associated with an abnormal rhythm of the heart or variant and exercise induced angina. In another embodiment the cardiac disease, disorder or condition is selected from the group consisting of cardiac arrhythmia, atrial arrhythmia, ventricular arrhythmia, atrial fibrillation, ventricular fibrillation, tachyarrhythmia, atrial tachyarrhythmia, ventricular tachyarrhythmia, bradyarrhythmias, and an abnormal rhythm arising after cardiac surgery or a cardiac ablation procedure.

In a further aspect the present invention relates to a method for treatment of a cardiac disease, disorder or condition in a mammal, such as a human, wherein a therapeutically effective amount of at least one compound of formula (I) as defined above is administered to a mammal in need of said treatment. In an embodiment the cardiac disease, disorder or condition in a mammal is selected from the group consisting of cardiac arrhythmia, atrial arrhythmia, ventricular arrhythmia, atrial fibrillation, ventricular fibrillation, tachyarrhythmia, atrial tachyarrhythmia, ventricular tachyarrhythmia, bradyarrhythmias, and an abnormal rhythm arising after cardiac surgery or a cardiac ablation procedure, In a still further aspect the present invention relates to a process of preparing a compound of formula I or a pharmaceutically acceptable salt or solvate thereof comprising the steps:

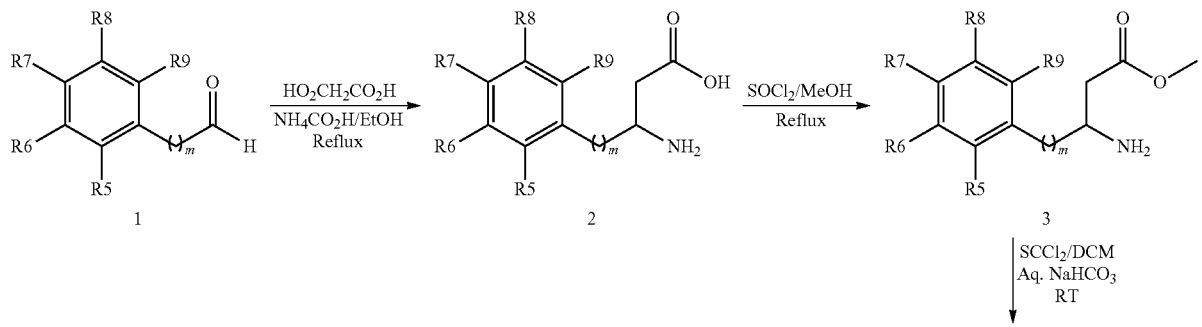

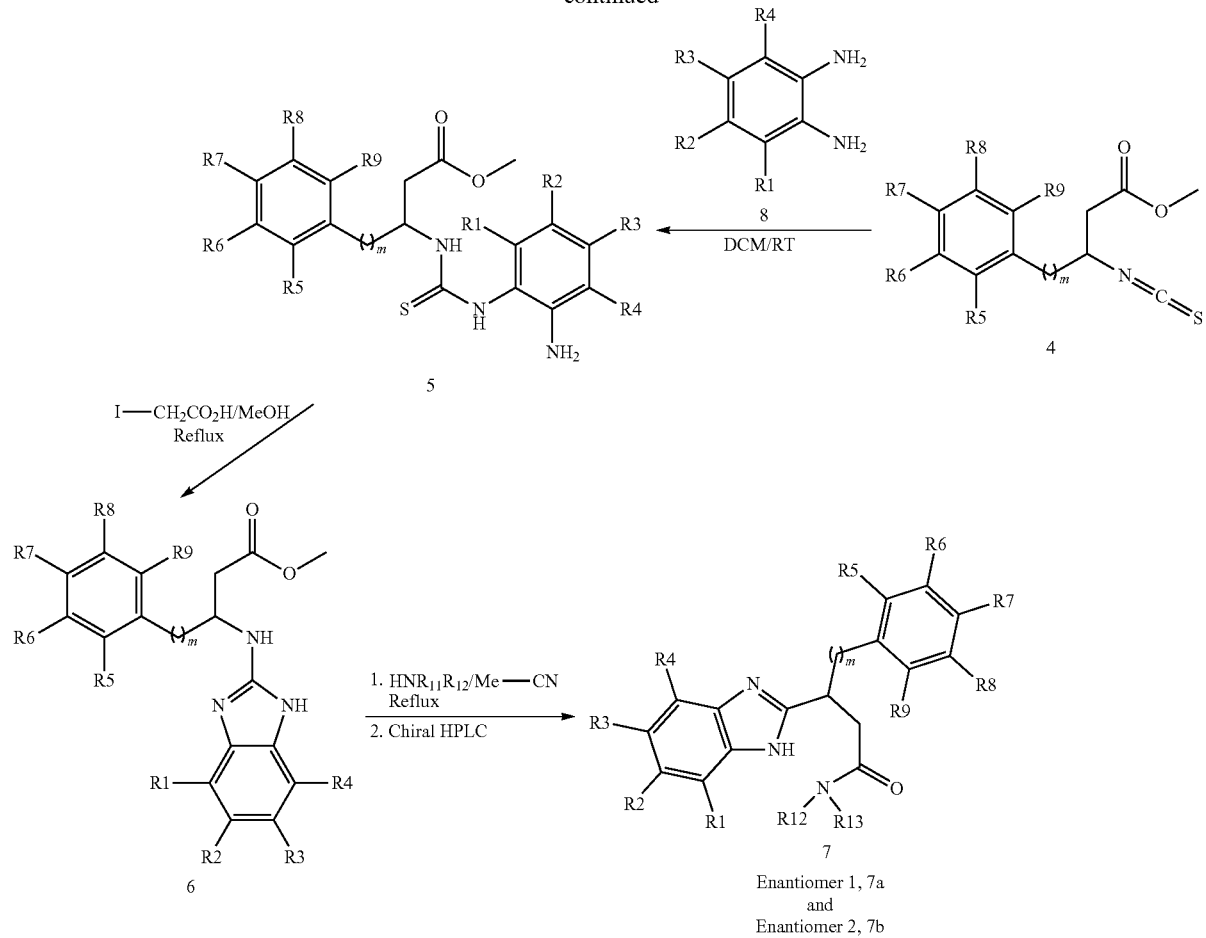

Enantiomer 1, 7a
and
Enantiomer 2, 7b

DETAILED DESCRIPTION

In a broad aspect the present invention relates to a compound of formula (I)

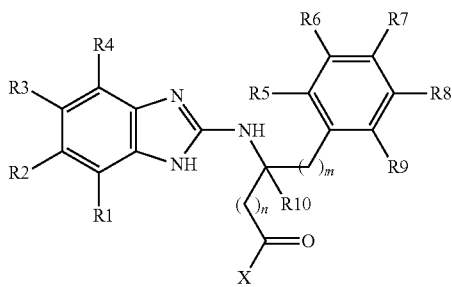

wherein
n is an integer selected from 0, 1, and 2;
m is an integer selected from 0, 1, and 2;
R1R4 are independently a group selected from H, halogen, CN, $C_{1-6}$ alkyl, $C_{1-6}$ alkylene-OH, $C_{1-6}$ alkoxy, $OCF_3$, $C_{1-6}$ alkylene-O—$C_{1-6}$ alkyl, $C_{1-6}$ alkylene-S—$C_{1-6}$ alkyl, $C_{3-7}$ cycloalkyl, $NR^cC(=O)$—$C_{1-6}$ alkyl wherein $R^c$ is selected from H and $C_{1-6}$ alkyl, and $C_{1-6}$ alkylene-$NR^aR^b$, wherein $R^a$ and $R^b$ are independently selected from H, $C_{1-6}$ alkyl, $C_{1-6}$ alkylene-OH, $C_{1-6}$ alkylene-O—$C_{1-6}$ alkyl, $C(=O)$—$C_{1-6}$ alkyl, $C(=O)$—$C_{1-6}$ alkoxy, $C(=O)$—$C_{1-6}$ alkyl-CN, $C(=O)$—$C_{1-6}$ alkyl-OH, $C(=O)$—$C_{1-6}$ alkylene-S—$C_{1-6}$ alkyl, $C(=O)$—O—$C_{1-6}$ alkylene-O—$C_{1-6}$ alkyl, $C(=O)$—O—$C_{1-6}$ alkyl-CN, $C(=O)$—O—$C_{1-6}$ alkyl-OH, $C(=O)$—O—$C_{1-6}$ alkylene-S—$C_{1-6}$ alkyl, $C(=O)$—$NHC_{1-6}$ alkyl, $C(=O)$—$NHC_{1-6}$ alkylene-O—$C_{1-6}$ alkyl, $C(=O)$—$NHC_{1-6}$ alkylene-S—$C_{1-6}$ alkyl, $C(=O)$—$NHC_{1-6}$ alkyl-CN, $C(=O)$—$NHC_{1-6}$ alkyl-OH, $C(=O)$—N$(C_{1-6}$alkyl$)_2$, $SO_2$—$C_{1-6}$ alkyl, $SO_2$—$C_{1-6}$ alkylene-O—$C_{1-6}$ alkyl, $SO_2$—$C_{1-6}$ alkylene-S—$C_{1-6}$ alkyl, $SO_2$—$C_{1-6}$ alkyl-CN, $SO_2$—$C_{1-6}$ alkyl-OH, and $SO_2$—$C_{1-6}$ alkyl-N$(C_{1-6}$ alkyl$)_2$;
R5-R9 are independently a group selected from H, halogen, $CH_2F$, $CHF_2$, $CF_3$, CN, $C_{1-6}$ alkyl, $C_{1-6}$ alkylene-OH, OH, $C_{1-6}$ alkoxy, $C_{1-6}$ alkylene-O—$C_{1-6}$ alkyl, $C_{1-6}$ alkylene-S—$C_{1-6}$ alkyl, $C_{3-7}$cycloalkyl, $C(=O)$—O—$C_{1-6}$ alkyl, S—$C_{1-6}$ alkyl, $SCF_3$, $OCF_3$, $OCF_2H$, $OCFH_2$, $OC_{3-7}$ cycloalkyl, $SC_{3-7}$cycloalkyl;
R10 is a group selected from H and $C_{1-6}$ alkyl, $C_{1-6}$alkyl substituted with 1 to 3 Fluorine atoms, $C_{3-4}$cycloalkyl;
X is selected from
a) OR11, wherein R11 is a group selected from $C_{1-6}$ alkyl, $C_{1-6}$ alkylene-OH, $C_{1-6}$ alkylene-O—$C_{1-6}$ alkyl, $C_{1-6}$ alkylene-S—$C_{1-6}$ alkyl, $C_{1-6}$ alkylene-CN, and $C_{1-6}$ alkylene-$CF_3$; and
b) NR12R13, wherein R12 is a group selected from H, and $C_{1-6}$ alkyl; and R13 is a group selected from H, $C_{1-6}$ alkyl, OH, $C_{3-7}$ cycloalkyl, $C_{1-6}$ alkoxy, and $C_{2-6}$ alkenyl; or
a pharmaceutically acceptable salt thereof.

In one embodiment n and m are 0. In another embodiment m is 0 and n is 1.

In a still further embodiment n is 0 and m is 1.

In a further embodiment n is 2 and m is 0. In a further embodiment R1 is selected from H.

In a further embodiment R1 is selected from $C_{1-6}$ alkyl, such as methyl.

In a still further embodiment R1 is selected from H, $CH_3$, $CH_2OH$, $CH_2CH_2OH$, Cl, $CH_2$—O—$CH_3$, and NH—C(=O)—$CH_3$.

In a further embodiment R1 is selected from $C_{1-6}$ alkylene-OH, such as $CH_2OH$ and $CH_2CH_2OH$.

In a still further embodiment R1 is selected from $NR^cC(=O)$—$C_{1-6}$ alkyl wherein $R^c$ is selected from H and $C_{1-6}$ alkyl, such as NH—C(=O)—$CH_3$.

In a further embodiment R1 is selected from $C_{1-6}$ alkylene-O—$C_{1-6}$ alkyl, such as $CH_2$—O—$CH_3$.

In a further embodiment R1 is selected from halogen, such as Cl.

In a further embodiment R2 is selected from H.

In a further embodiment R2 is selected from H, $C_{1-6}$ alkyl, halogen, $OCF_3$ and CN.

In a still further embodiment R2 is selected from H, F, $OCF_3$, $CH_3$, and CN.

In a further embodiment R2 is selected from halogen, such as F.

In a still further embodiment R2 is selected from $OCF_3$.

In a further embodiment R3 is selected from H.

In a further embodiment R3 is selected from H, $C_{1-6}$ alkyl, $C_{1-6}$ alkylene-OH, halogen, $C_{1-6}$ alkylene-O—$C_{1-6}$ alkyl, and $NR^cC(=O)$—$C_{1-6}$ alkyl wherein $R^c$ is selected from H and $C_{1-6}$ alkyl.

In a still further embodiment R3 is selected from H, $CH_3$, $CH_2OH$, $CH_2CH_2OH$, Cl, $CH_2$—O—$CH_3$, and NH—C(=O)—$CH_3$.

In a further embodiment R4 is selected from H.

In a further embodiment R4 is selected from H, $C_{1-6}$ alkyl, $C_{1-6}$ alkylene-OH, halogen, $C_{1-6}$ alkylene-O—$C_{1-6}$ alkyl, and $NR^cC(=O)$—$C_{1-6}$ alkyl wherein $R^c$ is selected from H and $C_{1-6}$ alkyl.

In a still further embodiment R4 is selected from H, $CH_3$, $CH_2OH$, $CH_2CH_2OH$, Cl, $CH_2$—O—$CH_3$, and NH—C(=O)—$CH_3$.

It is to be understood that further embodiments concern any combination of R1-R4 as described above, for instance in an embodiment R1-R4 are all H, or in another embodiment three of R1-R4 are H and one is selected from a group as defined above for any one of R1-R4 except H. For instance, R2-R4 are all H and R1 is $C_{1-6}$ alkylene-OH. In a further embodiment R2, R3, and R4 are all H and R1 is a group selected from $NR^cC(=O)$—$C_{1-6}$alkyl wherein $R^c$ is selected from H and $C_{1-6}$ alkyl, such as NH—C(=O)—$CH_3$. In a further embodiment R2, R3, and R4 are all H and R1 is a group selected from $C_{1-6}$ alkylene-O—$C_{1-6}$ alkyl, such as $CH_2$—O—$CH_3$. In a further embodiment R1, R3, and R4 are all H and R2 is a group selected from $OCF_3$.

In a further embodiment R5 is selected from H.

In a still further embodiment R6 is selected from H, halogen, CN, $OCF_3$, $CF_3$, C(=O)—O—$C_{1-3}$ alkyl, S—$C_{1-3}$ alkyl, $SCF_3$ and $C_{1-6}$ alkyl.

In a further embodiment R6 is selected from H, Cl, F, $CF_3$, CN, $OCF_3$, $CH_3$, C(=O)—O—$CH_3$, S—$CH_3$, and $SCF_3$.

In a still further embodiment R6 is selected from $C_{1-6}$ alkyl, halogen, CN, $SCF_3$, $OCF_3$, C(=O)—O—$CH_3$, and $CF_3$, such as methyl, Cl, CN, $SCF_3$, $OCF_3$, C(=O)—O—$CH_3$, and $CF_3$.

In a further embodiment R7 is selected from H.

In a still further embodiment R7 is selected from H, and halogen.

In a further embodiment R7 is selected from H, Cl, and F.

In a further embodiment R8 is selected from H.

In a still further embodiment R8 is selected from H, halogen, $CF_3$, C(=O)—O—$C_{1-3}$ alkyl, S—$C_{1-3}$ alkyl, $OCF_3$ and $C_{1-6}$ alkyl.

In a further embodiment R8 is selected from H, Cl, F, $CF_3$, $CH_3$, C(=O)—O—$CH_3$, S—$CH_3$, and $OCF_3$.

In a still further embodiment R9 is selected from H.

In a further embodiment R10 is selected from H and $C_{1-6}$ alkyl.

In a still further embodiment R10 is selected from H.

In a further embodiment R10 is selected from $CH_3$.

In a still further embodiment X is selected from OR11. In an embodiment R11 is selected from $C_{1-6}$ alkyl. In a further embodiment R11 is selected from $CH_3$.

In a further embodiment X is selected from NR12R13. In an embodiment R12 is selected from H and $C_{1-6}$ alkyl. In a further embodiment R12 is selected from H. In a further embodiment R12 is selected from H and $C_{1-6}$ alkyl. In a further embodiment R12 is selected from $CH_3$. In an embodiment R13 is selected from H, $C_{1-6}$ alkyl, $C_{3-7}$ cycloalkyl, $C_{1-6}$ alkoxy, and $C_{2-6}$ alkenyl. In a further embodiment R13 is selected from H. In a further embodiment R13 is selected from $CH_3$. In a further embodiment R13 is selected from propenyl. In a further embodiment R13 is selected from $OCH_3$. In a further embodiment R13 is selected from isobutyl. In a further embodiment R13 is selected from cyclopropyl.

It is to be understood that further embodiments concern any combination of R5-R9 as described above, for instance four of R5-R9 are H and one is selected from a group as defined above for any one of R5-R9 except H. For instance, R5, R7-R9 are all H and R6 is a group selected from halogen, $CF_3$, $OCF_3$, $SCH_3$, $SCF_3$, Cl, CN, C(=O)—O—$CH_3$, and $C_{1-6}$ alkyl. In a further embodiment R5, R7-R9 are all H and R6 is a group selected from, $CF_3$, $OCF_3$, $SCH_3$, $SCF_3$, Cl, CN, C(=O)—O—$CH_3$, and $CH_3$.

Cardiac Diseases

In the context of this invention a cardiac disease, disorder or condition is any cardiac disease, disorder or condition, including, but not limited to, an abnormal rhythm of the heart or variant and exercise induced angina.

In a more specific embodiment the cardiac disease, disorder or condition is any disease, disorder or condition associated with an abnormal rhythm of the heart or variant and exercise induced angina.

In a more specific embodiment the cardiac disease, disorder or condition is any disease, disorder or condition associated with an abnormal rhythm of the heart.

In a more specific embodiment the cardiac disease, disorder or condition associated with an abnormal rhythm of the heart is selected from cardiac arrhythmia, atrial arrhythmia, ventricular arrhythmia, atrial fibrillation, ventricular fibrillation, tachyarrhythmia, atrial tachyarrhythmia, ventricular tachyarrhythmia, and bradyarrhythmias.

In another embodiment a cardiac disease, disorder or condition of the invention is an abnormal rhythm caused by myocardial ischaemia, myocardial infarction, cardiac hypertrophy, or cardiomyopathy.

In another embodiment a cardiac disease, disorder or condition of the invention is an abnormal rhythm arising after cardiac surgery or a cardiac ablation procedure.

In a further specific embodiment, the cardiac disease, disorder or condition associated with an abnormal rhythm of the heart is a cardiac arrhythmia caused by a genetic disease.

In a still further preferred embodiment the cardiac disease, disorder or condition associated with an abnormal rhythm of the heart is cardiac arrhythmia.

In a preferred embodiment the cardiac disease, disorder or condition associated with an abnormal rhythm of the heart is atrial fibrillation.

In a particular embodiment the compound of formula (I) of the present invention is useful for treatment of atrial fibrillation by acute cardioversion to normal sinus rhythm.

In another particular embodiment the compound of formula (I) of the present invention is useful for treatment of atrial fibrillation by maintaining normal sinus rhythm and avoiding or reducing the occurrence of new episodes of atrial fibrillation.

Pharmacological Treatment of Atrial Fibrillation

In the context of this invention, and as understood by a person skilled in the art, treatment of atrial fibrillation is acute cardioversion or maintenance of sinus rhythm or both. Acute conversion is defined as application of compound that has the ability to convert atrial fibrillation to a normal cardiac sinus rhythm. Normal sinus rhythm is defined as regular stable heart beating at frequencies between 40 and 100 beats at rest in adults with normal regular p-wave on a standard 12-lead electrocardiogram. Maintenance of sinus rhythm is defined as the ability for a compound to preserve a normal stable sinus rhythm over time with no relapse to atrial fibrillation or the ability of a compound to significantly reduced the incidence of relapse from atrial fibrillation to normal sinus rhythm compared to non-treated controls.

Description of General Process

Scheme 1 summarises one of the synthetic approaches that can be used to prepare compounds of general formula (I).

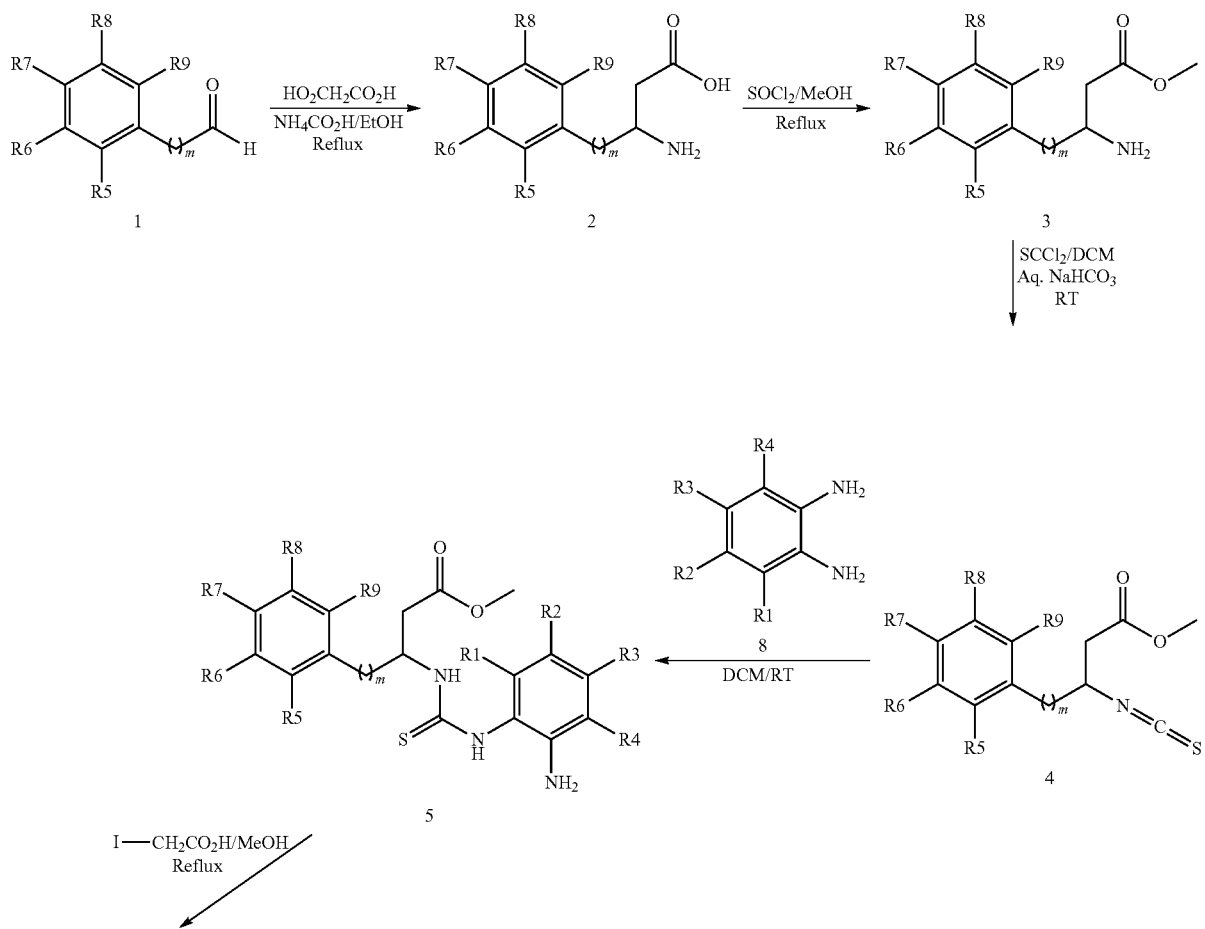

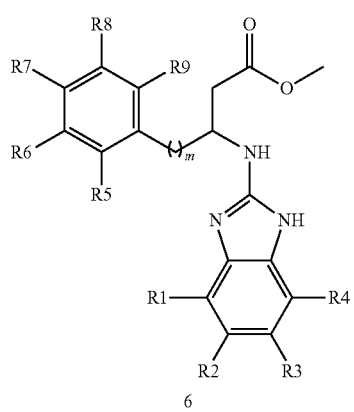

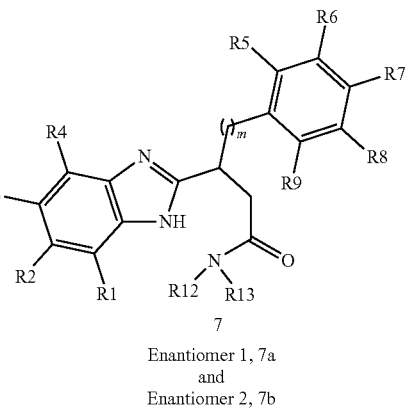

6

Enantiomer 1, 7a
and
Enantiomer 2, 7b

A large number of aldehydes (1) are commercially available or can be readily prepared by many routes described in the literature. The aldehydes (1) can be converted to the β-amino acids (2) by a wide range of methods, such as reaction of (2) with malonic acid derivatives under the influence of ammonium salts (e g ammonium formate) followed by subsequent decarboxylation upon heating. In addition, a large number of β-amino acids (2) and derivatives (such as their esters and amides) are also available from commercial sources. The β-amino acids (2) can be converted to their ester derivatives (3) by reaction with an alcohol (e.g. methanol, ethanol) under the influence of a strong acid (e.g. hydrochloric acid, sulphuric acid) or by first activation to the acid chloride with reagents, such a thionyl chloride, and then reaction with an alcohol. There are many other well-established methods for converting acids to esters described in the literature. The β-amino esters (3) can be converted to the isothiocyanate derivatives (4) by reaction with thiophosgene in a suitable solvent (e.g. dichloromethane) under the influence of a base (e.g. sodium hydrogen carbonate). The isothiocyanates (4) can react with a wide range of benzene-1,2-diamine derivatives (8) in a suitable solvent (e.g. dichloromethane) to afford the thiourea products (5). A wide range of benzene-1,2-diamine derivatives (8) are available commercially or can be readily prepared by well-established methods described in the literature (e.g. by nitration and subsequent reduction of commercial substituted benzene starting materials). The thiourea derivatives (5) can be converted to 2-aminobenzimidazole derivatives (6) by a ring forming reaction that occurs under the influence of iodoacetic acid and heating in a suitable solvent (such as methanol or acetonitrile). The cyclisation of (5) to afford (6) can also occur under the influence of mercury salts (e.g. mercuric oxide) with heating in a suitable solvent (e.g. acetonitrile). The 2-aminobenzimidazole ester derivatives (6) can react with a wide range of commercial amines to afford the amide derivatives (7). This reaction can be performed by subjecting a mixture of (6) and the amine in a suitable solvent (e.g. acetonitrile) to heating (up to reflux) or to irradiation with microwaves (with heating). The 2-aminobenzimidazole derivatives (7) can be a racemic mixture, which can be separated into the two enantiomers (7a) and (7b) by a range of methods, including chromatography using a chiral stationary phase. This can be normal-phase or reverse phase chromatography, which uses suitable solvent mixtures as eluent (e.g. chloroform, dichloromethane, ethanol, ethyl acetate, methanol, ethanol) sometimes with additives (e g ammonia, triethylamine, trifluoroacetic acid, acetic acid).

The process described above is applicable to prepare compounds of general formula (1) in which m=0, 1 or 2 by starting with the appropriate starting aldehyde (1). A large number of aldehydes (1) (m=0, 1, 2) are available commercially or can be readily prepared by many well-established methods described in the literature.

Compounds of general formula (I) in which n=0 can also be made by the general process described above, by starting with an α-amino acid (2) (n=0). A large number of α-amino acids are available commercially or can be readily prepared by many well-established methods described in the literature.

The process is suitable for a wide range of derivatives bearing a variety of R1 to R9 groups. In some cases the R1 to R9 groups may need to carry a chemical protecting group (e.g. when R1 to R9 bear substituents such as: —OH, —NH$_2$, NHR, —SH, —CO$_2$H etc). The protecting groups can be removed by a suitable de-protection step.

The skilled person will understand that it may be necessary to adjust or change the order of steps in the processes described above, and such change of order is encompassed by the aspects of the process as described above in the reaction schemes and accompanying description of the process steps.

Furthermore, the skilled person will understand that the processes described above and hereinafter the functional groups of intermediate compounds may need to be protected by protecting group.

Functional groups that it is desirable to protect include hydroxy, amino and carboxylic acid. Suitable protecting groups for hydroxy include optionally substituted and/or unsaturated alkyl groups (e.g. methyl, allyl, benzyl or tert-butyl), trialkyl silyl or diarylalkylsilyl groups (e.g,. t-butyldimethylsilyl, t-butyldiphenylsilyl or trimethylsilyl), AcO(acetoxy), TBS(t-butyldimethylsilyl), TMS(trimethylsilyl), PMB (p-methoxybenzyl), and tetrahydropyranyl. Suitable proteting groups for carboxylic acid include (C1-C6)-alkyl or benzyl esters. Suitable protecting groups for amino include t-butyloxycarbonyl, benzyloxycarbonyl, 2-(trimethylsilyl)-ethoxy-methyl or 2-trimethylsilylethoxycarbonyl (Teoc). Suitable protecting groups for S include 5-C(═N)NH$_2$, TIPS.

The protection and deprotection of functional groups may take place before or after any reaction in the above mentioned processes.

Furthermore the skilled person will appreciate that, in order to obtain compounds of the invention in an alternative, and on some occasions, more convenient, manner, the individual process steps mentioned hereinbefore may be performed in different order, and/or the individual reactions may be performed at a different stage in the overall route (i.e. substituents may be added to and/or chemical transformations performed upon, different intermediates to those mentioned hereinbefore in conjunction with a particular reaction). This may negate, or render necessary, the need for protecting groups.

The compound of formula (I) have at least one asymmetric center, and may have further asymmetric centres and it is intended that any optical isomers (i.e. enantiomers or diastereomers), in the form of separated, pure or partially purified optical isomers and any mixtures thereof including racemic mixtures, i.e. a mixture of stereoisomeres, are included within the scope of the invention. In particular, the carbon atom of formula (I) wherein the 4 valence bonds are linked to R10, NH, $(C)_n$, and $(C)_m$ and is an asymmetric centre giving rise to two optical isomers, an R form and an S form. In one embodiment, the compounds of the present invention have the S form. In another embodiment, the compounds of the present invention have the R form. In a further embodiment, the compounds of the present invention are a racemic mixture.

In this context is understood that when specifying the enantiomeric form, then the compound is in enantiomeric excess, e.g. essentially in a pure, mono-enantiomeric form. Accordingly, one embodiment of the invention relates to a compound of the invention having an enantiomeric excess of at least 60%, at least 70%, at least 80%, at least 85%, at least 90%, at least 96%, preferably at least 98%.

Racemic forms can be resolved into the optical antipodes by known methods, for example by separation of diastereomeric salts thereof with an optically active acid, and liberating the optically active amine compound by treatment with a base. Another method for resolving racemates into the optical antipodes is based upon chromatography of an optically active matrix. The compounds of the present invention may also be resolved by the formation of diastereomeric derivatives. Additional methods for the resolution of optical isomers, known to those skilled in the art, may be used. Such methods include those discussed by J. Jaques, A. Collet and S. Wilen in "Enantiomers, Racemates, and Resolutions", John Wiley and Sons, New York (1981). Optically active compounds can also be prepared from optically active starting materials.

Furthermore, when a double bond or a fully or partially saturated ring system is present in the molecule geometric isomers may be formed. It is intended that any geometric isomers, as separated, pure or partially purified geometric isomers or mixtures thereof are included within the scope of the invention. Likewise, molecules having a bond with restricted rotation may form geometric isomers. These are also intended to be included within the scope of the present invention.

Furthermore, some of the compounds of the present invention may exist in different tautomeric forms and it is intended that any tautomeric forms that the compounds are able to form are included within the scope of the present invention.

In a still further embodiment the compound I is on free form. In one embodiment the free form is an anhydrate. In another embodiment the free form is a solvate, such as a hydrate.

In a further embodiment the compound is a crystalline form. The skilled person may carry out tests in order to find polymorphs, and such polymorphs are intended to be encompassed by the term "crystalline form" as used herein.

When the compounds and pharmaceutical compositions herein disclosed are used for the above treatment, a therapeutically effective amount of at least one compound is administered to a mammal in need of said treatment.

The term "free form" as used herein means a compound of formula (I) which is a free base or free acid, as the case may be, and which is not in any salt form.

The term "$C_{1-x}$ alkyl" as used herein means an alkyl group containing 1 to x carbon atoms, e.g. $C_{1-3}$, $C_{1-4}$, $C_{1-5}$ or $C_{1-6}$, such as methyl, ethyl, propyl, butyl, pentyl or hexyl, and also includes branched $C_{3-6}$ alkyl, such as isopropyl, isobutyl, tert-butyl, isopentyl, 3-methylbutyl, 2,2-dimethylpropyl, n-hexyl, 2-methylpentyl, 2,2-dimethylbutyl, 2,3-dimethylbutyl. When $C_{1-x}$ alkyl, such as $C_{1-6}$alkyl, is substituted with a group, such as halogen, such as a F, it means that such F, e.g. 3 F are attached to one carbon ($CF_3$) or two carbons ($CF_2$—CF) or even three carbons (CF—CF—CF).

The term "$C_{1-x}$ alkylene" as used herein means an alkylene group containing 1 to x carbon atoms, e.g. $C_{1-3}$, $C_{1-4}$, $C_{1-5}$ or $C_{1-6}$, such as methylene, ethylene, propylene, butylene, pentylene or hexylene, and also includes branched $C_{3-6}$ alkylene, such as isopropylene, isobutylene, tert-butylene, isopentylene, 3-methylbutylene, 2,2-dimethylpropylene, n-hexylene, 2-methylpentylene, 2,2-dimethylbutylene, 2,3-dimethylbutylene.

The term "$C_{2-6}$ alkenyl" as used herein means an alkenyl group containing 2 to 6 carbon atoms, e.g. $C_{2-3}$, $C_{2-4}$, $C_{2-5}$ or $C_{2-6}$, and a double bond, such as one double bond, such as ethenyl, propenyl, butenyl, pentenyl or hexenyl, and also includes branched $C_{3-6}$ alkenyl, such as isopropenyl, isobutenyl, tert-butenyl, isopentenyl.

The term "$C_{1-x}$ alkoxy" or "O—$C_{1-6}$alkyl" (used interchangeable) as used herein means one oxygen atom covalently linked to an alkyl group containing 1 to x carbon atoms, e.g. $C_{1-5}$ or $C_{1-6}$, such as methoxy, ethoxy, n-propoxy, iso-propoxy, n-butyloxy, n-pentyloxy, or n-hexyloxy.

The term "$C_{3-7}$ cycloalkyl" as used herein means a cyclic alkyl group containing 3-7 carbon atoms, such as cyclopropyl, cyclobutyl, cyclopentyl, cyclohexyl, cycloheptyl, and 1-methylcyclopropyl.

The term "Oxo" as used herein means an oxygen atom with double bonds, also indicated as =O.

The term "CN" as used herein means a nitril (C and N linked by triple bond).

The term "C(=O)" as used herein means a carbonyl group.

When "$C_{1-6}$ alkyl" or "$C_{1-6}$ alkylene" is linked to another group or atom, such as in $C_{1-6}$ alkylene-OH, $C_{1-6}$ alkylene-CN, $C_{1-6}$ alkylene-$CF_3$, $C_{1-6}$ alkylene-O—$C_{1-6}$ alkyl, $C_{1-6}$ alkylene-S—$C_{1-6}$ alkyl, $C_{1-6}$ alkylene-NR$^a$R$^b$, C(=O)—$C_{1-6}$alkyl, C(=O)—$C_{1-6}$alkoxy, C(=O)—$C_{1-6}$ alkyl-CN, C(=O)—$C_{1-6}$ alkyl-OH, C(=O)—$C_{1-6}$ alkylene-S—$C_{1-6}$ alkyl, C(=O)—O—$C_{1-6}$ alkylene-O—$C_{1-6}$ alkyl, C(=O)—O—$C_{1-6}$ alkyl-CN, C(=O)—O—$C_{1-6}$ alkyl-OH, C(=O)—O—$C_{1-6}$ alkylene-S—$C_{1-6}$ alkyl, C(=O)—NH$C_{1-6}$ alkyl, C(=O)—NH$C_{1-6}$ alkylene-O—$C_{1-6}$ alkyl, C(=O)—NH$C_{1-6}$ alkylene-S—$C_{1-6}$ alkyl, C(=O)—NH$C_{1-6}$ alkyl-CN, C(=O)—NH$C_{1-6}$alkyl-OH, C(=O)—N($C_{1-6}$alkyl)$_2$, $SO_2$—$C_{1-6}$alkyl, $SO_2$—$C_{1-6}$ alkylene-O—$C_{1-6}$ alkyl, $SO_2$—

$C_{1-6}$ alkylene-S—$C_{1-6}$ alkyl, $SO_2$—$C_{1-6}$ alkyl-CN, $SO_2$—$C_{1-6}$ alkyl-OH, $SO_2$—$C_{1-6}$ alkyl-N($C_{1-6}$alkyl)$_2$, S—$C_{1-6}$ alkyl, $OC_{3-7}$ cycloalkyl, $SC_{3-7}$ cycloalkyl, $C_{1-6}$ alkylene-C(=O)—O—$C_{1-6}$ alkyl, $C_{1-6}$ alkylene-O—C(=O)—NH—$C_{1-6}$ alkyl, $C_{1-6}$ alkylene-NH—C(=O)—$C_{1-6}$ alkylene-O—$C_{1-6}$ alkyl, $C_{1-6}$ alkylene-NH—$SO_2$—$C_{1-6}$ alkyl, $C_{1-6}$ alkylene-NH—$SO_2$—$C_{1-6}$ alkylene-phenyl, $C_{1-6}$ alkylene-NR$^c$R$^d$, $C_{1-6}$ alkylene-C(=O)—NR$^e$R$^f$, $C_{1-6}$ alkylene-R$^g$, $C_{1-6}$ alkylene-R$^h$, $C_{1-6}$ alkylene-R$^j$, it means that one such group or atom may be linked covalently to any one of the carbon atoms of the $C_{1-6}$ alkyl or $C_{1-6}$ alkylene.

The term "halogen" as used herein means an atom selected from Chloro (Cl), Flouro (F), Iodo (I) and Bromo (Br).

The term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. The treatment may either be performed in an acute or in a chronic way. The patient to be treated is preferably a mammal; in particular a human being, but it may also include animals, such as dogs, cats, cows, sheep and pigs.

The term "a therapeutically effective amount" of a compound of formula (I) of the present invention as used herein means an amount sufficient to cure, alleviate or partially arrest the clinical manifestations of a given disease and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

In a still further aspect the present invention relates to a pharmaceutical composition comprising the compound of formula (I) and optionally a pharmaceutically acceptable additive, such as a carrier or an excipient.

As used herein "pharmaceutically acceptable additive" is intended without limitation to include carriers, excipients, diluents, adjuvant, colorings, aroma, preservatives etc. that the skilled person would consider using when formulating a compound of the present invention in order to make a pharmaceutical composition.

The adjuvants, diluents, excipients and/or carriers that may be used in the composition of the invention must be pharmaceutically acceptable in the sense of being compatible with the compound of formula (1) and the other ingredients of the pharmaceutical composition, and not deleterious to the recipient thereof. It is preferred that the compositions shall not contain any material that may cause an adverse reaction, such as an allergic reaction. The adjuvants, diluents, excipients and carriers that may be used in the pharmaceutical composition of the invention are well known to a person within the art.

As mentioned above, the compositions and particularly pharmaceutical compositions as herein disclosed may, in addition to the compounds herein disclosed, further comprise at least one pharmaceutically acceptable adjuvant, diluent, excipient and/or carrier. In some embodiments, the pharmaceutical compositions comprise from 1 to 99 weight % of said at least one pharmaceutically acceptable adjuvant, diluent, excipient and/or carrier and from 1 to 99 weight % of a compound as herein disclosed. The combined amount of the active ingredient and of the pharmaceutically acceptable adjuvant, diluent, excipient and/or carrier may not constitute more than 100% by weight of the composition, particularly the pharmaceutical composition.

In some embodiments, only one compound as herein disclosed is used for the purposes discussed above.

In some embodiments, two or more of the compound as herein disclosed are used in combination for the purposes discussed above.

The composition, particularly pharmaceutical composition comprising a compound set forth herein may be adapted for oral, intravenous, topical, intraperitoneal, nasal, buccal, sublingual, or subcutaneous administration, or for administration via the respiratory tract in the form of, for example, an aerosol or an air-suspended fine powder. Therefore, the pharmaceutical composition may be in the form of, for example, tablets, capsules, powders, nanoparticles, crystals, amorphous substances, solutions, transdermal patches or suppositories.

Further embodiments of the process are described in the experimental section herein, and each individual process as well as each starting material constitutes embodiments that may form part of embodiments.

The above embodiments should be seen as referring to any one of the aspects (such as 'method for treatment', 'pharmaceutical composition', 'compound for use as a medicament', or 'compound for use in a method') described herein as well as any one of the embodiments described herein unless it is specified that an embodiment relates to a certain aspect or aspects of the present invention.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way.

Any combination of the above-described elements in all possible variations thereof is encompassed by the invention unless otherwise indicated herein or otherwise clearly contradicted by context.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also pro-vide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

The present invention is further illustrated by the following examples that, however, are not to be construed as limiting the scope of protection. The features disclosed in the foregoing description and in the following examples may, both separately and in any combination thereof, be material for realizing the invention in diverse forms thereof.

Experimental Procedures
Automated Patch Clamping

Automated whole cell patch-clamp recordings were performed using a QPatch 16 HT system and single-hole Qplates (Biolin Scientific, Sophion, Denmark) on HEK-293 cells stably expressing the human SK3 channel ($hK_{Ca}0.2.3$). Cells were cultured and prepared for experiments using normal cell culturing procedures. A total of 4-5 million cells were used per experiment. The Qpatch automatically generates giga sealing, whole-cell formation, compound application and recording of current. $hK_{Ca}2.3$ currents were recorded in symmetrical $K^+$ solutions, with an intracellular solution consisting of in mM: KCl 108; KOH/EGTA (ethylene glycol-bis(2-aminoethylether)-N,N,N',N'-tetraacetic acid) 31.25/10; $CaCl_2$) 8.1; $MgCl_2$ 1.2; HEPES (2-[4-(2-hydroxyethyl)piperazin-1-yl]ethanesulfonic acid) 10; KOH 15, pH adjusted to pH=7.2 with HCl. The free calcium concentration was calculated to 400 nM. The extracellular solution consisted of in mM: KCl 150; $CaCl_2$) 0.1; $MgCl_2$ 3; HEPES 10; Glucose 10, pH=7.4 with KOH. The cells were held at 0 mV and $hK_{Ca}0.2.3$ currents were elicited by a linear voltage ramp from −80 mV to +80 mV (200 ms in duration) applied every 5th second. The compound application protocol consisted of 12 recording periods lasting from 50-200 s: 1) Baseline recordings in extracellular solution; 2) Application of the positive control N-methyl bicuculline (100 µM), which is characterized by full efficacy, fast on- and off-rate; 3-4) Wash-out; 5-9) Increasing concentrations of test compound to establish an IC50 value; 10-11) Wash-out; 12) positive control with compound NS8593 (N-[(1R)-1,2,3,4-tetrahydro-1-naphthalenyl]-1H-benzimidazol-2-amine) (1 µM). Data were sampled at 10 kHz, 4th order Bessel filter, cut-off frequency 3 kHz. Currents were compensated for run-down. Potency was quantified as the concentration needed to inhibit half of the SK channel activity and reported as an IC50 value. All effects of compounds of the present invention as tested were normalized to the observed inhibitory effect of N-methyl bicuculline.

Results

The examples described are potent inhibitors of the SK3 channel and have shown the following $IC_{50}$ in the Automated patch clamping assay described above:

Examples: 1, 1a, 1b, 2, 2a, 2b, 3, 4, 5, 7, 9, 10, 11, 12, 13, 14, 15, 16, 17, 18, 19, 20, 21, 22, 24, 25, 25a, 25b, 26, 26a, 26b all have an $IC_{50}$ below 10 µM.

Examples: 6, 8 all have an $IC_{50}$ below 100 µM.

Materials and Methods

Commercial reagents were used without further purification unless otherwise stated. Analytical TLC was performed on silica gel 60-$F_{254}$ (Merck) with detection by fluorescence and by immersion in a $KMnO_4$ solution [$KMnO_4$ solution recipe: Dissolve 1.5 g $KMnO_4$, 10 g $K_2CO_3$, and 1.25 mL 10% NaOH in 200 mL of water] followed by charring. Purification of compound was carried out by column chromatography on silica gel (60-120 mesh, Swambe Chemicals, India). NMR spectra such as $^1H$, $^{13}C$ and 2D COSY were recorded with Bruker AV 400 MHz spectrometer (400 MHz for 41, 100 MHz for $^{13}C$) at ambient temperature by using deuterated DMSO-d6, $CDCl_3$, or $CD_3OD$ as a solvent for NMR. Chemical shifts are reported in δ parts per million (ppm). ESI-MS was recorded on Agilent LC1200 series MS single quadrupole 6130 mass spectrometer.

Abbreviations Used in Experimental Section:
BOP=(Benzotriazol-1-yloxy)tris(dimethylamino)phosphonium hexafluorophosphate
PyBOP=(Benzotriazol-1-yloxy)tripyrrolidinophosphonium hexafluorophosphate
EDC.HCl=N-(3-Dimethylaminopropyl)-N'-ethylcarbodiimide hydrochloride
HBTU=N,N,N',N'-Tetramethyl-O-(1H-benzotriazol-1-yl)uronium hexafluorophosphate.

Grace Flash Chromatography System:

The Grace REVELERIS® Prep Purification System was used to perform sample purification by flash chromatography, using Flash Cartridges pre-packed with silica:

Columns Used:
Hi-Purit Flash Columns Silica (Normal Phase);
12 g, 60 A, max pressure 350 psi (24 bar),
24 g, 60 A, max pressure 350 psi (24 bar),
40 g, 60 A, max pressure 350 psi (24 bar),
80 g, 60 A, max pressure 350 psi (24 bar).
Solvents: Hexane, EtOAc, $CHCl_3$ and MeOH.

Example 1: Preparation of 2-[(1H-1,3-benzodiazol-2-yl)amino]-N,N-dimethyl-2-[3-(trifluoromethyl)phenyl]acetamide

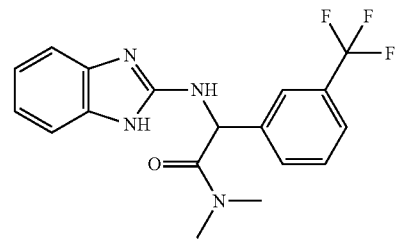 [SMILES: CN(C)C(=O)C(Nc1nc2ccccc2[nH]1)c1cccc(C(F)(F)F)c1]

Step 1: Synthesis of methyl 2-amino-2-(3-(trifluoromethyl)phenyl)acetate hydrochloride

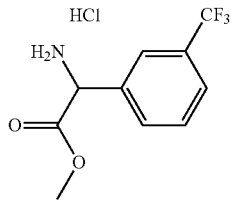 [SMILES: COC(=O)C(N)c1cccc(C(F)(F)F)c1 ; Cl]

To a well stirred solution of 2-amino-2-(3-(trifluoromethyl)phenyl)acetic acid (7 g, 32 mmol) in methanol (70 mL) was added thionyl chloride (4.6 mL, 64 mmol) at 0° C. and refluxed for 16 h. The reaction mixture was concentrated. The residue was washed with diethyl ether (3×100 mL) to afford methyl 2-amino-2-(3-(trifluoromethyl)phenyl)acetate hydrochloride as the hydrochloride salt (7 g).

$^1$H NMR (400 MHz, DMSO-$d_6$) δ 9.32 (s, 3H), 7.98 (s, 1H), 7.98-7.80 (m, 2H), 7.71 (t, 1H, J=7.6 Hz), 5.48 (d, 1H, J=4.40 Hz), 3.71 (s, 3H); MS: m/z 234.0 (M+1).

Step 2: Synthesis of methyl 2-[(1H-1,3-benzodiazol-2-yl)amino]-2-[3-(trifluoromethyl)phenyl]acetate

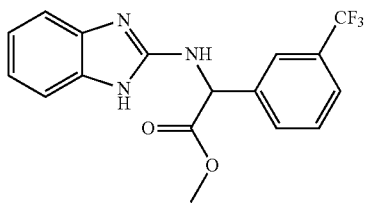 [SMILES: COC(=O)C(Nc1nc2ccccc2[nH]1)c1cccc(C(F)(F)F)c1]

A mixture of methyl 2-amino-2-(3-(trifluoromethyl) phenyl)acetate (from step 1) (10 g, 66 mmol) and 2-chloro-1H-benzimidazole (15.3 g, 66 mmol) in acetonitrile (160 mL) was irradiated in a microwave oven at 145° C. for 3 h. The crude mixture was purified by column chromatography on silica gel (eluted with 3% methanol in chloroform) to give the desired product as an off-white solid (12 g).

$^1$H NMR (400 MHz, DMSO-$d_6$) δ 10.75 (s, 1H), 7.90 (s, 1H), 7.84 (d, 1H, J=7.68 Hz), 7.79 (d, 1H, J=7.60 Hz), 7.73 (d, 1H, J=7.64 Hz), 7.66 (t, 1H, J=7.72 Hz), 7.18 (d, 2H, J=8.36 Hz), 6.90 (s, 2H), 5.78 (d, 1H, J=7.80 Hz), 3.67 (s, 3H); MS: m/z 350.0 (M+1).

Step 3: Preparation of 2-[(1H-1,3-benzodiazol-2-yl)amino]-N,N-dimethyl-2-[3-(trifluoromethyl)phenyl]acetamide

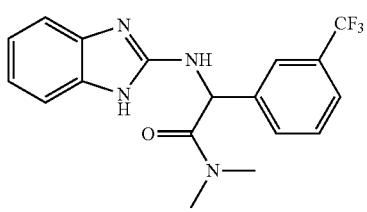 [SMILES: CN(C)C(=O)C(Nc1nc2ccccc2[nH]1)c1cccc(C(F)(F)F)c1]

To a solution of methyl methyl 2-[(1H-1,3-benzodiazol-2-yl)amino]-2-[3-(trifluoromethyl)phenyl]acetate (from step 2) (0.8 g, 2 mmol) in THF (10 mL) was added potassium carbonate (46 mmol), followed by dimethylamine hydrochloride (46 mmol). Then the reaction mixture was heated at 70° C. After 4 h, reaction mixture was diluted with water, extracted with chloroform (3×100 mL). The combined organic extracts were dried over anhydrous sodium sulphate and evaporated to afford the crude product (1 g) as a brownish gum. The crude product was purified by silica gel (60-120 mesh) using 3% methanol in chloroform as eluent to afford 2-[(1H-1,3-benzodiazol-2-yl)amino]-N,N-dimethyl-2-[3-(trifluoromethyl)phenyl]acetamide (270 mg) as an off-white solid.

$^1$H NMR (400 MHz, DMSO-$d_6$) δ 12.89 (s, 1H), 9.75 (d, 1H, J=8.6 Hz), 7.99 (s, 1H), 7.95 (d, 1H, J=7.64 Hz), 7.78 (d, 1H, J=7.80 Hz), 7.71 (t, 1H, J=7.72 Hz), 7.47-7.43 (m, 2H), 7.27-7.24 (m, 2H), 6.4 (d, 1H, J=8.4 Hz), 3.04 (s, 3H), 2.91 (s, 3H); MS: M/z 363 (M+1).

The above product (270 mg) was resolved into its two isomers by chiral HPLC.
Method information: Column: CHIRAL PAK AD-H (250× 4.6) mm 5u, Mobile
Phase 'A': HEXANE:ETHANOL (50:50), Flow: 1.0 ml/min

Example 1a: (−)2-[(1H-1,3-benzodiazol-2-yl)amino]-N,N-dimethyl-2-[3-(trifluoromethyl)phenyl]acetamide The (−) enantiomer (70 mg) was the first to elute off the column.

$^1$H NMR (400 MHz, DMSO-$d_6$) δ 12.72 (s, 1H), 9.74 (s, 1H), 7.96 (s, 1H), 7.91 (d, 1H, J=7.84 Hz), 7.79 (d, 1H, J=7.88 Hz), 7.71 (t, 1H, J=7.80 Hz), 7.45 (dd, 2H, J=3.20, 5.80 Hz), 7.25 (dd, 2H, J=3.24, 5.86 Hz), 6.30 (d, 1H, J=8.60 Hz), 3.02 (s, 3H), 2.92 (s, 3H);
MS: M/z 363 (M+1); $[α]_D^{25.0}$=−111.82 (MeOH, c=0.110).

Example 1b: (+)2-[(1H-1,3-benzodiazol-2-yl)amino]-N,N-dimethyl-2-[3-(trifluoromethyl)phenyl]acetamide The (+) enantiomer (80 mg) was the second to elute off the column.

$^1$H NMR (400 MHz, DMSO-$d_6$) δ 12.0 (s, 1H), 9.73 (s, 1H), 7.96 (s, 1H), 7.91 (d, 1H, J=8.04 Hz), 7.78 (d, 1H, J=7.28 Hz), 7.71 (t, 1H, J=7.52 Hz), 7.45 (dd, 2H, J=3.12, 5.80 Hz), 7.25 (dd, 2H, J=3.24, 5.84 Hz), 6.31 (d, 1H, J=8.36 Hz), 3.02 (s, 3H), 2.92 (s, 3H);
MS: M/z 363 (M+1); $[α]_D^{25.0}$=100.0 (MeOH, c=0.115).

Example 2: 3-[(1H-1,3-benzodiazol-2-yl)amino]-N-methyl-3-[3(trifluoromethyl)phenyl]propanamide

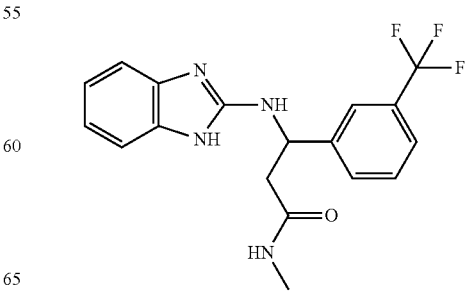

Step 1: Preparation of methyl 3-isothiocyanato-3-[3-(trifluoromethyl)phenyl]propanoate

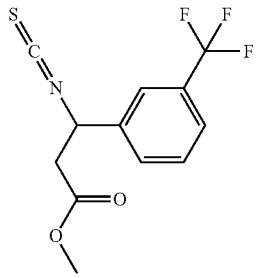 [SMILES: COC(=O)CC(N=C=S)c1cccc(C(F)(F)F)c1]

To a suspension of methyl 3-amino-3-[3-(trifluoromethyl)phenyl]propanoate hydrochloride (65 g, 230 mmol) in dichloromethane (150 mL) at 0° C. was added thiophosgene (35.4 mL, d=1.5 g/mL, 461 mmol) followed by 10% aqueous sodium bicarbonate solution (150 mL). The reaction mixture was then stirred at ambient temperature. After 1 h, the reaction mixture was diluted with 10% aqueous sodium bicarbonate solution (75 mL) and extracted with dichloromethane (3×250 mL). The combined organic extracts were dried over anhydrous sodium sulphate and evaporated to dryness to afford methyl 3-isothiocyanato-3-[3-(trifluoromethyl)phenyl]propanoate (60 g) as a red gum.

$^{1}$H NMR (400 MHz, CDCl$_3$) δ 7.65-7.54 (m, 4H), 5.38 (q, 1H, J=8.0 Hz), 3.77 (s, 3H), 3.02 (dd, 1H, J=8.8, 8.8 Hz), 2.86 (dd, 1H, J=5.2, 5.2 Hz); MS: m/z 289.1 (M+).

Step 2: Preparation of methyl 3-{[(2-aminophenyl)carbamothioyl]amino}-3-[3-(trifluoromethyl)phenyl]propanoate

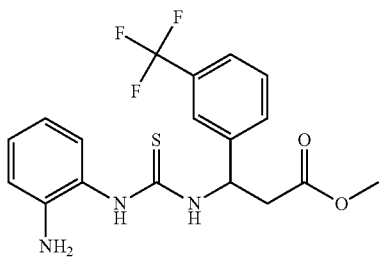 [SMILES: COC(=O)CC(NC(=S)Nc1ccccc1N)c1cccc(C(F)(F)F)c1]

A mixture of methyl 3-isothiocyanato-3-[3-(trifluoromethyl)phenyl]propanoate (from step 1) (60 g, 207 mmol) and 1,2-phenylenediamine (22.43 g, 207 mmol) in dichloromethane (200 mL) was stirred at ambient temperature for 12 h. The reaction mixture was concentrated to afford a crude product (85 g) as a brownish gum, which was purified by silica gel (60-120 mesh) column chromatography eluting with 7% methanol in chloroform to afford methyl 3-{[(2-aminophenyl)carbamothioyl]amino}-3-[3-(trifluoromethyl)phenyl] propanoate (55 g) as a brownish gum.

$^{1}$H NMR (400 MHz, DMSO-d$_6$) δ 9.05 (s, 1H), 7.90 (s, 1H), 7.45-7.31 (m, 4H), 6.78-6.71 (m, 2H), 6.53 (d, 1H, J=7.6 Hz), 6.34 (t, 1H, J=7.6 Hz), 5.69 (bs, 1H), 3.28 (s, 3H), 2.83 (dd, 1H, J=16.0, 8.0 Hz), 2.70 (dd, 1H, J=16.0, 6.4 Hz); MS: m/z 398 (M+1).

Step 3: Preparation of methyl 3-[(1H-1,3-benzodiazol-2-yl)amino]-3-[3-(trifluoromethyl)phenyl] propanoate

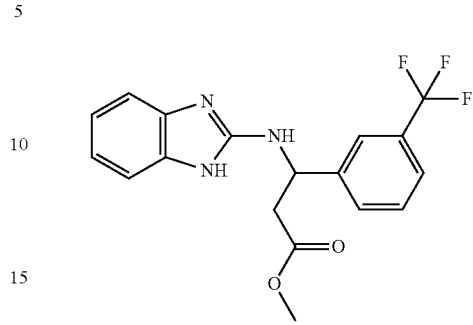

To a solution of methyl 3-{[(2-aminophenyl)carbamothioyl]amino}-3-[3-(trifluoromethyl)phenyl] propanoate (from step 2) (55 g, 134 mmol) in methanol (550 mL) was added iodoacetic acid (32.19 g, 174 mmol) and the mixture was refluxed for 2 h. The reaction mixture was evaporated to afford the crude product (90 g) which was purified by silica gel (60-120 mesh) column chromatography using 7% methanol in chloroform as eluent to afford methyl 3-[(1H-1,3-benzodiazol-2-yl)amino]-3-[3-(trifluoromethyl)phenyl] propanoate (37 g) as an off-white solid.

$^{1}$H NMR (400 MHz, MeOH-d$_4$) δ 7.83-7.78 (m, 2H), 7.71-7.64 (m, 2H), 7.42-7.39 (m, 2H), 7.32-7.30 (m, 2H), 5.39 (t, 1H, J=7.2 Hz), 3.70 (s, 3H), 3.14 (d, 2H, J=8.0 Hz); MS: m/z 364.0 (M+1).

Example 2, step 4: 3-[(1H-1,3-benzodiazol-2-yl)amino]-N-methyl-3-[3-(trifluoromethyl)phenyl]propanamide

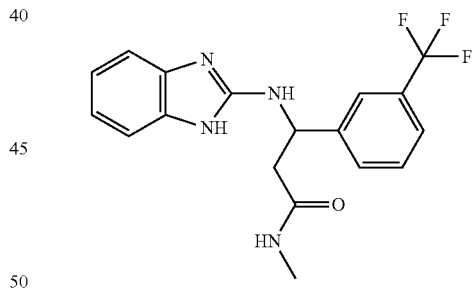

To a solution of methyl 3-[(1H-1,3-benzodiazol-2-yl)amino]-3-[3-(trifluoromethyl)phenyl] propanoate (from step 3) (25 g, 69 mmol) in THF (100 mL) was added aqueous methylamine (40% solution in water, 75 mL, 6881 mmol) at 0° C. and the reaction mixture was warmed to ambient temperature and stirred for 1 h. The reaction mixture was diluted with water (50 mL), extracted with dichloromethane (3×50 mL). The combined organic extracts were dried over anhydrous sodium sulphate and evaporated to afford 3-[(1H-1,3-benzodiazol-2-yl)amino]-N-methyl-3-[3-(trifluoromethyl)phenyl]propanamide (20 g) as an off white solid.

$^{1}$H NMR (400 MHz, MeOH-d$_4$) δ 7.78 (d, 1H, J=0.36 Hz), 7.72 (d, 1H, J=7.04 Hz), 7.57-7.51 (m, 2H), 7.19-7.17 (m, 2H), 6.98-6.94 (m, 2H), 5.36 (t, 1H, J=6.76 Hz), 2.79 (dd, 2H, J=5.52, 7.08 Hz), 2.65 (s, 3H); MS: m/z 363.0 (M+1).

The above product (20 g) was resolved into its two isomers by chiral SFC. Method:

Column: YMC Cellulose C; Mobile Phase 'A': 20 mM Ammonia in Methanol; Flow: 1.0 ml/min.

Example 2a: (−)3-[(1H-1,3-benzodiazol-2-yl)amino]-N-methyl-3-[3(trifluoromethyl)phenyl]propanamide The (−) enantiomer (8.5 g) was the first to elute off the column.

$^1$H NMR (400 MHz, MeOH-d$_4$) δ 7.78 (s, 1H), 7.72 (d, 1H, J=6.80 Hz), 7.55-7.53 (m, 2H), 7.18 (dd, 2H, J=3.20, 6.00 Hz), 6.97 (dd, 2H, J=3.20, 6.40 Hz), 5.36 (t, 1H, J=6.40 Hz), 2.80 (td, 2H, J=5.20, 7.20 Hz), 2.67 (s, 3H); MS: m/z 363.0 (M+1); $[\alpha]_D^{24.6}$=−36.6 (MeOH, c=0.10).

Example 2b: (+)3-[(1H-1,3-benzodiazol-2-yl)amino]-N-methyl-3-[3-(trifluoromethyl)phenyl]propanamide The (+) enantiomer (8 g) was the second to elute off the column.

$^1$H NMR (400 MHz, MeOH-d$_4$) δ 7.78 (d, 1H, J=0.36 Hz), 7.72 (d, 1H, J=7.12 Hz), 7.57-7.51 (m, 2H), 7.18 (dd, 2H, J=3.20, 5.88 Hz), 6.97 (dd, 2H, J=3.20, 5.88 Hz), 5.36 (t, 1H, J=6.76 Hz), 2.80 (dd, 2H, J=5.36, 7.08 Hz), 2.65 (s, 3H);

MS: m/z 363.0 (M+1); $[\alpha]_D^{27.3}$=+38.4 (MeOH, c=0.13).

Example 3: 3-[(1H-1,3-benzodiazol-2-yl)amino]-N-(prop-2-en-1-yl)-3-[3-(trifluoromethyl)phenyl]propanamide

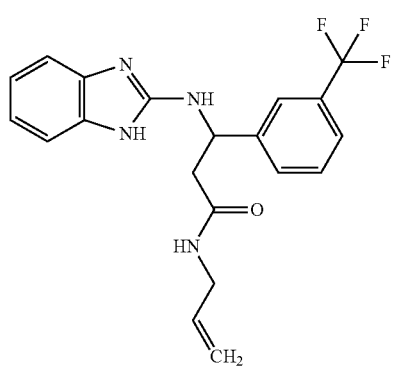 [SMILES: C=CCNC(=O)CC(Nc1nc2ccccc2[nH]1)c1cccc(C(F)(F)F)c1]

A suspension of methyl 3-[(1H-1,3-benzodiazol-2-yl)amino]-3-[3-(trifluoromethyl)phenyl]propanoate (from Example 2, step 3) (0.30 g, 0.825 mmol) and prop-2-en-1-amine (0.118 g, 2.0 mmol) in acetonitrile (10 mL) was irradiated at 140° C. under microwave conditions for 3 h. The crude product was purified by silica gel (60-120 mesh) column chromatography using 3% methanol in chloroform as eluent to afford 3-[(1H-1,3-benzodiazol-2-yl)amino]-N-(prop-2-en-1-yl)-3-[3-(trifluoromethyl)phenyl]propanamide (0.150 g) as off-white solid.

$^1$H NMR (400 MHz, DMSO-d$_6$) δ 11.0 (s, 1H), 8.09 (t, 1H, J=5.72 Hz), 7.80 (s, 1H), 7.73 (d, 1H, J=7.08 Hz), 7.57 (dd, 3H, J=7.68, 9.94 Hz), 7.11 (t, 2H, J=4.52 Hz), 6.86 (dd, 2H, J=3.00, 5.52 Hz), 5.68-5.63 (m, 1H), 5.39 (q, 1H, J=8.60 Hz), 4.93-4.89 (m, 2H), 3.63 (dd, 2H, J=5.08, 10.42 Hz), 2.79-2.68 (m, 2H);

MS: M/z 389 (M+1).

Example 4: Preparation of 3-[(5-fluoro-4-methyl-1H-1,3-benzodiazol-2-yl)amino]-N-methyl-3-[3-(trifluoromethyl)phenyl]propanamide

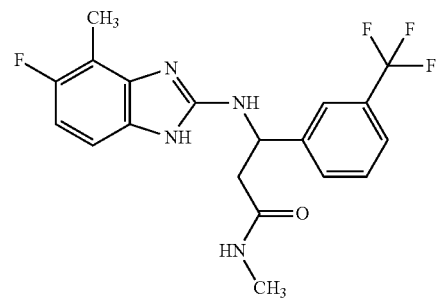 [SMILES: CNC(=O)CC(Nc1nc2c(C)c(F)ccc2[nH]1)c1cccc(C(F)(F)F)c1]

The procedures described in Example 2, steps 2 to 4 where applied with 4-fluoro-3-methylbenzene-1,2-diamine to afford 3-[(5-fluoro-4-methyl-1H-1,3-benzodiazol-2-yl)amino]-N-methyl-3-[3-(trifluoromethyl)phenyl]propanamide.

$^1$H NMR (400 MHz, MeOH-d$_4$) δ 7.77 (s, 1H), 7.71 (d, 1H, J=7.20 Hz), 7.56 (t, 2H, J=2.00 Hz), 6.93 (dd, 1H, J=4.40, 8.40 Hz), 6.68 (t, 1H, J=1.60 Hz), 5.37 (t, 1H, J=6.40 Hz), 2.80 (d, 2H, J=6.40 Hz), 2.64 (s, 3H), 2.33 (s, 3H); MS: M/z 395 (M+1).

Example 5: Preparation of N-methyl-3-[(4-methyl-1H-1,3-benzodiazol-2-yl)amino]-3-[3-(trifluoromethyl)phenyl]propanamide

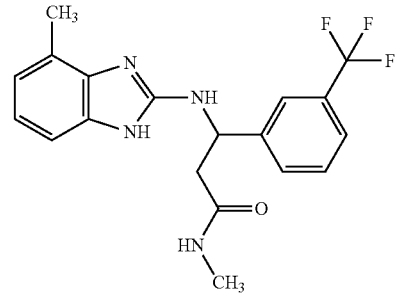

The procedures described in Example 2, steps 2 to 4 where applied with 3-methylbenzene-1,2-diamine to afford N-methyl-3-[(4-methyl-1H-1,3-benzodiazol-2-yl)amino]-3-[3-(trifluoromethyl)phenyl]propanamide.

$^1$H NMR (400 MHz, MeOH-d$_4$) δ 7.78 (s, 1H), 7.72 (d, 1H, J=6.40 Hz), 7.53 (dd, 2H, J=7.60, 15.40 Hz), 7.01 (d, 1H, J=6.80 Hz), 6.86 (t, 1H, J=7.60 Hz), 6.77 (d, 1H, J=7.20 Hz), 5.39 (t, 1H, J=6.40 Hz), 2.80 (d, 2H, J=6.00 Hz), 2.64 (s, 3H), 2.41 (s, 3H);

MS: M/z 377 (M+1).

Example 6: Synthesis of 3-{[4-(2-hydroxyethyl)-1H-1,3-benzodiazol-2-yl]amino}-N-methyl-3-[3-(trifluoromethyl)phenyl]propanamide

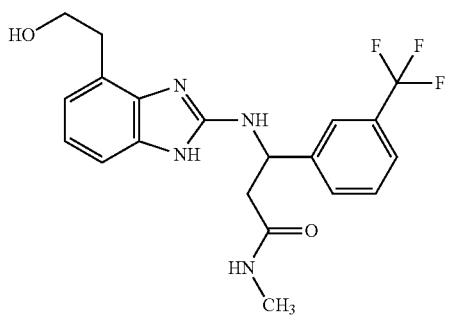 [SMILES: CNC(=O)CC(Nc1nc2c(CCO)cccc2[nH]1)c1cccc(C(F)(F)F)c1]

The procedures described in Example 2, steps 2 to 4 where applied with 2-(2,3-diaminophenyl)ethan-1-ol to afford 3-{[4-(2-hydroxyethyl)-1H-1,3-benzodiazol-2-yl]amino}-N-methyl-3-[3-(trifluoromethyl)phenyl]propanamide.

$^1$H NMR (400 MHz, MeOH-$d_4$) δ 7.78 (s, 1H), 7.72 (d, 1H, J=7.20 Hz), 7.53 (dd, 2H, J=7.20, Hz), 7.05 (d, 1H, J=7.60 Hz), 6.90 (t, 1H, J=7.60 Hz), 6.82 (d, 1H, J=7.20 Hz), 5.37 (t, 1H, J=6.40 Hz), 3.82 (t, 2H, J=6.80 Hz), 3.00 (t, 2H, J=6.80 Hz), 2.80 (dd, 2H, J=2.40, 6.60 Hz), 2.64 (s, 3H); MS: M/z 407 (M+1).

Example 7: Preparation of methyl 2-[(4-acetamido-1H-1,3-benzodiazol-2-yl)amino]-3-[3-(trifluoromethyl)phenyl]propanoate

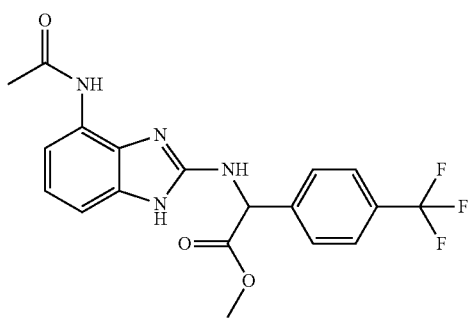 [SMILES: COC(=O)C(Nc1nc2c(NC(C)=O)cccc2[nH]1)c1ccc(C(F)(F)F)cc1]

Step 1: Preparation of 2-chloro-1H-1,3-benzodiazol-4-amine

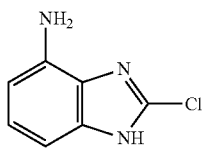

To a mixture of concentrated hydrochloric acid (100 mL) and SnCl$_2$ (18.27 g, 81 mmol), was added 2-chloro-4-nitro-1H-1,3-benzodiazole (4 g, 2 mol), at 0° C. The reaction mixture was allowed to warm to ambient temperature and stirred. Reaction mixture was poured into ice-cold water, basified with sodium bicarbonate and extracted with 30% methanol in chloroform mixture (7×200 mL). The combined organic extracts were dried over anhydrous sodium sulphate and evaporated to afford 2-chloro-1H-1,3-benzodiazol-4-amine (3 g) as brownish semi-solid.

$^1$H NMR (400 MHz, DMSO-$d_6$) δ 12.83 (s, 1H), 6.92 (t, 1H, J=7.16 Hz), 6.58 (d, 1H, J=7.96 Hz), 6.36 (d, 1H, J=7.80 Hz), 5.2 (s, 2H); MS: M/z 168 (M+1).

Step 2: Preparation of N-(2-chloro-1H-1,3-benzodiazol-4-yl)acetamide

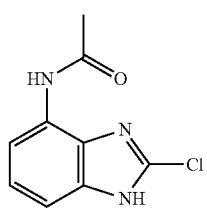

To a solution of 2-chloro-1H-1,3-benzodiazol-4-amine (from step 1) (2 g, 12 mmol), in acetonitrile (75 mL) was added acetyl chloride (1.03 g, 13 mmol) at 0° C. and stirred for 30 min. After 30 min, the solid formed was filtered and dried to afford N-(2-chloro-1H-1,3-benzodiazol-4-yl)acetamide (1.5 g) as off-white solid.

$^1$H NMR (400 MHz, DMSO-$d_6$) δ 9.97 (s, 1H), 7.76 (d, 1H, J=7.72 Hz), 7.20 (d, 1H, J=7.44 Hz), 7.14 (t, 1H, J=7.96 Hz), 5.16 (bs, 1H), 2.13 (s, 3H); MS: M/z 210 (M+1).

Step 3: Preparation of methyl 2-[(4-acetamido-1H-1,3-benzodiazol-2-yl)amino]-3-[3-(trifluoromethyl)phenyl]propanoate

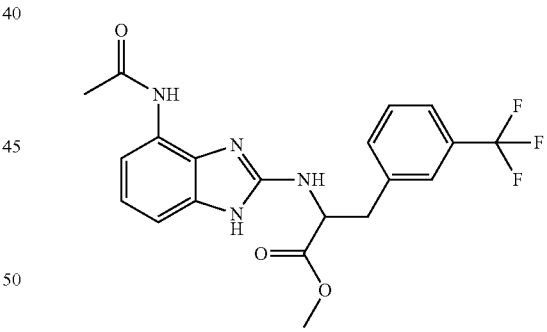

A suspension of N-(2-chloro-1H-1,3-benzodiazol-4-yl)acetamide (from step 2) (0.4 g, 2.0 mmol) and methyl 2-amino-3-(3-(trifluoromethyl)phenyl)propanoate (0.566 g, 2.4 mmol) in acetonitrile (15 mL) was irradiated at 120° C. in a microwave oven. After 5 h, reaction mixture was evaporated as such to afford the crude product (350 mg) as a brown gum. The crude product was purified by silica gel (60-120 mesh) column chromatography using 3% methanol in chloroform as eluent to afford methyl 2-[(4-acetamido-1H-1,3-benzodiazol-2-yl)amino]-3-[3-(trifluoromethyl)phenyl]propanoate (0.140 g) as off-white solid.

$^1$H NMR (400 MHz, DMSO-$d_6$) δ 10.13 (s, 1H), 9.91 (s, 1H), 7.62-7.52 (m, 4H), 7.25 (d, 1H, J=7.44 Hz), 6.96 (d, 1H, J=7.12 Hz), 6.87 (t, 2H, J=7.72 Hz), 4.75-4.70 (m, 1H), 3.65 (d, 3H, J=7.84 Hz), 3.28 (t, 1H, J=8.5 Hz), 3.16 (dd, 1H, J=3.60, 5.20 Hz), 2.10 (s, 3H);

MS: M/z 421 (M+1).

Example 8: Preparation of 2-[(1H-1,3-benzodiazol-2-yl)amino]-N-methyl-3-[3-(trifluoromethyl)phenyl] propanamide

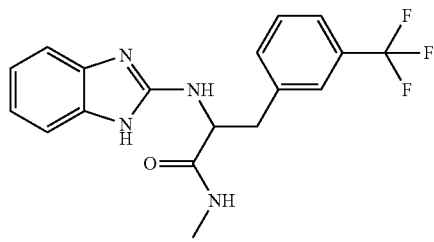 [SMILES: CNC(=O)C(Cc1cccc(C(F)(F)F)c1)Nc1nc2ccccc2[nH]1]

Step 1: Preparation of methyl 2-amino-3-[3-(trifluoromethyl)phenyl]propanoate hydrochloride

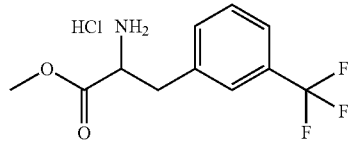 [SMILES: COC(=O)C(N)Cc1cccc(C(F)(F)F)c1 ; Cl]

To a well stirred solution of 2-amino-3-(3-(trifluoromethyl)phenyl)propanoic acid (2.5 g, 11 mmol) in methanol (50 mL) was added thionyl chloride (2.0 mL, 27 mmol) at 0° C. and then refluxed for 20 h. The reaction mixture was concentrated, the residue was washed with diethyl ether (20× mL) to afford methyl 2-amino-3-(3-(trifluoromethyl) phenyl)propanoate hydrochloride salt as a white solid (2.5 g).

$^1$H NMR (400 MHz, DMSO-$d_6$ & $D_2O$) δ 7.66 (d, 2H, J=7.52 Hz), 7.61-7.54 (m, 2H), 4.38 (t, 1H, J=6.64 Hz), 3.68 (s, 3H), 3.22 (dd, 2H, J=2.28, 6.72 Hz);

MS: m/z 248 (M+1) (free base).

Step 2: Preparation of methyl 2-isothiocyanato-3-(3-(trifluoromethyl)phenyl)propanoate

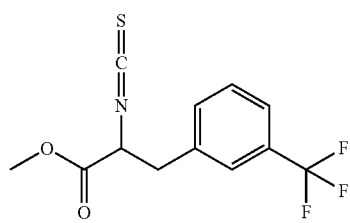 [SMILES: COC(=O)C(Cc1cccc(C(F)(F)F)c1)N=C=S]

To a suspension of methyl 2-amino-3-(3-(trifluoromethyl) phenyl)propanoate hydrochloride (from step 1) (1.5 g, 0.61 mmol) in dichloromethane (50 mL) was added thiophosgene (0.7 mL, 0.91 mmol) at 0° C. followed by aqueous sodium bicarbonate solution (10%, 30 mL) and the reaction mixture was stirred at ambient temperature for 1 h. The reaction mixture was extracted with dichloromethane (3×50 mL). The combined organic extracts were dried over anhydrous sodium sulphate and evaporated to afford methyl 2-isothiocyanato-3-(3-(trifluoromethyl) phenyl)propanoate (1.5 g) as a yellow gum.

MS: m/z 289.9 (M+1).

Step 3: Preparation of methyl 2-{[(2-aminophenyl) carbamothioyl]amino}-3-[3-(trifluoromethyl)phenyl] propanoate

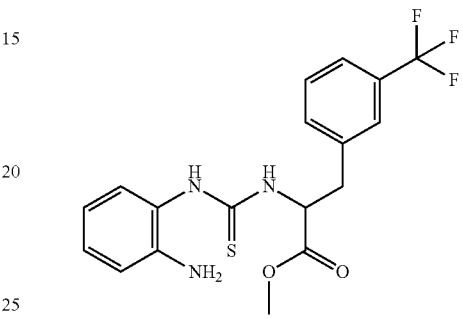

A mixture of methyl 2-isothiocyanato-3-(3-(trifluoromethyl) phenyl)propanoate (from step 2) (1.2 g, 4.1 mmol) and 1,2-phenylenediamine (0.56 g, 5.0 mmol) in dichloromethane (50 mL) was stirred at ambient temperature for 12 h. The reaction mixture was concentrated, purified by column chromatography on silica gel (60-120 mesh) using 3% methanol in chloroform as eluent to give the desired product methyl 2-{[(2-aminophenyl)carbamothioyl] amino}-3-[3-(trifluoromethyl)phenyl]propanoate as yellow gum (1 g).

MS: m/z 398.2 (M+1).

Step 4: Preparation of methyl 2-[(1H-1,3-benzodiazol-2-yl)amino]-3-[3-(trifluoromethyl)phenyl]propanoate

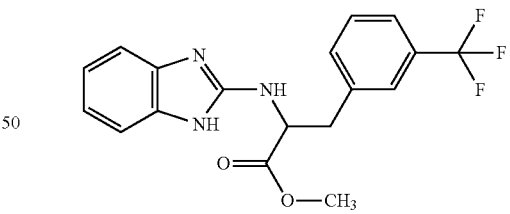

To a solution of methyl 2-{[(2-aminophenyl)carbamothioyl]amino}-3-[3-(trifluoromethyl)phenyl]propanoate (from step 3) (0.3 g, 0.73 mmol) in methanol (10 mL) was added iodoacetic acid (0.14 g, 0.73 mmol) and the reaction mixture was refluxed for 2 h. The reaction mixture was evaporated and the crude was purified by prep. HPLC to give the desired product (0.15 g) as an off-white solid.

$^1$H NMR (400 MHz, MeOH-$d_4$) δ 7.63 (s, 1H), 7.61-7.53 (m, 3H), 7.38-7.35 (m, 2H), 7.32-7.29 (m, 2H), 4.76 (dd, 1H, J=5.20, 9.20 Hz), 3.84 (s, 3H), 3.54 (dd, 1H, J=5.20, 14.40 Hz), 3.31-3.25 (m, 1H);

MS: m/z 364 (M+1).

Example 8, step 5: Preparation of 2-[(1H-1,3-benzodiazol-2-yl)amino]-N-methyl-3-[3-(trifluoromethyl)phenyl]propanamide

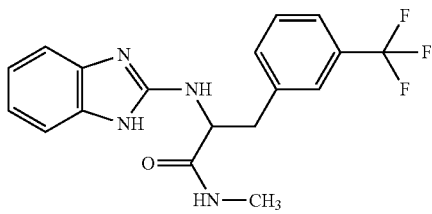 [SMILES: CNC(=O)C(Cc1cccc(C(F)(F)F)c1)Nc1nc2ccccc2[nH]1]

To a solution of methyl 2-[(1H-1,3-benzodiazol-2-yl)amino]-3-[3-(trifluoromethyl)phenyl]propanoate (from step 4) (0.1 g, 279 mmol) in THF (5 mL) was added aqueous methylamine (40% solution in water, 5 mL) at 0° C. and the reaction mixture was warmed to ambient temperature and stirred for 1 h. The reaction mixture was diluted with water (25 mL), extracted with dichloromethane (3×50 mL). The combined organic extracts were dried over anhydrous sodium sulphate and evaporated to afford 2-[(1H-1,3-benzodiazol-2-yl)amino]-N-methyl-3-[3-(trifluoromethyl)phenyl]propanamide (0.05 g) as off white solid.

$^1$H NMR (400 MHz, MeOH-$d_4$) δ 7.61 (s, 1H), 7.56 (d, 1H, J=7.60 Hz), 7.52-7.45 (m, 2H), 7.20 (s, 2H), 6.99 (dd, 2H, J=3.20, 6.00 Hz), 4.62 (dd, 1H, J=6.40, 7.60 Hz), 3.33-3.29 (m, 1H), 3.17 (dd, 1H, J=8.00, 13.80 Hz), 2.72 (s, 3H);

MS: m/z 363 (M+1).

Example 9: Preparation of 3-[(1H-1,3-benzodiazol-2-yl)amino]-3-(4-fluoro-3,5-dimethylphenyl)-N-methylpropanamide

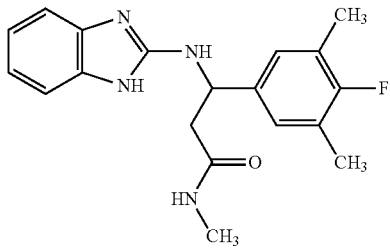 [SMILES: CNC(=O)CC(Nc1nc2ccccc2[nH]1)c1cc(C)c(F)c(C)c1]

Step 1: Preparation of 3-amino-3-(4-fluoro-3,5-dimethylphenyl)propanoic acid

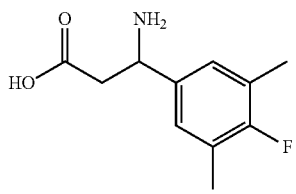

A mixture of malonic acid (1.026 g, 10 mmol), ammonium formate (1.243 g, 20 mmol) and 4-fluoro-3,5-dimethylbenzaldehyde (1.5 g, 10 mmol) in ethanol (10 mL) was refluxed for 24 h. The reaction mixture was evaporated to remove ethanol and the residue was triturated with acetone (2×250 mL). The solid was filtered and dried to afford 3-amino-3-(4-fluoro-3,5-dimethylphenyl)propanoic acid (1.1 g) as a white solid.

$^1$H NMR (400 MHz, DMSO-$d_6$) δ 8.41 (s, 2H, D$_2$O exchangeable), 7.14 (d, 2H, J=6.8 Hz), 4.17 (dd, 1H, J=8.8, 4.6 Hz), 2.33 (t, 2H, J=9.9 Hz), 2.20 (s, 6H);

MS: m/z 212 (M+1).

Step 2: Preparation of methyl 3-amino-3-(4-fluoro-3,5-dimethylphenyl)propanoate hydrochloride

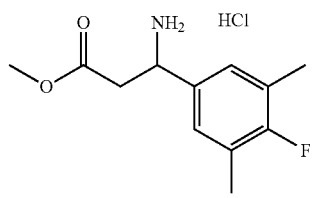 [SMILES: Cl ; COC(=O)CC(N)c1cc(C)c(F)c(C)c1]

To a stirred suspension of 3-amino-3-(4-fluoro-3,5-dimethylphenyl)propanoic acid (from step 1) (1.1 g, 5 mmol) in methanol (50 mL) was added thionyl chloride (0.75 mL, d=1.64 g/mL, 10 mmol) dropwise at 0° C. over a period of 15 m. After the completion of addition, the reaction mixture was heated at 80° C. The reaction mixture was cooled to ambient temperature, concentrated under reduced pressure to afford 2.0 g of methyl 3-amino-3-(4-fluoro-3,5-dimethylphenyl)propanoate hydrochloride as a yellowish gum. This was triturated with dichloromethane (2×200 mL), filtered, the filtrate was concentrated under reduced pressure to afford methyl 3-amino-3-(4-fluoro-3,5-dimethylphenyl) propanoate hydrochloride (1.8 g) as an off-white solid.

$^1$H NMR (400 MHz, DMSO-$d_6$) δ 8.60 (bs, 2H, D$_2$O exchangeable), 7.14 (s, 2H), 4.50 (d, 1H, J=5.8 Hz), 3.56 (s, 3H), 3.14 (dd, 1H, J=9.4, 7.48 Hz), 2.98 (dd, 1H, J=16.36, 8.64 Hz), 2.21 (d, 6H, J=1.7 Hz);

MS: m/z 226 (M+1).

Step 3: Preparation of methyl 3-(4-fluoro-3,5-dimethylphenyl)-3-isothiocyanatopropanoate

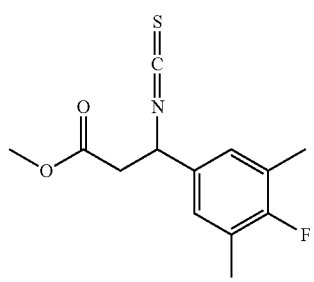 [SMILES: COC(=O)CC(N=C=S)c1cc(C)c(F)c(C)c1]

To a suspension of methyl 3-amino-3-(4-fluoro-3,5-dimethylphenyl)propanoate hydrochloride (from step 2)(1.2 g, 5 mmol) in dichloromethane (50 mL) cooled at 0° C. was added thiophosgene (1.05 mL, d=1.5 g/mL, 14 mmol) followed by 10% aqueous sodium bicarbonate solution (10 mL). The reaction mixture was then stirred at ambient temperature. After 2 h, the reaction mixture was diluted with 10% aqueous sodium bicarbonate solution (50 mL) and extracted with dichloromethane (3×50 mL). The combined organic extracts were dried over anhydrous sodium sulphate and evaporated to dryness to afford methyl 3-(4-fluoro-3,5-dimethylphenyl)-3-isothiocyanatopropanoate (1.1 g) as a red gum.

MS: m/z 268 (M+1).

Step 4: Preparation of methyl 3-{[(2-aminophenyl)carbamothioyl]amino}-3-(4-fluoro-3,5-dimethylphenyl)propanoate

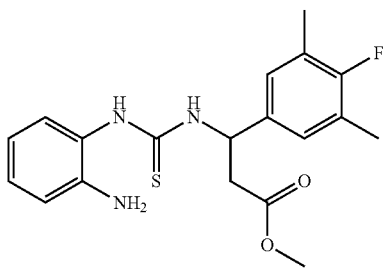 [SMILES: COC(=O)CC(NC(=S)Nc1ccccc1N)c1cc(C)c(F)c(C)c1]

A mixture of methyl 3-(4-fluoro-3,5-dimethylphenyl)-3-isothiocyanatopropanoate (from step 3)(0.98 g, 4 mmol) and 1,2-phenylenediamine (0.4 g, 4 mmol) in dichloromethane (25 mL) was stirred at ambient temperature for 12 h. The reaction mixture was concentrated to afford a crude product (1.5 g) as a brownish gum, which was purified by silica gel (60-120 mesh) column chromatography eluting with 3% methanol in chloroform to afford methyl 3-{[(2-aminophenyl)carbamothioyl]amino}-3-(4-fluoro-3,5-dimethylphenyl)propanoate (0.8 g) as a brownish gum.

MS: m/z 376 (M+1).

Step 5: Preparation of methyl 3-[(1H-1,3-benzodiazol-2-yl)amino]-3-(4-fluoro-3,5-dimethylphenyl)propanoate

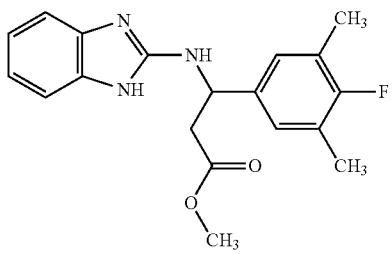

To a solution of afford methyl 3-{[(2-aminophenyl)carbamothioyl]amino}-3-(4-fluoro-3,5-dimethylphenyl)propanoate (from step 4)(0.4 g, 1 mmol) in methanol (25 mL) was added mercury(II)oxide (0.50 g, 2 mmol) and sulphur (0.007 g, 0.21 mmol) and the mixture was refluxed for 2 h. The reaction mixture was evaporated to give the crude product (0.38 g) which was purified by silica gel (60-120 mesh) column chromatography using 4% methanol in chloroform as eluent to afford methyl 3-[(1H-1,3-benzodiazol-2-yl)amino]-3-(4-fluoro-3,5-dimethylphenyl)propanoate (0.15 g) as an off-white solid.

$^1$H NMR (400 MHz, DMSO-$d_6$) δ 7.38 (dd, 2H, J=6.0, 3.2 Hz), 7.24-7.20 (m, 4H), 5.19 (dd, 1H, J=15.6, 7.2 Hz), 3.59 (s, 3H), 3.04 (d, 2H, J=7.2 Hz), 2.20 (d, 6H, J=1.6 Hz);

MS: m/z 342 (M+1).

Example 9, step 6: Preparation of 3-[(1H-1,3-benzodiazol-2-yl)amino]-3-(4-fluoro-3,5-dimethylphenyl)-N-methylpropanamide

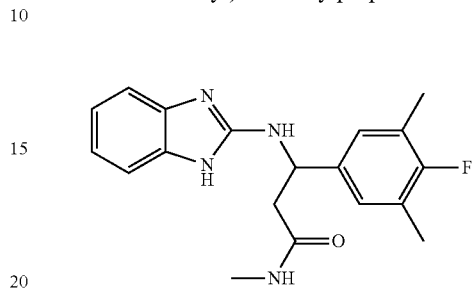

A solution of methyl 3-[(1H-1,3-benzodiazol-2-yl)amino]-3-(4-fluoro-3,5-dimethylphenyl)propanoate (from step 5) (0.075 g, 0.21 mmol) and methylamine (2 mL, 40% aqueous solution) in THF (10 mL) was stirred at ambient temperature for 2 h. The reaction mass was concentrated and was purified by silica gel (60-120 mesh) column chromatography using 5% methanol in chloroform as eluent to afford the desired product 3-[(1H-1,3-benzodiazol-2-yl)amino]-3-(4-fluoro-3,5-dimethylphenyl)-N-methylpropanamide (0.045 g) as an off-white solid.

$^1$H NMR (400 MHz, DMSO-$d_6$) δ 12.73 (bs, 1H, $D_2O$ exchangeable), 9.52 (d, 1H, J=8.8 Hz, $D_2O$ exchangeable), 7.95 (d, 1H, J=4.4 Hz, $D_2O$ exchangeable), 7.38 (dd, 2H, J=6.0, 3.2 Hz), 7.24 (t, 2H, 3.2 Hz), 7.17 (d, 2H, J=6.8 Hz), 5.20 (q, 1H, J=6.0 Hz), 3.11 (q, 1H, J=7.2, 4.8 Hz), 2.76 (t, 1H, J=7.6 Hz), 2.55 (d, 3H, J=4.4 Hz), 2.20 (s, 6H);

MS: m/z 341 (M+1).

Example 10: 3-[(1H-1,3-benzodiazol-2-yl)amino]-3-(4-chloro-3-methylphenyl)-N-methylpropanamide

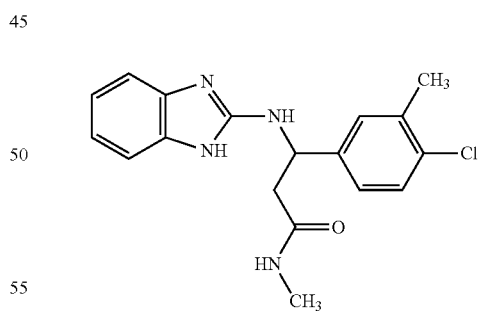

Starting with 4-chloro-3-methylbenzaldehyde, the procedures described in Example 9, steps 1 to 6 where applied to afford 3-[(1H-1,3-benzodiazol-2-yl)amino]-3-(4-chloro-3-methylphenyl)-N-methylpropanamide as an off-white solid.

$^1$H NMR (400 MHz, $CH_3OH$-$d_4$) δ 7.37 (s, 1H), 7.30 (d, 1H, J=8.12 Hz), 7.24 (d, 1H, J=8.36 Hz), 7.17 (d, 2H, J=3.40 Hz), 6.96 (q, 2H, J=4.00 Hz), 5.21 (t, 1H, J=6.80 Hz), 2.81-2.70 (m, 2H), 2.65 (s, 3H), 2.33 (s, 3H);

MS: m/z 343.2 (M+1).

Example 11: 3-[(1H-1,3-benzodiazol-2-yl)amino]-N-methoxy-N-methyl-3-[3-(trifluoromethyl)phenyl]propanamide

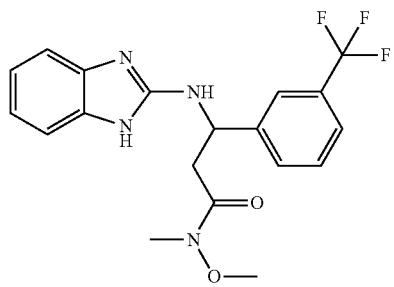 [SMILES: CON(C)C(=O)CC(Nc1nc2ccccc2[nH]1)c1cccc(C(F)(F)F)c1]

Step 1: Preparation of tert-butyl N-{2-[methoxy(methyl)carbamoyl]-1-[3-(trifluoromethyl)phenyl]ethyl}carbamate

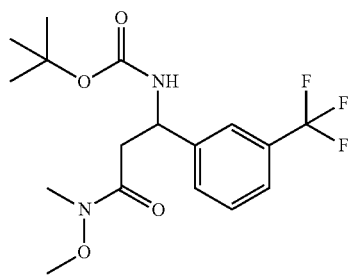 [SMILES: CON(C)C(=O)CC(NC(=O)OC(C)(C)C)c1cccc(C(F)(F)F)c1]

To a solution of 3-(tert-butoxycarbonylamino)-3-[3-(trifluoromethyl)phenyl]propanoic acid (0.5 g, 2 mmol) in DMF (10 mL) at 0° C. was added HBTU (0.68 g, 2 mmol) and DIEA (0.78 mL, d=0.74 g/mL, 5 mmol) followed by N-methoxymethanamine (0.11 g, 2 mmol) and stirred at ambient temperature for 16 h. The reaction mixture was poured into ice water (250 ml) and stirred for 2 h to form a precipitate. The precipitate thus formed was filtered and dried under vacuum to afford tert-butyl N-{2-[methoxy(methyl)carbamoyl]-1-[3-(trifluoromethyl)phenyl]ethyl}carbamate (0.35 g) as an off white solid.

$^1$H NMR (400 MHz, DMSO-$d_6$) δ 7.62-7.48 (m, 4H). 5.01 (d, 1H, J=6.9 Hz), 3.58 (s, 3H), 3.03 (s, 3H), 2.88 (dd, 1H, J=16.6, 9.36 Hz), 2.79 (d, 1H, J=10.4 Hz), 1.34 (s, 9H);
MS: m/z 377 (M+1);

Step 2: Preparation of 3-amino-N-methoxy-N-methyl-3-(3-(trifluoromethyl)phenyl)propanamide hydrochloride

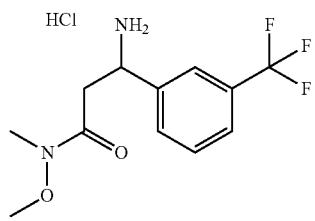 [SMILES: Cl ; CON(C)C(=O)CC(N)c1cccc(C(F)(F)F)c1]

To a solution of tert-butyl (3-(methoxy(methyl)amino)-3-oxo-1-(3-(trifluoromethyl)phenyl)propyl)carbamate (from step 1) (0.35 g, 0.92 mmol) in 1,4-dioxane (50 mL), was added 4.5 M HCl in 1,4-dioxane (10 mL) at 0° C. The reaction mixture was slowly warmed to ambient temperature and stirred for 16 h. The reaction mixture was filtered and dried to afford 3-amino-N-methoxy-N-methyl-3-(3-(trifluoromethyl)phenyl)propanamide hydrochloride (0.28 g) as an off-white solid.

$^1$H NMR (400 MHz, DMSO-$d_6$) δ 8.59 (bs, 2H), 7.96 (s, 1H), 7.86 (d, 1H, J=7.6 Hz), 7.76 (d, 1H, J=8 Hz), 7.66 (t, 1H, J=7.6 Hz), 4.76 (bs, 1H), 3.64 (s, 3H), 3.20 (dd, 2H, J=11.2, 6.4 Hz), 3.06 (s, 3H);
MS: m/z 277 (M+1).

Step 3: Preparation of 3-isothiocyanato-N-methoxy-N-methyl-3-(3-(trifluoromethyl)phenyl)propanamide

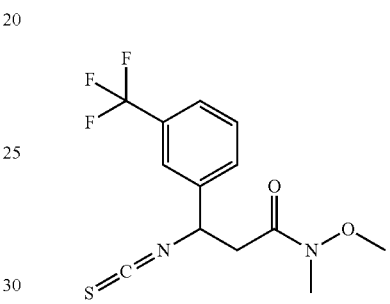

To a suspension of 3-amino-N-methoxy-N-methyl-3-(3-(trifluoromethyl)phenyl)propanamide hydrochloride (from step 2) (0.3 g, 0.95 mmol) in dichloromethane (10 mL) cooled at 0° C. was added thiophosgene (0.22 mL, d=1.5 g/mL, 2.87 mmol) followed by 10% aqueous sodium bicarbonate solution (10 mL). The reaction mixture was then stirred at ambient temperature. After 1 h, the reaction mixture was diluted with 10% aqueous sodium bicarbonate solution (25 mL) and extracted with dichloromethane (3×20 mL). The combined organic extracts were dried over anhydrous sodium sulphate and evaporated to dryness to afford 3-isothiocyanato-N-methoxy-N-methyl-3-(3-(trifluoromethyl)phenyl)propanamide (0.30 g) as a red gum.
MS: m/z 319 (M+1).

Step 4: Preparation of 3-{[(2-aminophenyl)carbamothioyl]amino}-N-methoxy-N-methyl-3-[3-(trifluoromethyl)phenyl]propanamide

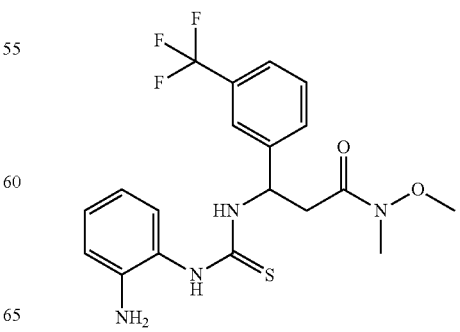

A mixture of 3-isothiocyanato-N-methoxy-N-methyl-3-(3-(trifluoromethyl)phenyl)propanamide (from step 3) (0.25 g, 0.78 mmol) and 1,2-phenylenediamine (0.085 g, 0.78 mmol) in dichloromethane (25 mL) was stirred at ambient temperature for 12 h. The reaction mixture was concentrated to afford a crude product (0.35 g) as a brownish gum, which was purified by silica gel (60-120 mesh) column chromatography eluting with 3% methanol in chloroform to afford 3-{[(2-aminophenyl)carbamothioyl]amino}-N-methoxy-N-methyl-3-[3-(trifluoromethyl)phenyl]propanamide (0.1 g) as a brownish gum.

MS: m/z 427 (M+1).

Example 11, step 5: 3-[(1H-1,3-benzodiazol-2-yl)amino]-N-methoxy-N-methyl-3-[3-(trifluoromethyl)phenyl]propanamide

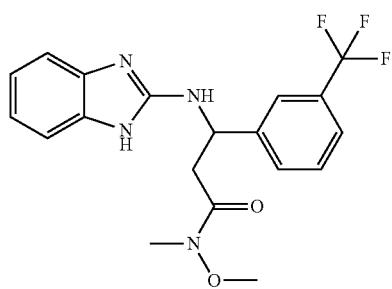 [SMILES: CON(C)C(=O)CC(Nc1nc2ccccc2[nH]1)c1cccc(C(F)(F)F)c1]

To a solution of 3-{[(2-aminophenyl)carbamothioyl]amino}-N-methoxy-N-methyl-3-[3-(trifluoromethyl)phenyl]propanamide (from step 4) (0.4 g, 0.93 mmol) in methanol (25 mL) was added mercury(II)oxide (0.49 g, 1.8 mmol) and sulphur (0.006 g, 0.18 mmol) and the mixture was refluxed for 2 h. The reaction mixture was evaporated to afford the crude product (0.12 g) which was purified by silica gel (60-120 mesh) column chromatography using 4% methanol in chloroform as eluent to afford 3-[(1H-1,3-benzodiazol-2-yl)amino]-N-methoxy-N-methyl-3-[3-(trifluoromethyl)phenyl]propanamide (0.02 g) as brown solid.

$^1$H NMR (400 MHz, DMSO-$d_6$) δ 11.09 (bs, 1H, $D_2O$ exchangeable), 7.83 (s, 1H), 7.76 (d, 1H, J=6.8 Hz), 7.55 (dd, 2H, J=16.0, 8.9 Hz), 7.53 (bs, 1H, $D_2O$ exchangeable), 7.11 (dd, 2H, J=5.7, 3.3 Hz), 6.87 (dd, 2H, J=5.8, 3.2 Hz), 5.40 (dd, 1H, J=14.4, 7.6 Hz), 3.62 (s, 3H), 3.14 (dd, 1H, J=14.8, 6.8 Hz), 3.04 (s, 3H), 3.94 (dd, 1H, J=16.4, 5.2 Hz);

MS: m/z 393 (M+1).

Example 12: Preparation of 3-[(1H-1,3-benzodiazol-2-yl)amino]-N-methyl-3-[3-(methylsulfanyl)phenyl]propanamide

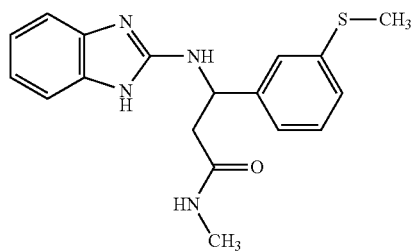 [SMILES: CNC(=O)CC(Nc1nc2ccccc2[nH]1)c1cccc(SC)c1]

Step 1: Preparation of N-methoxy-N-methyl-3-(methylthio)benzamide

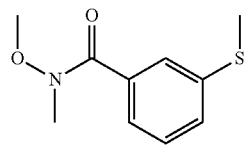

To a suspension of 3-(methylthio)benzoic acid (2 g, 11.88 mmol) in DMF (20 mL) at 0° C. was added N,O-dimethylhydroxylamine (1.45 g, 23.77 mmol), HOBT (2.18 g, 14.26 mmol), EDC.HCl (2.73 g, 14.26 mmol) and triethylamine (2.40 g, 23.77 mmol). The reaction mixture was then stirred at ambient temperature. After 12 h, the reaction mixture was diluted with 10% aqueous sodium bicarbonate solution (50 mL) and extracted with dichloromethane (3×50 mL). The combined organic extract were dried over anhydrous sodium sulphate and evaporated to dryness to afford N-methoxy-N-methyl-3-(methylthio)benzamide (2.1 g) as an off-white solid.

$^1$H NMR (400 MHz, CDCl$_3$) δ 7.54 (s, 1H), 7.43 (t, 1H, J=1.6 Hz), 7.35-7.27 (m, 2H), 3.56 (s, 3H), 3.36 (s, 3H), 2.50 (s, 3H);

MS: m/z 212.2 (M+1).

Step 2: Preparation of 3-(methylthio)benzaldehyde

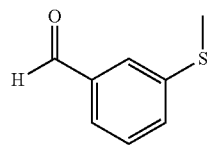

To a suspension of afford N-methoxy-N-methyl-3-(methylthio)benzamide (from step 1) (5 g, 23 mmol) in THF (50 mL) at −78° C. was added DIBAL-H (47 mL, 1M in toluene solution, 47 mmol). The reaction mixture was then stirred at ambient temperature. After 12 h, the reaction mixture was diluted with 10% aqueous sodium bicarbonate solution (250 mL) and extracted with dichloromethane (3×250 mL). The combined organic extract was dried over anhydrous sodium sulphate and evaporated to dryness to afford 3-(methylthio)benzaldehyde (3.5 g) as an off-white solid.

$^1$H NMR (400 MHz, CDCl$_3$) δ 9.99 (s, 1H), 7.74 (t, 1H, J=1.6 Hz), 7.64-7.62 (m, 1H), 7.52-7.43 (m, 2H), 2.55 (s, 3H);

MS: m/z 153.03 (M+1).

Example 12, Steps 3 to 8: Preparation of 3-[(1H-1,3-benzodiazol-2-yl)amino]-N-methyl-3-[3-(methylsulfanyl)phenyl]propanamide

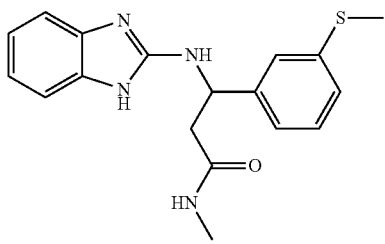 [SMILES: CNC(=O)CC(Nc1nc2ccccc2[nH]1)c1cccc(SC)c1]

The product of step 2 was used in the procedures described for Example 9 steps 1 to 6 to afford 3-[(1H-1,3-benzodiazol-2-yl)amino]-N-methyl-3-[3-(methylsulfanyl)phenyl]propanamide as an off-white solid.

$^1$H NMR (400 MHz, DMSO-$d_6$) δ 10.78 (s, 1H), 7.80 (d, 1H, J=5.12, Hz), 7.32 (s, 1H), 7.25-7.21 (m, 2H), 7.17 (d, 1H, J=7.52 Hz), 7.08 (d, 3H, J=7.4 Hz), 6.87-6.78 (m, 2H), 5.22 (q, 1H, J=8.12 Hz), 2.67-2.58 (m, 5H), 2.44 (s, 3H);

MS: m/z 341.0 (M+1).

Example 13: Preparation of 3-[(1H-1,3-benzodiazol-2-yl)amino]-N-methyl-3-[3-(trifluoromethoxy)phenyl]propanamide

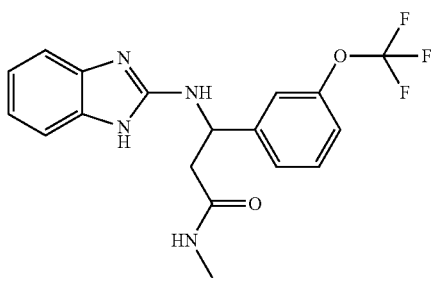 [SMILES: CNC(=O)CC(Nc1nc2ccccc2[nH]1)c1cccc(OC(F)(F)F)c1]

Starting with 3-(trifluoromethoxy)benzaldehyde, the procedures described in Example 9, steps 1 to 6, where applied to afford 3-[(1H-1,3-benzodiazol-2-yl)amino]-N-methyl-3-[3-(trifluoromethoxy)phenyl]propanamide as an off-white solid.

$^1$H NMR (400 MHz, MeOH-$d_4$) δ 7.48-7.45 (m, 2H), 7.38 (s, 1H), 7.21-7.16 (m, 3H), 7.01-6.97 (m, 2H), 5.32 (t, 1H, J=6.8 Hz), 2.79 (q, 2H, J=2.80 Hz), 2.66 (s, 3H);

MS: m/z 379.0 (M+1).

Example 14: Preparation of 3-[(5-fluoro-4-methyl-1H-1,3-benzodiazol-2-yl)amino]-3-[3-(trifluoromethyl)phenyl]propanamide

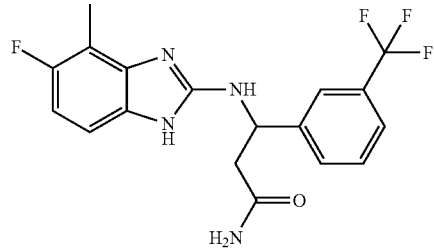 [SMILES: Cc1c(F)ccc2[nH]c(NC(CC(N)=O)c3cccc(C(F)(F)F)c3)nc12]

Step 1: Preparation of methyl 3-{[(6-amino-3-fluoro-2-methylphenyl)carbamothioyl]amino}-3-[3-(trifluoromethyl)phenyl]propanoate

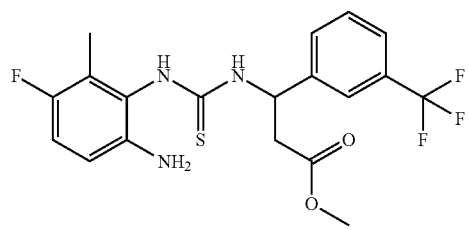 [SMILES: COC(=O)CC(NC(=S)Nc1c(N)ccc(F)c1C)c1cccc(C(F)(F)F)c1]

A mixture of methyl 3-isothiocyanato-3-[3-(trifluoromethyl)phenyl]propanoate (from Example 2, step 1) (0.35 g, 0.12 mmol) and 4-fluoro-3-methylbenzene-1,2-diamine (0.17 g, 0.12 mmol) in dichloromethane (3.5 mL) was stirred at ambient temperature for 12 h. The reaction mixture was concentrated to give a crude product (0.45 g) as a brownish gum, which was purified by silica gel (60-120 mesh) column chromatography eluting with 7% methanol in chloroform to afford methyl 3-{[(6-amino-3-fluoro-2-methylphenyl)carbamothioyl]amino}-3-[3-(trifluoromethyl)phenyl]propanoate (0.32 g) as a brownish gum.

MS: m/z 430 (M+1).

Step 2: Preparation of methyl 3-[(6-fluoro-7-methyl-1H-1,3-benzodiazol-2-yl)amino]-3-[3-(trifluoromethyl)phenyl]propanoate

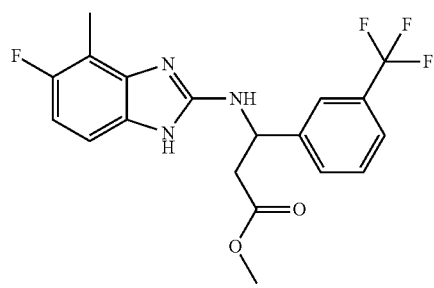 [SMILES: COC(=O)CC(Nc1nc2c(C)c(F)ccc2[nH]1)c1cccc(C(F)(F)F)c1]

To a solution of methyl 3-{[(6-amino-3-fluoro-2-methylphenyl)carbamothioyl]amino}-3-[3-(trifluoromethyl)phenyl]propanoate (from Step 1) (0.4 g, 0.093 mmol) in methanol (4 mL) was added iodoacetic acid (0.173 g, 0.0934 mmol) and the mixture was refluxed for 2 h. The reaction mixture was evaporated to give the crude product (0.4 g) which was purified by silica gel (60-120 mesh) column chromatography using 4% methanol in chloroform as eluent to afford methyl 3-[(6-fluoro-7-methyl-1H-1,3-benzodiazol-2-yl)amino]-3-[3-(trifluoromethyl)phenyl]propanoate (0.25 g) as an off-white solid.

$^1$H NMR (400 MHz, AcOH-d$_4$) δ 7.83 (d, 2H, J=11.92 Hz), 7.67-7.58 (m, 2H), 7.21-7.18 (m, 1H), 6.98 (t, 1H, J=10.04 Hz), 5.46 (t, 1H, J=7.68 Hz), 3.69 (s, 3H), 3.30 (dd, 1H, J=16.92, 8.4 Hz), 3.13 (dd, 1H, J=16.96, 5.56 Hz), 2.37 (s, 3H);

MS: m/z 396.1 (M+1).

Example 14, step 3: Preparation of 3-[(5-fluoro-4-methyl-1H-1,3-benzodiazol-2-yl)amino]-3-[3-(trifluoromethyl)phenyl]propanamide

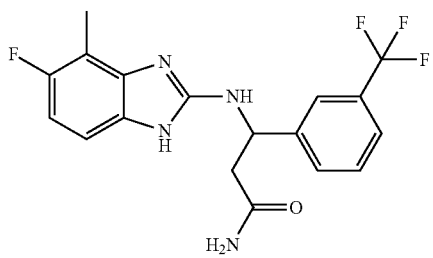 [SMILES: Cc1c(F)ccc2[nH]c(NC(CC(N)=O)c3cccc(C(F)(F)F)c3)nc12]

To a solution of methyl 3-[(6-fluoro-7-methyl-1H-1,3-benzodiazol-2-yl)amino]-3-[3-(trifluoromethyl)phenyl]propanoate (from step 2), (0.1 g, 0.025 mmol) in acetonitrile (4 mL) was added aqueous ammonia (0.089 g, 0.003 mmol) in a sealed tube and the reaction mixture was stirred at ambient temperature. After 12 h, the reaction mixture was diluted with water (10 mL) and extracted with dichloromethane (3×10 mL). The combined organic extracts were dried over anhydrous sodium sulphate and evaporated to give the crude product (0.1 g), which was purified by silica gel (60-120 mesh) column chromatography using 5% methanol in chloroform as eluent to afford 3[(5-fluoro-4-methyl-1H-1,3-benzodiazol-2-yl)amino]-3-[3-(trifluoromethyl)phenyl]propanamide (0.06 g) as an off-white solid.

$^1$H NMR (400 MHz, DMSO-d$_6$ & D$_2$O) δ 7.84-7.74 (m, 1H), 7.56-7.53 (m, 2H), 7.40 (s, 1H), 6.89-6.84 (m, 1H), 6.61-6.56 (m, 1H), 5.32 (br. s, 1H), 2.75-2.60 (m, 2H), 2.23 (s, 3H);

MS: m/z 381.1 (M+1).

Example 15: Preparation of 2-[(1H-1,3-benzodiazol-2-yl)amino]-N-(2-methylpropyl)-2-[3-(trifluoromethyl)phenyl]acetamide

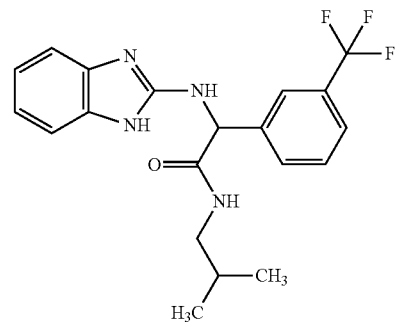 [SMILES: CC(C)CNC(=O)C(Nc1nc2ccccc2[nH]1)c1cccc(C(F)(F)F)c1]

A mixture of methyl 2-[(1H-1,3-benzodiazol-2-yl)amino]-2-[3-(trifluoromethyl)phenyl]acetate (from Example 1, step 2) (350 mg, 1 mmol) and isobutylamine (220 mg, 3 mmol) in acetonitrile (5 mL) was irradiated in a microwave oven at 130° C. for 3 h. The crude mixture was purified by preparative HPLC to afford 2-[(1H-1,3-benzodiazol-2-yl)amino]-N-(2-methylpropyl)-2-[3-(trifluoromethyl)phenyl]acetamide (70 mg) as an off-white solid.

$^1$H NMR (400 MHz, DMSO-d$_6$) δ 10.48 (s, 1H), 8.54 (t, 1H, J=5.24 Hz), 7.92 (s, 1H), 7.82 (d, 1H, J=7.32 Hz), 7.66-7.58 (m, 2H), 7.48 (d, 1H, J=7.16 Hz), 7.18 (d, 1H, J=7.16 Hz), 7.12 (d, 1H, J=7.04 Hz), 6.87 (t, 2H, J=8.16 Hz), 5.73 (d, 1H, J=8.56 Hz), 3.02-2.95 (m, 1H), 2.89-2.82 (m, 1H), 1.68-1.61 (m, 1H), 0.75 (d, 6H, J=6.60 Hz);

MS: m/z 391.2 (M+1).

Example 16: Preparation of 2-[(1H-1,3-benzodiazol-2-yl)amino]-N-cyclopropyl-2-[3-(trifluoromethyl)phenyl]acetamide

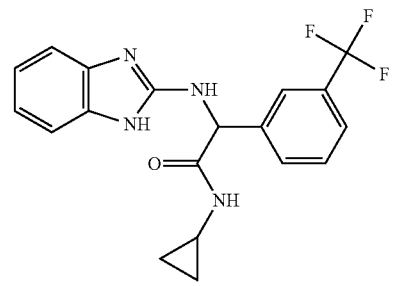 [SMILES: O=C(NC1CC1)C(Nc1nc2ccccc2[nH]1)c1cccc(C(F)(F)F)c1]

A mixture of methyl 2-[(1H-1,3-benzodiazol-2-yl)amino]-2-[3-(trifluoromethyl)phenyl]acetate (from Example 1, step 2) (250 mg, 0.72 mmol) and cyclopropylamine (49 mg, 0.86 mmol) in acetonitrile (3 mL) was irradiated in a microwave oven at 130° C. for 3 h. The crude product was purified by silica gel (60-120 mesh) column chromatography eluting with 4% methanol in chloroform to afford 2-[(1H-1,3-benzodiazol-2-yl)amino]-N-cyclopropyl-2-[3-(trifluoromethyl)phenyl]acetamide (135 mg) as an off-white solid.

$^1$H NMR (400 MHz, DMSO-d$_6$) δ 10.46 (s, 1H), 8.64 (d, 1H, J=4.16 Hz), 7.85 (s, 1H), 7.78 (d, 1H, J=7.60 Hz), 7.66-7.58 (m, 2H), 7.50 (d, 1H, J=8.68 Hz), 7.18 (d, 1H, J=6.84 Hz), 7.11 (d, 1H, J=7.28 Hz), 6.87 (t, 2H, J=8.56 Hz), 5.63 (d, 1H, J=8.68 Hz), 2.67-2.63 (m, 1H), 0.67-0.59 (m, 2H), 0.46-0.43 (m, 1H), 0.34-0.30 (m, 1H);

MS: m/z 375.2 (M+1).

Example 17: 3-[(5-fluoro-1H-1,3-benzodiazol-2-yl)amino]-N-methyl-3-[3-(trifluoromethyl)phenyl]propanamide

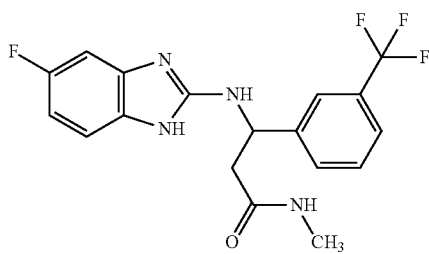 [SMILES: CNC(=O)CC(Nc1nc2cc(F)ccc2[nH]1)c1cccc(C(F)(F)F)c1]

The procedures described in Example 2, steps 2 to 4 where applied with 4-fluoro-benzene-1,2-diamine to afford 3-[(5-fluoro-1H-1,3-benzodiazol-2-yl)amino]-N-methyl-3-[3-(trifluoromethyl)phenyl]propanamide as an off-white solid.

¹H NMR (400 MHz, AcOH-d₄) δ 7.84 (s, 1H), 7.78 (d, 1H, J=7.60 Hz), 7.65 (d, 1H, J=8.00 Hz), 7.58 (t, 1H, J=7.60 Hz), 7.36 (dd, 1H, J=4.40, 8.80 Hz), 7.19 (d, 1H, J=8.40 Hz), 6.99 (dt, 1H, J=2.40, 12.80 Hz), 5.54 (q, 1H, J=5.20 Hz), 3.13 (dd, 1H, J=9.60, 14.80 Hz), 2.97 (dd, 1H, J=4.80, 14.60 Hz), 2.74 (s, 3H); MS: m/z 381.2 (M+1).

Example 18: N-methyl-3-{[5-(trifluoromethoxy)-1H-1,3-benzodiazol-2-yl]amino}-3-[3-(trifluoromethyl)phenyl]propanamide; trifluoroacetic acid

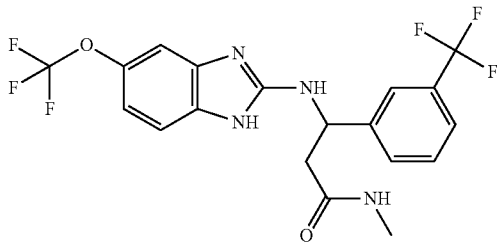

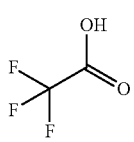

Step 1: Preparation of tert-butyl N-[2-(methylcarbamoyl)-1-[3-(trifluoromethyl)phenyl]ethyl]carbamate

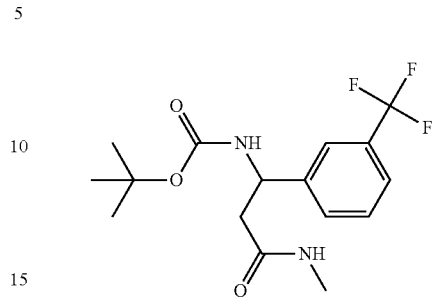

To a solution of methyl 3-{[(tert-butoxy)carbonyl]amino}-3-[3-(trifluoromethyl)phenyl]propanoate (1.0 g, 3 mmol) in acetonitrile (20 mL), was added 40% methylamine in water (15 mL) at 0° C. and then warmed and stirred at ambient temperature. After 16 h, the reaction mixture was extracted with chloroform (2×100 mL) and washed with brine, dried over anhydrous sodium sulphate, filtered and concentrated to afford the crude product as a white solid. The crude was purified by 'GRACE' using 6% methanol in chloroform as an eluent to afford tert-butyl N-[2-(methylcarbamoyl)-1-[3-(trifluoromethyl)phenyl]ethyl]carbamate (0.95 g) as an off-white solid.

¹H NMR (400 MHz, DMSO-d₆ & D₂O) δ 7.61-7.56 (m, 4H), 4.99 (d, 1H, J=7.48 Hz), 2.80 (q, 2H, J=3.88 Hz), 2.49 (s, 3H), 1.36 (s, 9H);

MS: m/z 346 (M+).

Step 2: Preparation of 3-amino-N-methyl-3-[3-(trifluoromethyl)phenyl]propanamide; trifluoroacetic acid

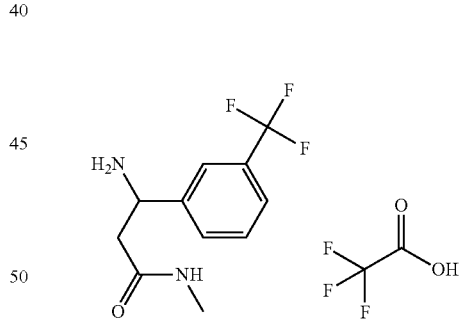

To a solution of tert-butyl N-[2-(methylcarbamoyl)-1-[3-(trifluoromethyl)phenyl]ethyl]carbamate (0.95 g, 3 mmol) (from step 1) in dichloromethane (25 mL), was added trifluoroacetic acid (1.87 g, 16 mmol) and stirred at ambient temperature. After 16 h, the reaction mixture was concentrated to afford 3-amino-N-methyl-3-[3-(trifluoromethyl)phenyl]propanamide; trifluoroacetic acid (1.2 g) as a reddish gum.

1H NMR (400 MHz, DMSO-d6 & D2O) δ 7.83 (s, 1H), 7.74 (d, 2H, J=7.52 Hz), 7.67 (t, 1H, J=7.80 Hz), 4.77 (d, 1H, J=5.64 Hz), 2.80 (q, 2H, J=3.88 Hz), 2.52 (s, 3H);

MS: m/z 246 (M+).

Step 3: Preparation of 3-isothiocyanato-N-methyl-3-[3-(trifluoromethyl)phenyl]propanamide

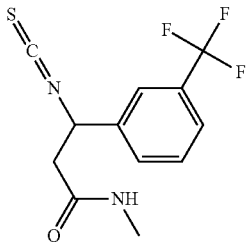 [SMILES: CNC(=O)CC(N=C=S)c1cccc(C(F)(F)F)c1]

To a stirred solution of 3-amino-N-methyl-3-[3-(trifluoromethyl)phenyl]propanamide; trifluoroacetic acid (1.2 g, 3 mmol) (from step 2) in dichloromethane (30 mL) was added thiophosgene (0.957 g, 8 mmol) and then a saturated solution of sodium bicarbonate (20 mL) was added at 0° C. The mixture was slowly warmed to ambient temperature. After 3 h, the above reaction mixture was diluted with a saturated aqueous solution of sodium bicarbonate (30 mL). The aqueous layer was extracted with dichloromethane (3×50 mL). The combined organic layer was washed with brine (25 mL), dried over anhydrous sodium sulphate, filtered and concentrated to afford 3-isothiocyanato-N-methyl-3-[3-(trifluoromethyl)phenyl]propanamide (0.95 g) as an off-white solid.

$^1$H NMR (400 MHz, DMSO-$d_6$) δ 8.01 (s, 1H), 7.78-7.68 (m, 4H), 5.61 (q, 1H, J=4.88 Hz), 2.88 (q, 1H, J=9.52 Hz), 2.73 (q, 1H, J=8.16 Hz), 2.60 (s, 3H);
MS: m/z 288 (M+).

Step 4: Preparation of 3-({-[2-amino-5-(trifluoromethoxy)phenyl]carbamothioyl}amino)-N-methyl-3-[3-(trifluoromethyl)phenyl]propanamide

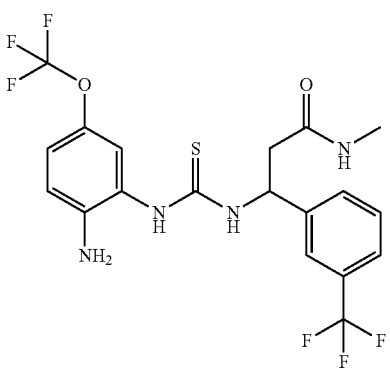 [SMILES: CNC(=O)CC(NC(=S)Nc1cc(OC(F)(F)F)ccc1N)c1cccc(C(F)(F)F)c1]

A mixture of 3-isothiocyanato-N-methyl-3-[3-(trifluoromethyl)phenyl]propanamide (0.3 g, 1 mmol) (from step 3) and 4-(trifluoromethoxy)benzene-1,2-diamine (0.2 g, 1 mmol) in dichloromethane (100 mL) was stirred at ambient temperature. After 4 h, the reaction mixture was concentrated to afford the crude product (0.50 g) as yellow gum. It was purified by flash column using 230-400 silica gel, the product fraction was eluted using 40% ethyl acetate in hexane to afford 3-({[2-amino-5-(trifluoromethoxy)phenyl]carbamothioyl}amino)-N-methyl-3-[3-(trifluoromethyl)phenyl]propanamide (0.4 g) as an off-white solid.
MS: m/z 481 (M+1).

Example 18, step 5: Preparation of N-methyl-3-{[5-(trifluoromethoxy)-1H-1,3-benzodiazol-2-yl]amino}-3-[3-(trifluoromethyl)phenyl]propanamide; trifluoroacetic acid

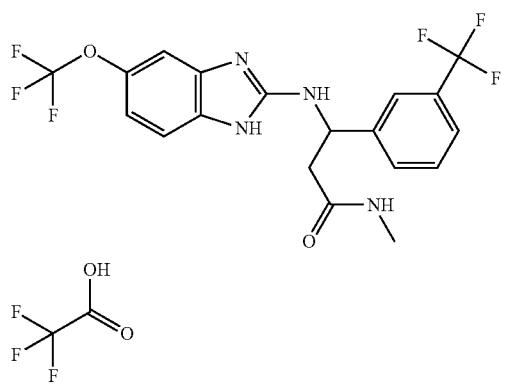

To a stirred solution of 3-({[2-amino-5-(trifluoromethoxy)phenyl]carbamothioyl}amino)-N-methyl-3-[3-(trifluoromethyl)phenyl]propanamide (0.2 g, 0.43 mmol) (from step 4) in methanol (10 mL) was added iodoacetic acid (0.093 g, 0.5 mmol) and heated at 65° C. After 4 h, the reaction mixture was evaporated and the residue was dissolved in ethyl acetate, washed with 10% aqueous sodium bicarbonate solution (30 mL). The organic extracts were dried over anhydrous sodium sulphate and evaporated to afford the crude product (0.15 g) as a yellow gum. This was purified by preparative HPLC and the desired fractions were concentrated to afford N-methyl-3-{[5-(trifluoromethoxy)-1H-1,3-benzodiazol-2-yl]amino}-3-[3-(trifluoromethyl)phenyl]propanamide; trifluoroacetic acid (30.0 mg) as a yellow solid.

$^1$H NMR (400 MHz, AcOH-$d_4$) δ 7.86 (s, 1H), 7.80 (d, 1H, J=7.40 Hz), 7.67 (d, 1H, J=7.56 Hz), 7.60 (t, 1H, J=7.80 Hz), 7.48 (d, 1H, J=8.60 Hz), 7.41 (s, 1H), 7.21 (d, 1H, J=8.52 Hz), 5.59 (q, 1H, J=4.84 Hz), 3.17 (dd, 1H, J=9.44, 15.04 Hz), 3.02 (dd, 1H, J=4.92, 15.00 Hz), 2.75 (s, 3H); MS: m/z 447 (M+1).

Example 19: Preparation of 3-{[4-(methoxymethyl)-1H-1,3-benzodiazol-2-yl]amino}-N-methyl-3-[3-(trifluoromethyl)phenyl]propanamide

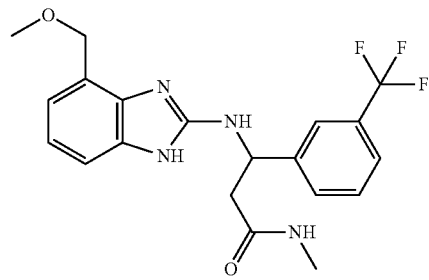 [SMILES: CNC(=O)CC(Nc1nc2c(COC)cccc2[nH]1)c1cccc(C(F)(F)F)c1]

Step 1: Preparation of 4-(methoxymethyl)-2,1,3-benzothiadiazole

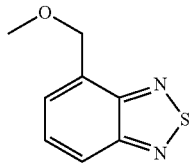

To a stirred solution of 4-(bromomethyl)-2,1,3-benzothiadiazole (4.5 g, 20 mmol) in tetrahydrofuran was added 25% sodium methoxide in methanol (2.12 g, 39 mmol) at 0° C. This reaction mass was slowly warmed to ambient temperature. After 12 h, the reaction mixture was quenched with ice cold water and then diluted with a saturated aqueous solution of NaHCO$_3$ (20 mL). The aqueous layer was extracted with EtOAc (3×50 mL) and the combined organic layer was washed with brine (20 mL), dried over anhydrous sodium sulphate, filtered and concentrated to afford 4-(methoxymethyl)-2,1,3-benzothiadiazole (3.5 g) as a yellow gum.

$^1$H NMR (400 MHz, CDCl$_3$) δ 7.98-7.93 (m, 1H), 7.66-7.59 (m, 2H), 5.02 (s, 2H), 3.57 (s, 3H);

MS: m/z 181 (M+1).

Step 2: Preparation of 3-(methoxymethyl)benzene-1, 2-diamine

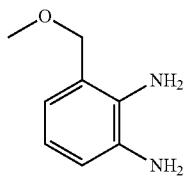

To a stirred solution of 4-(methoxymethyl)-2,1,3-benzothiadiazole (4 g, 22 mmol) (from step 1) in methanol (50 mL) was added raney nickel (100% w/w, washed five times with methanol) and it was hydrogenated under a balloon pressure of hydrogen gas at ambient temperature. The reaction mixture was filtered through a celite bed and the residue was washed with methanol (5×100 mL). The combined filtrate was concentrated to afford 3-(methoxymethyl)benzene-1, 2-diamine (2.5 g) as blue gum.

$^1$H NMR (400 MHz, DMSO-d$_6$ & D$_2$O) δ 7.15 (d, 1H, J=7.76 Hz), 7.09 (d, 1H, J=7.16 Hz), 6.71 (t, 1H, J=7.64 Hz), 4.40 (s, 2H), 3.27 (s, 3H);

MS: m/z 153 (M+1).

Step 3: Preparation of methyl 3-({[2-amino-6-(methoxymethyl)phenyl]carbamothioyl}amino)-3-[3-(trifluoromethyl)phenyl]propanoate

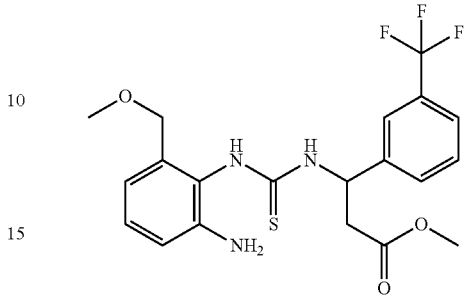

A mixture of 3-(methoxymethyl)benzene-1, 2-diamine (2.0 g, 13 mmol) (from step 2) and methyl 3-isothiocyanato-3-[3-(trifluoromethyl)phenyl]propanoate (4.5 g, 16 mmol) (from Example 2, step-1) in dichloromethane (50 mL) was stirred at ambient temperature. The reaction mixture was concentrated to afford the crude product (3.0 g) as a brownish gum. It was purified by column chromatography (230-400 mesh silica gel), the product fraction was eluted using 30% ethyl acetate in hexane to afford 3-({[2-amino-6-(methoxymethyl)phenyl]carbamothioyl}amino)-3-[3-(trifluoromethyl)phenyl]propanoate (2.5 g) as a brownish gum.

MS: m/z 442 (M+1).

Step 4: Preparation of methyl 3-{[4-(methoxymethyl)-1H-1,3-benzodiazol-2-yl]amino}-3-[3-(trifluoromethyl)phenyl]propanoate

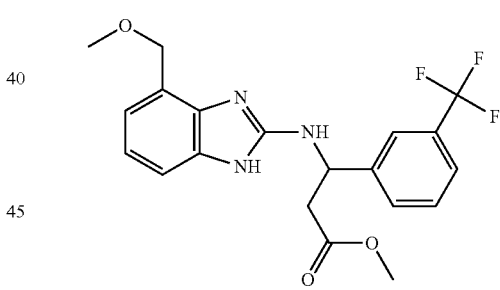

To a stirred solution of 3-({[2-amino-6-(methoxymethyl)phenyl]carbamothioyl}amino)-3-[3-(trifluoromethyl)phenyl]propanoate (4 g, 9 mmol) (from step 3) in methanol (50 mL) was added iodoacetic acid (4.2 g, 23 mmol) and heated at 65° C. After 16 h, reaction mixture was concentrated to afford a crude product (2.5 g) as a yellowish gum. It was purified by grace column using 80% ethyl acetate in hexane to afford the desired product (2.2 g) as yellow solid. 0.2 g of the compound was purified by preparative thin layer chromatography (TLC). The solid was dissolved in methanol and filtered and the filtrate was concentrated to methyl 3-{[4-(methoxymethyl)-1H-1,3-benzodiazol-2-yl]amino}-3-[3-(trifluoromethyl)phenyl]propanoate (0.1 g) as white solid.

$^1$H NMR (400 MHz, DMSO-d$_6$ & D$_2$O) δ 7.88 (s, 1H), 7.80 (d, 1H, J=7.20 Hz), 7.60 (q, 2H, J=7.60 Hz), 7.12 (s, 1H), 6.92 (s, 2H), 5.43 (s, 1H), 4.59 (q, 2H, J=12.40 Hz), 3.63 (s, 3H), 3.29 (s, 3H), 3.11-3.01 (m, 2H);

MS: m/z 408 (M+1).

Example 19, step 5: Preparation of 3-{[4-(methoxymethyl)-1H-1,3-benzodiazol-2-yl]amino}-N-methyl-3-[3-(trifluoromethyl)phenyl]propanamide

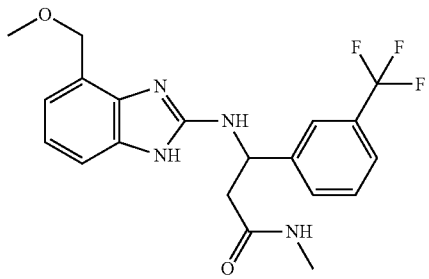 [SMILES: CNC(=O)CC(Nc1nc2c(COC)cccc2[nH]1)c1cccc(C(F)(F)F)c1]

To a stirred solution of methyl 3-{[4-(methoxymethyl)-1H-1,3-benzodiazol-2-yl]amino}-3-[3-(trifluoromethyl)phenyl]propanoate (0.3 g, 0.7 mmol) (from step 4) in tetrahydrofuran (5 mL) was added 40% aqueous methylamine (20 mL) and stirred at ambient temperature. The reaction mixture was concentrated to afford the crude product (0.15 g) as a colourless gum. It was basified using 10% aqueous NaHCO₃ solution (20 mL) and extracted with ethyl acetate (3×100 mL), dried over anhydroud Na₂SO₄, filtered and concentrated to afford the desired product (0.1 g) as a white solid. 0.09 g of the compound was purified by preparative TLC. The solid was dissolved in methanol and filtered and the filtrate was concentrated to afford 3-{[4-(methoxymethyl)-1H-1,3-benzodiazol-2-yl]amino}-N-methyl-3-[3-(trifluoromethyl)phenyl]propanamide (0.08 g) as a white solid.

$^1$H NMR (400 MHz, AcOH-d$_4$) δ 7.85 (s, 1H), 7.81 (d, 1H, J=7.64 Hz), 7.65 (d, 1H, J=7.44 Hz), 7.59 (t, 1H, J=7.72 Hz), 7.39 (d, 1H, J=7.52 Hz), 7.24 (t, 1H, J=7.72 Hz), 7.19 (d, 1H, J=7.52 Hz), 5.68 (s, 1H), 4.75 (d, 2H, J=13.12 Hz), 3.43 (s, 3H), 3.13 (dd, 1H, J=9.08, 14.90 Hz), 3.01 (dd, 1H, J=5.12, 14.42 Hz), 2.74 (s, 3H);

MS: m/z 407 (M+1).

Example 20: Preparation of 3-[(4-chloro-1H-1,3-benzodiazol-2-yl)amino]-N-methyl-3-[3-(trifluoromethyl)phenyl]propanamide

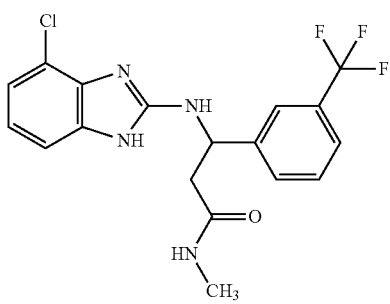 [SMILES: CNC(=O)CC(Nc1nc2c(Cl)cccc2[nH]1)c1cccc(C(F)(F)F)c1]

The procedures described in Example 2, steps 2 to 4 where applied with 3-chloro-benzene-1,2-diamine to afford 3-[(4-chloro-1H-1,3-benzodiazol-2-yl)amino]-N-methyl-3-[3-(trifluoromethyl)phenyl]propanamide as an off-white solid.

$^1$H NMR (400 MHz, AcOH-d$_4$) δ 7.83 (s, 1H), 7.78 (d, 1H, J=7.6 Hz), 7.64 (d, 1H, J=8.0 Hz), 7.58 (t, 1H, J=8.0 Hz), 7.35 (d, 1H, J=7.6 Hz), 7.25-7.18 (m, 2H), 5.70 (dd, 1H, J=8.8, 4.4 Hz), 3.11 (dd, 1H, J=14.8, 9.6 Hz), 2.97 (dd, 1H, J=14.8, 5.2 Hz), 2.74 (s, 3H);

MS: m/z 397 (M+1).

Example 21: Preparation of 3-{[4-(hydroxymethyl)-1H-1,3-benzodiazol-2-yl]amino}-N-methyl-3-{3-[(trifluoromethyl)sulfanyl]phenyl}propanamide

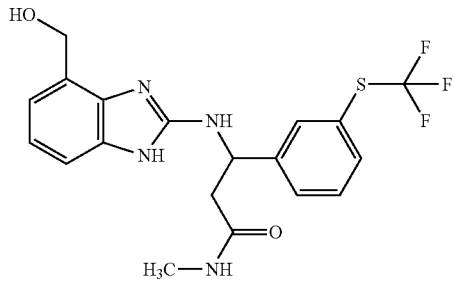 [SMILES: CNC(=O)CC(Nc1nc2c(CO)cccc2[nH]1)c1cccc(SC(F)(F)F)c1]

Step 1: Preparation of 3-amino-3-{3-[(trifluoromethyl)sulfanyl]phenyl}propanoic acid

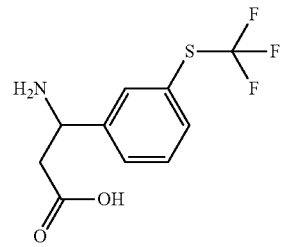 [SMILES: NC(CC(=O)O)c1cccc(SC(F)(F)F)c1]

A mixture of malonic acid (1 g, 10 mmol), ammonium formate (1.2 g, 19 mmol) and 3-((trifluoromethyl)thio)benzaldehyde (2 g, 10 mmol) in ethanol (10 mL) was refluxed for 12 h. The reaction mixture was evaporated to remove ethanol and the residue was triturated with acetone (2×50 mL). The solid was filtered and dried to afford 3-amino-3-{3-[(trifluoromethyl)sulfanyl]phenyl}propanoic acid (1.3 g) as a white solid.

$^1$H NMR (400 MHz, DMSO-d$_6$) δ 7.74 (s, 1H), 7.61 (dd, 2H, J=7.6, 13.6 Hz), 7.50 (t, 1H, J=7.6 Hz), 4.30 (bs, 1H), 2.36 (t, 2H, J=1.6 Hz);

MS: m/z 266.04 (M+1).

Step 2: Preparation of methyl 3-amino-3-{3-[(trifluoromethyl)sulfanyl]phenyl}propanoate hydrochloride

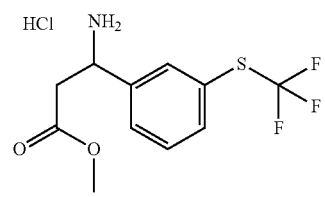 [SMILES: COC(=O)CC(N)c1cccc(SC(F)(F)F)c1 ; Cl]

To a suspension of 3-amino-3-{3-[(trifluoromethyl)sulfanyl]phenyl}propanoic acid (from step 1) (1.3 g, 4.9 mmol) in methanol (15 mL) cooled to 0° C. was added thionyl chloride (0.9 mL, 12.2 mmol) and the mixture was then warmed to ambient temperature and refluxed for 12 h. The reaction mixture was evaporated to dryness to afford methyl 3-amino-3-{3-[(trifluoromethyl)sulfanyl]
phenyl}propanoate hydrochloride (1.3 g) as an off-white solid.

$^1$H NMR (400 MHz, DMSO-$d_6$) δ 8.78 (br.s, 3H), 7.93 (s, 1H), 7.82 (d, 1H, J=7.76 Hz), 7.75 (d, 1H, J=7.84 Hz), 7.61 (t, 1H, J=7.8 Hz), 4.71 (q, 1H, J=6.2 Hz), 3.54 (s, 3H), 3.20 (dd, 1H, J=5.9, 5.9 Hz), 3.03 (dd, 1H, J=8.64, 8.6 Hz);

MS: m/z 280.0 (M+1).

Step 3: Preparation of methyl 3-isothiocyanato-3-{3-[(trifluoromethyl)sulfanyl]phenyl}propanoate

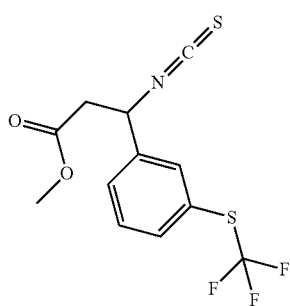 [SMILES: COC(=O)CC(N=C=S)c1cccc(SC(F)(F)F)c1]

To a suspension of methyl 3-amino-3-{3-[(trifluoromethyl)sulfanyl]phenyl}propanoate hydrochloride (from step 2) (1.3 g, 4 mmol) in dichloromethane (15 mL) cooled at 0° C. was added thiophosgene (0.5 mL, d=1.5 g/mL, 6.2 mmol) followed by 10% aqueous sodium bicarbonate solution (150 mL). The reaction mixture was then stirred at ambient temperature. After 1 h, the reaction mixture was diluted with 10% aqueous sodium bicarbonate solution (50 mL) and extracted with dichloromethane (3×100 mL). The combined organic extracts were dried over anhydrous sodium sulphate and evaporated to dryness to afford methyl 3-isothiocyanato-3-{3-[(trifluoromethyl)sulfanyl]phenyl}propanoate (0.7 g) as a yellow liquid.

$^1$H NMR (400 MHz, DMSO-$d_6$) δ 7.83 (s, 1H), 7.71 (d, 2H, J=7.6 Hz), 7.59 (t, 1H, J=7.6 Hz), 5.58 (dd, 1H, J=4.8, 8.8 Hz), 3.64 (s, 3H), 3.19 (dd, 1H, J=9.2, 16.8 Hz), 3.05 (dd, 1H, J=4.8, 16.4 Hz);

Step 4: Preparation of 2,1,3-benzothiadiazol-4-ylmethanol

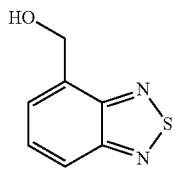

To a stirred solution of 4-(bromomethyl)-2,1,3-benzothiadiazole (5 g, 22 mmol) in 1:1 mixture of dioxane:water (60 mL) was added solid K$_2$CO$_3$ (15 g, 109 mmol) and refluxed. After 16 h, the above reaction mixture was quenched with water (25 mL) and extracted with ethyl acetate (3×150 mL). The combined organic layer was washed with brine solution (25 mL), dried over anhydrous sodium sulphate, filtered and concentrated to afford the desired product (3.0 g) as yellow liquid. It was purified by flash column (230-400 mesh silica gel), the product fraction was eluted using 30% ethyl acetate in hexane to afford 2,1,3-benzothiadiazol-4-ylmethanol (2.5 g) as a yellow solid.

$^1$H NMR (400 MHz, DMSO-$d_6$) δ 7.96 (d, 1H, J=8.40 Hz), 7.75-7.68 (m, 2H), 5.51 (t, 1H, J=5.60 Hz), 5.02 (d, 2H, J=5.20 Hz);

MS: m/z 166 (M+).

Step 5: Preparation of (2,3-diaminophenyl)methanol

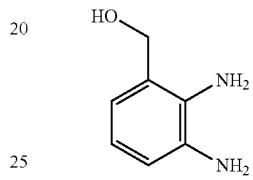

To a stirred solution of 2,1,3-benzothiadiazol-4-ylmethanol (2.5 g, 15 mmol) (from step 4) in methanol (150 mL) was added Raney nickel (100% w/w, washed five times with methanol) and it was hydrogenated under balloon pressure of hydrogen gas at ambient temperature. After 16 h, the reaction mixture was filtered through a celite bed and the residue was washed with methanol (3×250 mL). The combined filtrate was concentrated to afford (2, 3-diaminophenyl) methanol (1.6 g) as blue gum.

$^1$H NMR (400 MHz, DMSO-$d_6$) δ 6.48 (d, 1H, J=7.20 Hz), 6.42 (d, 1H, J=7.20 Hz), 6.36 (t, 1H, J=7.20 Hz), 4.92 (bs, 1H), 4.43 (s, 2H), 4.35 (d, 4H, J=14.80 Hz);

Step 6: Preparation of methyl 3-({-[2-amino-6-(hydroxymethyl)phenyl]carbamothioyl}amino)-3-{3-[(trifluoromethyl)sulfanyl]phenyl}propanoate

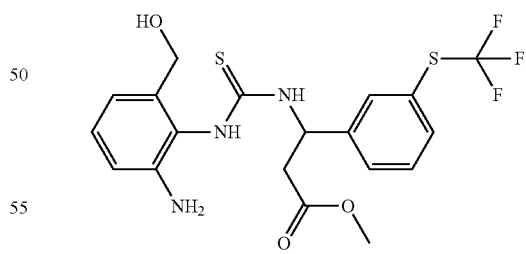

A mixture of methyl 3-isothiocyanato-3-{3-[(trifluoromethyl)sulfanyl]phenyl}propanoate (from step 3) (1.3 g, 4 mmol) and (2,3-diaminophenyl)methanol (step 5) (0.48 g, 3.47 mmol) in dichloromethane (50 mL) was stirred at ambient temperature for 12 h. The reaction mixture was concentrated to afford a crude product (1.8 g) as a brownish gum, which was purified by silica gel (230-400 mesh) column chromatography eluting with 7% methanol in chloroform to afford methyl 3-(3-(2-amino-6-(hydroxymethyl)

phenyl)thioureido)-3-(3-((trifluoromethyl)thio)phenyl)propanoate (1.3 g) as a brownish solid.

MS: m/z 460.0 (M+1).

Step 7: Preparation of methyl 3-{[4-(hydroxymethyl)-1H-1,3-benzodiazol-2-yl]amino}-3-{3-[(trifluoromethyl)sulfanyl]phenyl}propanoate

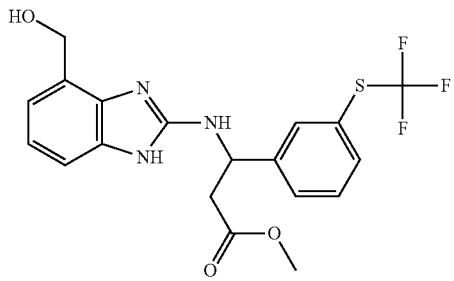 [SMILES: COC(=O)CC(Nc1nc2c(CO)cccc2[nH]1)c1cccc(SC(F)(F)F)c1]

To a solution of methyl 3-(3-(2-amino-6-(hydroxymethyl)phenyl)thioureido)-3-(3-((trifluoromethyl)thio)phenyl)propanoate (from step 6) (1 g, 2 mmol) in methanol (50 mL) was added iodoacetic acid (0.33 g, 2 mmol) and the mixture was refluxed for 2 h. The reaction mixture was evaporated to afford the required product, used in the next step without further purification, methyl 3-{[4-(hydroxymethyl)-1H-1,3-benzodiazol-2-yl]amino}-3-{3-[(trifluoromethyl)sulfanyl]phenyl}propanoate (1.4 g) as a brown solid.

$^1$H NMR (400 MHz, DMSO-d$_6$) δ 9.01 (bs, 1H), 7.87 (s, 1H), 7.54 (d, 1H, J=7.6 Hz), 7.67 (d, 1H, J=7.6 Hz), 7.58 (t, 1H, J=8 Hz), 7.27 (t, 1H, J=1.2 Hz), 7.18 (d, 2H, J=0.4 Hz), 5.43 (dd, 2H, J=7.2, 15.2 Hz), 4.72 (s, 2H), 3.59 (s, 3H), 3.16 (t, 2H, J=5.6 Hz);

MS: m/z 426.0 (M+1).

Example 21, step 8: Preparation of 3-{[4-(hydroxymethyl)-1H-1,3-benzodiazol-2-yl]amino}-N-methyl-3-{3-[(trifluoromethyl)sulfanyl]phenyl}propanamide

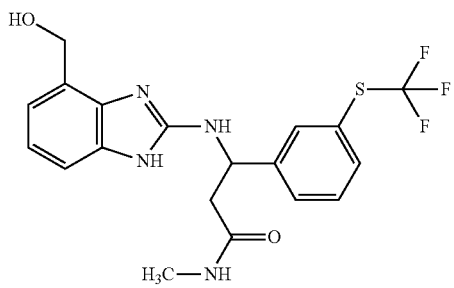 [SMILES: CNC(=O)CC(Nc1nc2c(CO)cccc2[nH]1)c1cccc(SC(F)(F)F)c1]

To a solution of methyl 3-{[4-(hydroxymethyl)-1H-1,3-benzodiazol-2-yl]amino}-3-{3-[(trifluoromethyl)sulfanyl]phenyl}propanoate (from step 7) (1 g, 2.35 mmol) in methanol (10 mL) was added aqueous methylamine solution (40%, 10 mL, 7 mmol) and the mixture was stirred for 2 h at RT. The reaction mixture was evaporated to afford the crude product (1.2 g). The crude product was purified by silica gel (230-400 mesh) column chromatography using 5% methanol in chloroform as eluent to afford the desired product 3-{[4-(hydroxymethyl)-1H-1,3-benzodiazol-2-yl]amino}-N-methyl-3-{3-[(trifluoromethyl)sulfanyl]phenyl}propanamide (0.38 g) as an off white solid.

$^1$H NMR (400 MHz, AcOH-d$_4$) δ 7.87 (s, 1H), 7.73 (d, 1H, J=7.6 Hz), 7.66 (d, 1H, J=8.0 Hz), 7.52 (t, 1H, J=7.6 Hz), 7.35 (d, 1H, J=5.6 Hz), 7.22 (t, 2H, J=7.6 Hz), 5.63 (dd, 1H, J=5.2, 8.8 Hz), 4.91 (s, 2H), 3.10 (dd, 1H, J=9.6, 14.8 Hz), 2.97 (dd, 1H, J=5.2, 8.9 Hz), 2.72 (s, 3H);

MS: m/z 425.2 (M+1).

Example 22: Preparation of 3-[(1H-1,3-benzodiazol-2-yl)amino]-3-(3,4-dichlorophenyl)-N-methylpropanamide

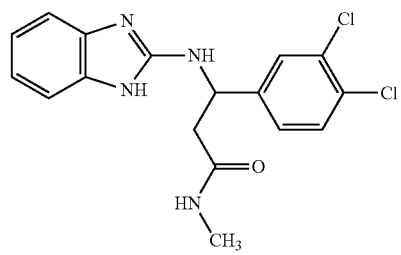 [SMILES: CNC(=O)CC(Nc1nc2ccccc2[nH]1)c1ccc(Cl)c(Cl)c1]

Starting with 3,4-dichlorobenzaldehyde, the procedures described in Example 9, steps 1 to 6, where applied to afford 3-[(1H-1,3-benzodiazol-2-yl)amino]-3-(3,4-dichlorophenyl)-N-methylpropanamide as an off-white solid.

$^1$H NMR (400 MHz, AcOH-d$_4$) δ 7.68 (d, 1H, J=1.76 Hz), 7.52 (d, 1H, J=8.36 Hz), 7.45-7.39 (m, 3H), 7.26-7.23 (m, 2H), 5.44 (q, 1H, J=5.00 Hz), 3.09 (dd, 1H, J=9.64, 14.74 Hz), 2.93 (dd, 1H, J=5.36, 12.60 Hz), 2.75 (s, 3H);

MS: m/z 364.2 (M+1).

Example 23: Preparation of 3-[(1H-1,3-benzodiazol-2-yl)amino]-3-(3-cyanophenyl)-N-methylpropanamide

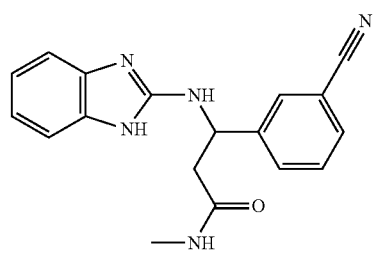 [SMILES: CNC(=O)CC(Nc1nc2ccccc2[nH]1)c1cccc(C#N)c1]

Starting with 3-formylbenzonitrile, the procedures described in Example 9, steps 1 to 6, where applied to afford 3-[(1H-1,3-benzodiazol-2-yl)amino]-3-(3-cyanophenyl)-N-methylpropanamide as an off-white solid.

$^1$H NMR (400 MHz, DMSO-d$_6$) δ 10.86 (s, 1H), 7.84 (t, 2H, J=5.56 Hz), 7.73 (d, 1H, J=7.92 Hz), 7.67 (td, 1H,

J=1.16, 4.44 Hz), 7.51 (t, 1H, J=7.72 Hz), 7.33 (d, 1H, J=8.92 Hz), 7.09 (d, 2H, J=8.92 Hz), 6.84 (br s, 2H), 5.30 (q, 1H, J=7.08 Hz), 2.70 (dd, 1H, J=7.28, 14.56 Hz), 2.62 (dd, 1H J=6.56, 14.54 Hz), 2.52 (s, 3H);

MS: m/z 321.2 (M+1).

Example 24: Preparation of methyl 3-{1-[(1H-1,3-benzodiazol-2-yl)amino]-2-(methylcarbamoyl)ethyl}benzoate

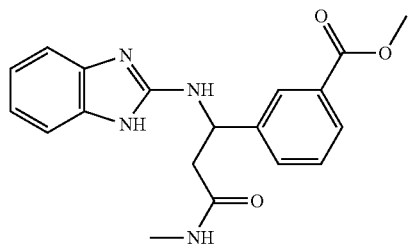 [SMILES: CNC(=O)CC(Nc1nc2ccccc2[nH]1)c1cccc(C(=O)OC)c1]

To a cooled (0° C.) solution of 3-[(1H-1,3-benzodiazol-2-yl)amino]-3-(3-cyanophenyl)-N-methylpropanamide (Example 23) (0.7 g, 2 mmol) in methanol, HCl gas was purged for 45 min, Then the reaction mixture was slowly warmed to ambient temperature. After 16 h the reaction mixtures was concentrated to remove methanol, and the residue was basified with 10% NaOH (pH-8) and extracted with ethyl acetate to afford methyl 3-{1-[(1H-1,3-benzodiazol-2-yl)amino]-2-(methylcarbamoyl)ethyl}benzoate (0.63 g) as an off-white solid.

$^1$H NMR (400 MHz, AcOH-$d_4$) δ 8.19 (s, 1H), 8.01 (d, 1H, J=6.80 Hz), 7.78 (d, 1H, J=7.60 Hz), 7.52 (t, 1H, J=8.00 Hz), 7.40 (dd, 2H, J=2.80, 5.80 Hz), 7.24 (dd, 2H, J=3.20, 6.00 Hz), 5.52 (dd, 1H, J=4.40, 9.60 Hz), 3.94 (s, 3H), 3.12 (dd, 1H, J=10.00, 14.40 Hz), 2.95 (dd, 1H, J=4.40, 14.60 Hz), 2.75 (s, 3H);

MS: m/z 353.2 (M+1).

Example 25: Preparation of 4-[(1H-1,3-benzodiazol-2-yl)amino]-N-methyl-4-[3-(trifluoromethyl)phenyl]butanamide

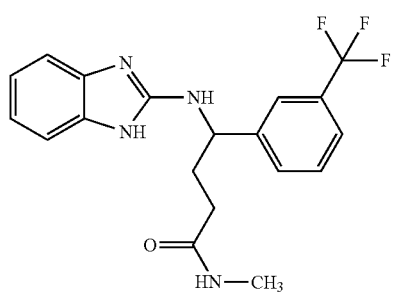 [SMILES: CNC(=O)CCC(Nc1nc2ccccc2[nH]1)c1cccc(C(F)(F)F)c1]

Step 1: Preparation of 3-amino-3-[3-(trifluoromethyl)phenyl]propanoic acid

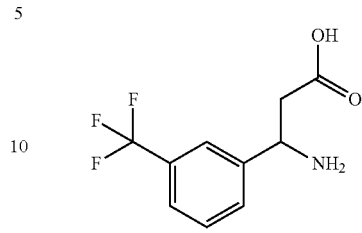

A mixture of malonic acid (298.82 g, 2872 mmol), ammonium formate (362.14 g, 5743 mmol) and 3-(trifluoromethyl)benzaldehyde (commercially available) (500 g, 2873 mmol) in ethanol (1000 mL) was refluxed for 12 h. The reaction mixture was evaporated to remove ethanol and the residue was triturated with acetone (2500 mL). The solid was filtered and dried to afford 3-amino-3-[3-(trifluoromethyl)phenyl]propanoic acid (255 g) as a white solid.

$^1$H NMR (400 MHz, AcOH-$d_4$) δ 7.87-7.81 (m, 2H), 7.74 (d, 1H, J=7.6 Hz), 7.66-7.62 (m, 1H), 4.98 (br. S, 1H), 3.36 (dd, 1H, J=16.0, 8.0 Hz), 3.13 (dd, 1H, J=17.6, 5.6 Hz);

MS: m/z 234 (M+1).

Step 2: Preparation of 3-{[(tert-butoxy)carbonyl]amino}-3-[3-(trifluoromethyl) phenyl]propanoic acid

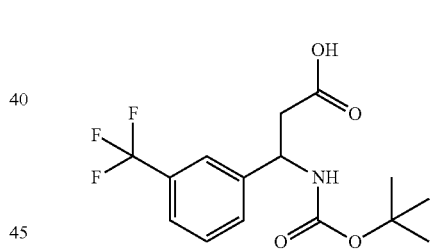

To a suspension of 3-amino-3-[3-(trifluoromethyl) phenyl] propanoic acid (from Step 1) (500 g, 2144 mmol) in t-BuOH (2500 mL) cooled to 0° C. was added NaOH (171.52 g, 4288 mmol) solution with water (1250 mL). This solution was stirred for 10 min and Boc-anhydride (561.56 g, 2573 mmol) was added drop wise and the mixture was then warmed to ambient temperature and stirred for 18 h. The reaction was dried and diluted with water and the mixture's pH was adjusted to 6 with citric acid and extracted with ethyl acetate (3×1000 mL). The combined organic extracts were dried over anhydrous sodium sulphate and evaporated to afford 3-{[(tert-butoxy)carbonyl]amino}-3-[3-(trifluoromethyl) phenyl] propanoic acid (595 g) as a colourless gum.

$^1$H NMR (300 MHz, DMSO-$d_6$) δ 7.78 (br.s, 1H), 7.63-7.54 (m, 3H), 6.14 (br.s, 1H), 4.90 (bs, 1H), 2.50 (s, 2H), 1.35 (s, 9H);

MS: m/z 332 (M-1).

Step 3: Preparation of tert-butyl N-{3-hydroxy-1-[3-(trifluoromethyl)phenyl]propyl} carbamate

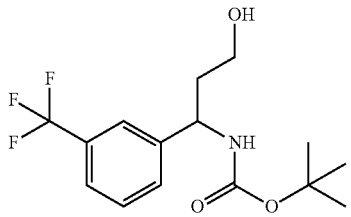 [SMILES: CC(C)(C)OC(=O)NC(CCO)c1cccc(C(F)(F)F)c1]

To a suspension of 3-((tert-butoxycarbonyl)amino)-3-(3-(trifluoromethyl)phenyl)propanoic acid (from step 2) (50 g, 150.01 mmol) in THF (150 mL) was added TEA (24.61 mL, d=0.72 g/mL, 180.01 mmol) and isobutyl chloroformate (19.51 mL, d=1.053 g/cm$^3$, 150.01 mmol) at 0° C. and stirred at 0° C. for 4 h. The solid that formed was filter off at 0° C. and the residue was washed with THF (50 mL). The combined filtrate was added to a cooled mixture of NaBH$_4$ (14.19 g, 375.02 mmol) in water (100 mL). The reaction mixture was slowly warmed to RT and stirred for 30 h. The reaction mixture was quenched with ice cold water (500 mL) and extracted with ethyl acetate (2×500 mL) and the combined organic layer was washed with brine, dried over Na$_2$SO$_4$, filtered and concentrated to afford a yellowish liquid (41 g) which was purified by column chromatography, using 35% ethyl acetate in petroleum ether as eluent to afford tert-butyl (3-hydroxy-1-(3-(trifluoromethyl) phenyl) propyl) carbamate (28.0 g) as pale yellow liquid.

$^1$H NMR (400 MHz, DMSO-d$_6$) δ 7.63-7.50 (m, 5H), 4.70 (d, 1H, J=6.8 Hz), 4.56 (s, 1H), 3.40-3.31 (m, 1H), 3.28 (t, 1H, J=5.2 Hz), 1.83 (dd, 1H, J=12.0, 6.0 Hz), 1.72 (dd, 1H, J=12.8, 6.4 Hz), 1.38 (s, 9H);
MS: m/z 220.1 [(M+1)-Boc].

Step 4: Preparation of tert-butyl N-[3-(methanesulfonyloxy)-1-[3-(trifluoromethyl)phenyl]propyl] carbamate

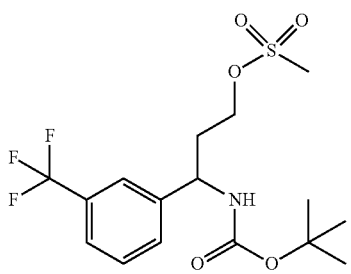 [SMILES: CC(C)(C)OC(=O)NC(CCOS(C)(=O)=O)c1cccc(C(F)(F)F)c1]

To a solution of tert-butyl N-[3-hydroxy-1-[3-(trifluoromethyl)phenyl]propyl]carbamate (from step 3) (100 g, 313.16 mmol) in dichloromethane (1000 mL), was added TEA (132.04 mL, 939.49 mmol) at 0° C., followed by mesyl chloride (31.50 mL, d=1.48 g/mL, 407.11 mmol). The reaction mixture was allowed to attain RT and stirred for 2 h. The reaction mixture was diluted with water (500 mL) and extracted with dichloromethane (2×500 mL). The combined organic layer was washed with brine, dried over Na$_2$SO$_4$, filtered and concentrated to afford tert-butyl N-[3-(methanesulfonyloxy)-1-[3-(trifluoromethyl)phenyl] propyl]carbamate (112 g) as a brown liquid, which was used in the next step without further purification.

$^1$H NMR (400 MHz, DMSO-d$_6$) δ 7.68-7.57 (m, 5H), 4.73 (q, 1H, J=8.48 Hz), 4.25 (dd, 1H, J=9.88, 6.92 Hz), 4.14 (dd, 1H, J=11.0, 5.72 Hz), 3.16 (s, 3H), 2.07 (q, 2H, J=5.76 Hz), 1.35 (s, 9H);
MS: m/z 298.0 [(M+1)-Boc].

Step 5: Preparation of tert-butyl N-{3-cyano-1-[3-(trifluoromethyl)phenyl]propyl} carbamate

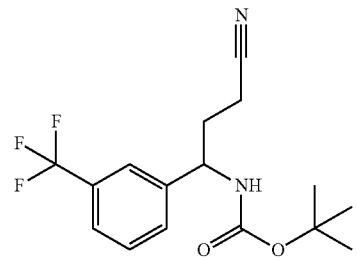 [SMILES: CC(C)(C)OC(=O)NC(CCC#N)c1cccc(C(F)(F)F)c1]

To a stirred solution of tert-butyl N-[3-(methanesulfonyloxy)-1-[3-(trifluoromethyl)phenyl] propyl]carbamate (from step 4) (11.0 g, 23.5 mmol) in N,N-dimethyl formamide (100 mL), was added sodium cyanide (1.15 g, 23.5 mmol) and the reaction was heated at 70° C. for 16 h. The reaction mixture was quenched with water (100 mL) and extracted with ethyl acetate (3×250 mL) and dried over anhydrous sodium sulphate, concentrated to afford crude product (7.72 g) as a yellow gum, which was purified by flash column chromatography over 230-400 mesh silica gel, using 10% ethyl acetate in hexane as eluent to afford tert-butyl N-{3-cyano-1-[3-(trifluoromethyl)phenyl]propyl} carbamate (4 g) as a colourless gum.

$^1$H NMR (400 MHz, DMSO-d$_6$) δ 7.66 (s, 1H, exchangeable), 7.62 (dd, 4H, J=15.2, 8.0 Hz), 4.64 (d, 1H, J=7.6 Hz), 2.51 (t, 2H, J=7.2 Hz), 1.94 (dd, 2H, J=14.4, 7.2 Hz), 1.37 (s, 9H);
MS: m/z 229.1 [(M+1)-Boc].

Step 6: Preparation of 4-amino-4-[3-(trifluoromethyl)phenyl]butanenitrile; trifluoroacetic acid

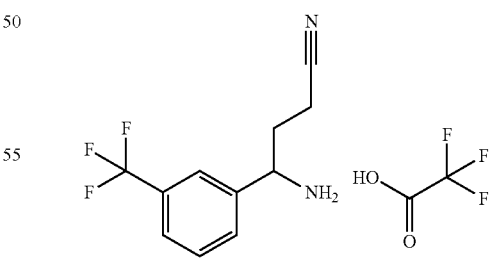

To a stirred solution of tert-butyl N-{3-cyano-1-[3-(trifluoromethyl)phenyl]propyl} carbamate (from step 5) (2.0 g, 6.09 mmol) in dichloromethane (20.0 mL) was added trifluoro acetic acid (0.7 mL, d=1.49 g/cm$^3$, 9.14 mmol) and the reaction was stirred at ambient temperature for 6 h. The reaction mixture was concentrated to afford 4-amino-4-[3-(trifluoromethyl)phenyl]butanenitrile; trifluoroacetic acid (0.9 g) as a brown gummy material, which was used in the next step without further purification.

MS: m/z 229.2 (M+1).

Step 7: Preparation of 4-isothiocyanato-4-[3-(trifluoromethyl)phenyl]butanenitrile

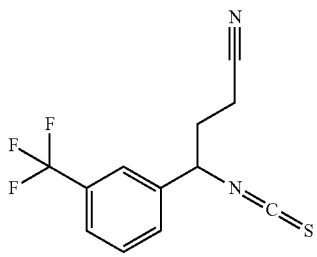 [SMILES: N#CCCC(N=C=S)c1cccc(C(F)(F)F)c1]

To a cooled solution of 4-amino-4-[3-(trifluoromethyl)phenyl]butanenitrile; trifluoroacetic acid (from step 6) (2.0 g, 5.85 mmol) in dichloromethane (50.0 mL), thiophosgene (0.62 mL, d=1.5 g/cm$^3$, 11.70 mmol) was added dropwise. After 20 minutes, 10% aqueous NaHCO$_3$ (50.0 mL) was added portionwise and the mixture was stirred at ambient temperature for 16 h. The reaction mixture was extracted with dichloromethane (3×150 mL) and the combined organic layer was dried over anhydrous Na$_2$SO$_4$, filtered, and concentrated to afford crude product (1.6 g) as yellow liquid, which was purified by gravity column chromatography over 60-120 mesh silica gel using 20% ethyl acetate in hexane as eluent to afford 4-isothiocyanato-4-[3-(trifluoromethyl)phenyl]butanenitrile (0.9 g) as a yellow gum.

$^1$H NMR (400 MHz, DMSO-d$_6$) δ 7.83 (s, 1H), 7.79 (d, 2H, J=7.6 Hz), 7.70 (t, 1H, J=8.0 Hz), 5.36 (dd, 1H, J=8.8, 4.8 Hz), 2.62 (t, 2H, J=7.2 Hz), 2.37-2.32 (m, 1H), 2.27-2.20 (m, 1H).

Step 8: Preparation of 1-(2-aminophenyl)-3-{3-cyano-1-[3-(trifluoromethyl)phenyl] propyl}thiourea

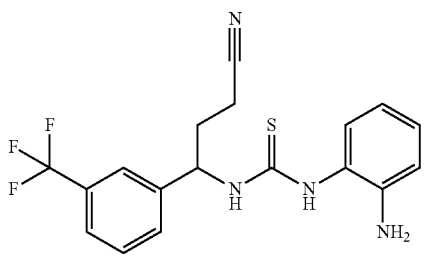 [SMILES: N#CCCC(NC(=S)Nc1ccccc1N)c1cccc(C(F)(F)F)c1]

To a stirred solution of benzene-1, 2-diamine (commercially available) (0.36 g, 3.33 mmol) in dichloromethane, 4-isothiocyanato-4-[3-(trifluoromethyl)phenyl]butanenitrile (from step 7) (0.9 g, 3.33 mmol) was added and the reaction mass was stirred at ambient temperature for 4 h. The reaction mixture was concentrated to afford crude product (1.26 g) as a yellow gum, which was purified by flash column chromatography over 230-400 mesh silica gel using 3% methanol in chloroform as eluent to afford 1-(2-aminophenyl)-3-{3-cyano-1-[3-(trifluoromethyl)phenyl]propyl}thiourea (0.6 g) as an off-white solid.

MS: m/z 379.6 (M+1).

Step 9: Preparation of 4-[(1H-1,3-benzodiazol-2-yl)amino]-4-[3-(trifluoromethyl)phenyl] butanenitrile

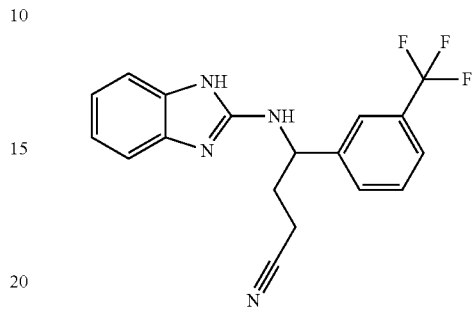

To a stirred solution of 1-(2-aminophenyl)-3-{3-cyano-1-[3-(trifluoromethyl)phenyl]propy} thiourea (from step 8) (0.6 g, 1.59 mmol) in methanol (20 mL), iodoacetic acid (0.663 g, 3.57 mmol) was added and the reaction mass was heated at 65° C. for 3 h. The reaction mixture was concentrated to afford crude product (0.546 g) as a yellow gum, which was purified by flash column chromatography over basic alumina using 4% methanol in chloroform as eluent to afford 4-[(1H-1,3-benzodiazol-2-yl)amino]-4-[3-(trifluoromethyl)phenyl] butanenitrile (0.35 g) as an off-white solid.

$^1$H NMR (400 MHz, CD$_3$OD) δ 7.81 (s, 1H), 7.74 (d, 1H, J=6.8 Hz), 7.61-7.55 (m, 2H), 7.21-7.18 (m, 2H), 7.00-6.96 (m, 2H), 5.04 (t, 1H, J=7.6 Hz), 2.65 (t, 2H, J=7.2 Hz), 2.24 (dd, 2H, J=14.8, 7.2 Hz);

MS: m/z 345.1 (M+1).

Step 10: Preparation of methyl 4-[(1H-1,3-benzodiazol-2-yl)amino]-4-[3-(trifluoromethyl)phenyl]butanoate

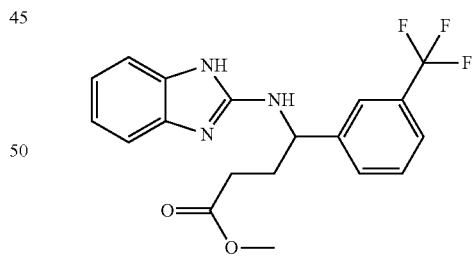

To a stirred solution of 4-[(1H-1,3-benzodiazol-2-yl)amino]-4-[3-(trifluoromethyl)phenyl] butanenitrile (from step 9) (0.3 g, 0.871 mmol) in methanol (10.0 mL), HCl gas was bubbled through at 0° C. for 20 min and the reaction mass maintained at 0° C. for 2 h. The reaction was concentrated and triturated with hexane (2×50 mL). The supernatant layer was decanted and the solid was collected to afford methyl 4-[(1H-1,3-benzodiazol-2-yl)amino]-4-[3-(trifluoromethyl)phenyl]butanoate (0.2 g) as an off-white solid, which was used in the next step without further purification.

$^1$H NMR (400 MHz, DMSO-d$_6$, D$_2$O) δ 7.89 (s, 1H), 7.83 (d, 1H, J=7.2 Hz), 7.66 (dd, 2H, J=14.4, 7.6 Hz), 7.39 (dd,

2H, J=6.0, 3.2 Hz), 7.23 (dd, 2H, J=6.0, 3.2 Hz), 5.04 (dd, 1H, J=8.4, 5.6 Hz), 3.57 (s, 3H), 2.47 (t, 2H, J=7.2 Hz) 2.19 (dd, 2H, J=18.0, 7.2 Hz);
MS: m/z 378.1 (M+1).

Example 25, Step 11: Preparation of 4-[(1H-1,3-benzodiazol-2-yl)amino]-N-methyl-4-[3-(trifluoromethyl)phenyl]butanamide

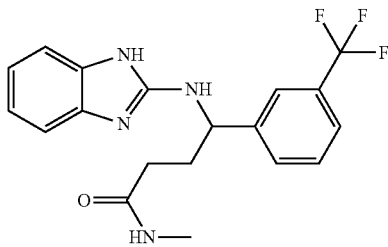 [SMILES: CNC(=O)CCC(Nc1nc2ccccc2[nH]1)c1cccc(C(F)(F)F)c1]

To a stirred solution of methyl 4-[(1H-1,3-benzodiazol-2-yl)amino]-4-[3-(trifluoromethyl)phenyl]butanoate (from step 10) (0.48 g, 1.27 mmol) in acetonitrile (10.0 mL) methylamine (0.42 mL, d=0.9 g/cm$^3$, 12.7 mmol, 40% aqueous solution) was added at 0° C. and then the reaction mixture was slowly warmed to ambient temperature for 4 h. The reaction mixture was concentrated to afford crude product (0.48 g) as a yellow gum, which was purified by flash column chromatography over 230-400 mesh silica gel using 4% methanol in chloroform as eluent to afford methyl 4-[(1H-1,3-benzodiazol-2-yl)amino]-4-[3-(trifluoromethyl)phenyl]butanoate (0.270 g) as a colourless gum.
$^1$H NMR (400 MHz, DMSO-d$_6$) δ 10.85 (bs, 1H), 7.76 (t, 1H, J=6.0 Hz), 7.71 (d, 2H, J=6.0 Hz), 7.55 (t, 2H, J=6.4 Hz), 7.45 (bs, 1H), 7.08 (t, 2H, J=4.4 Hz), 6.84 (bs, 2H), 4.89 (t, 1H, J=8.4 Hz), 2.54 (d, 3H, J=4.4 Hz), 2.16 (dd, 2H, J=13.6, 6.4 Hz), 2.03 (dd, 2H, J=14.8, 8.0 Hz);
MS: m/z 377.0 (M+1).

The above product was resolved into its two isomers by Chiral SFC using Column: Chiralcel OZH, Flow rate: 3 mL/min, Co-solvent: 30%, Co-solvent name: 0.5% Di-ethylamine in Isopropyl alcohol, Outlet pressure: 100 bar, Injected volume: 15.0 μL, temperature: 35° C. with CO$_2$.

Example 25a: (−)-4-[(1H-1,3-benzodiazol-2-yl)amino]-N-methyl-4-[3-(trifluoromethyl)phenyl]butanamide The (−) enantiomer was the first isomer to elute off the column.
$^1$H NMR (400 MHz, AcOH-d$_4$) δ 7.78 (t, 2H, J=8.0 Hz), 7.65-7.56 (m, 2H), 7.39 (dd, 2H, J=6.0, 3.6 Hz), 7.26-7.23 (m, 2H), 5.09 (t, 1H, J=6.8 Hz), 2.76 (s, 3H), 2.62-2.51 (m, 2H), 2.33 (dd, 2H, J=14.0, 7.6 Hz);
MS: m/z 377.2 (M+1);
[α]$_D$ $^{24.2}$ (−) 57.00, (MeOH, C=0.1).

Example 25b: (+)-4-[(1H-1,3-benzodiazol-2-yl)amino]-N-methyl-4-[3-(trifluoromethyl)phenyl]butanamide The (+) enantiomer was the second isomer to elute off the column.
$^1$H NMR (400 MHz, AcOH-d$_4$) δ 7.78 (t, 2H, J=8.4 Hz), 7.65-7.56 (m, 2H), 7.39 (dd, 2H, J=5.6, 2.8 Hz), 7.26-7.22 (m, 2H), 5.09 (t, 1H, J=6.4 Hz), 2.76 (s, 3H), 2.61-2.53 (m, 2H), 2.34 (t, 2H, J=7.6 Hz);
MS: m/z 377.2 (M+1);
[α]$_D$ $^{24.6}$ (+) 65.00, (MeOH, C=0.1).

Example 26: Preparation of 2-[(1H-1,3-benzodiazol-2-yl)amino]-N-methyl-2-[3-(trifluoromethyl)phenyl]propanamide; trifluoroacetic acid

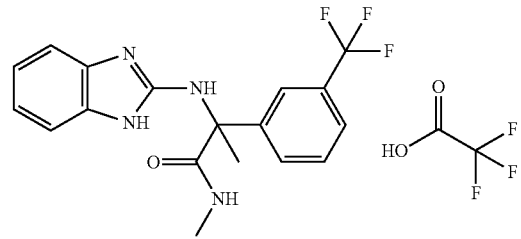 [SMILES: CNC(=O)C(C)(Nc1nc2ccccc2[nH]1)c1cccc(C(F)(F)F)c1 ; O=C(O)C(F)(F)F]

Step 1: Preparation of 5-methyl-5-[3-(trifluoromethyl)phenyl]imidazolidine-2,4-dione

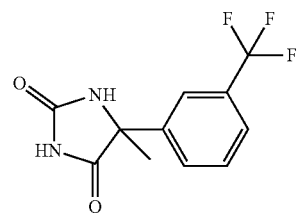 [SMILES: CC1(c2cccc(C(F)(F)F)c2)NC(=O)NC1=O]

To a stirred solution of 3-trifluoromethyl acetophenone (commercially available) (45.0 g, 239 mmol) in a mixture of ethanol/water (1:1, 600 mL) was added ammonium carbonate (115 g, 1200 mmol) followed by potassium cyanide (18.7 g, 287 mmol) and the mixture was stirred at 60° C. for 16 h. The reaction mixture was poured into ice-cold water (1500 mL) and it was stirred for 30 min. The solid formed was filtered off and dried to afford 5-methyl-5-[3-(trifluoromethyl)phenyl]imidazolidine-2,4-dione (56.0 g) as an off-white solid, which was used in next step without further purification.
$^1$H NMR (400 MHz, DMSO-d$_6$) δ 10.90 (s, 1H), 8.75 (s, 1H), 7.83 (d, 1H, J=7.6 Hz), 7.77 (s, 1H), 7.73 (d, 1H, J=7.6 Hz), 7.66 (t, 1H, J=7.6 Hz), 1.69 (s, 3H);
MS: m/z 259 (M+1).

Step 2: Preparation of 2-amino-2-[3-(trifluoromethyl)phenyl]propanoic acid

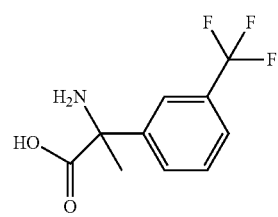 [SMILES: CC(N)(C(=O)O)c1cccc(C(F)(F)F)c1]

5-methyl-5-[3-(trifluoromethyl)phenyl]imidazolidine-2,4-dione (from step 1) (50.0 g, 194 mmol) was suspended in 10% aqueous sodium hydroxide solution (200 mL) and the mixture was refluxed for 48 h. The reaction mixture was neutralised (adjusted pH=7) with 6.0 N HCl (150 mL), and the solid that formed was filtered and dried to afford 2-amino-2-[3-(trifluoromethyl)phenyl]propanoic acid (40.0 g) as white solid, which was used in the next step without further purification.

¹H NMR (400 MHz, DMSO-d₆: D₂O) δ 7.82 (s, 1H), 7.77 (d, 1H, J=7.64 Hz), 7.64 (d, 1H, J=7.36 Hz), 7.58 (t, 1H, J=7.72 Hz), 1.67 (s, 3H);
MS: m/z 234.1 (M+1).

Step 3: Preparation of methyl 2-amino-2-[3-(trifluoromethyl)phenyl]propanoate hydrochloride

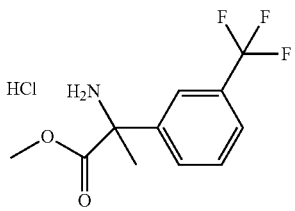 [SMILES: COC(=O)C(C)(N)c1cccc(C(F)(F)F)c1 ; Cl]

To a stirred solution of 2-amino-2-[3-(trifluoromethyl)phenyl]propanoic acid (from step 2) (6.0 g, 25.7 mmol) in methanol (50.0 mL) was added thionyl chloride (5.6 mL, d=1.64 g/cm³, 77.2 mmol) at 0° C. After the completion of addition, the reaction mixture was allowed to warm to ambient temperature and then refluxed for 16 h. The reaction mixture was concentrated under reduced pressure to afford methyl 2-amino-2-[3-(trifluoromethyl)phenyl]propanoate hydrochloride (7.3 g) as an off-white solid, which was used in the next step without further purification.

¹H NMR (400 MHz, DMSO-d₆) δ 9.59 (bs, 3H), 7.93 (s, 1H), 7.88 (s, 1H), 7.84 (t, 1H, J=8.4 Hz), 7.73 (t, 1H, J=9.6 Hz), 3.76 (s, 3H), 1.97 (s, 3H);
MS: m/z 248.1 (M+1).

Step 4: Preparation of methyl 2-isothiocyanato-2-[3-(trifluoromethyl)phenyl] propanoate

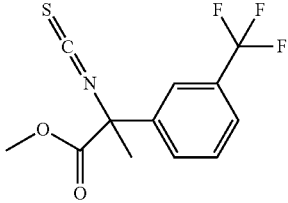 [SMILES: COC(=O)C(C)(N=C=S)c1cccc(C(F)(F)F)c1]

To a stirred solution of methyl 2-amino-2-[3-(trifluoromethyl)phenyl]propanoate hydrochloride (from step 3) (3.3 g, 11.6 mmol) in dichloromethane (60.0 mL) were added 10% aqueous sodium bicarbonate solution (60 mL) at 0° C. followed by thiophosgene (4.01 g, 34.9 mmol) and the reaction mixture was stirred at ambient temperature for 30 min. The reaction mixture was diluted with dichloromethane (100 mL), the organic phase was separated, dried over anhydrous sodium sulphate, filtered and concentrated under reduced pressure to afford crude product (3.37 g) as a yellow gum, which was purified by gravity column chromatography over 60-120 mesh silica gel using 5-10% ethyl acetate in hexane as eluent to afford methyl 2-isothiocyanato-2-[3-(trifluoromethyl)phenyl]propanoate (1.8 g) as a yellowish liquid.

¹H NMR (400 MHz, DMSO-d₆) δ 7.83 (d, 2H, J=7.5 Hz), 7.52 (t, 2H, J=8.2 Hz), 3.77 (s, 3H), 2.05 (s, 3H);
GCMS: m/z 289.0 (M−1).

Step 5: Preparation of methyl 2-{[(2-aminophenyl)carbamothioyl]amino}-2-[3-(trifluoromethyl)phenyl]propanoate

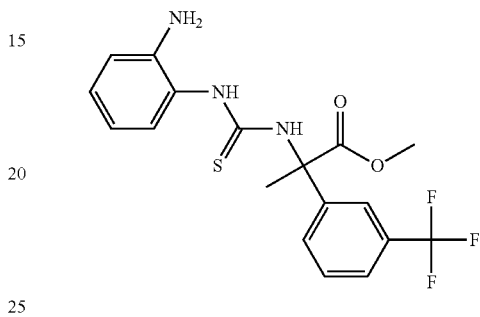

A mixture of methyl 2-isothiocyanato-2-[3-(trifluoromethyl)phenyl]propanoate (from step 4) (1.0 g, 3.46 mmol) and benzene-1, 2-diamine (commercially available) (0.34 g, 3.11 mmol) in dichloromethane (50.0 mL) was stirred at ambient temperature for 16 h. The reaction mixture was concentrated under reduced pressure to afford methyl 2-{[(2-aminophenyl)carbamothioyl]amino}-2-[3-(trifluoromethyl)phenyl]propanoate (1.37 g) as a brown gum, which was used in the next step without further purification.

Step 6: Preparation of methyl 2-[(1H-1,3-benzodiazol-2-yl)amino]-2-[3-(trifluoromethyl)phenyl]propanoate

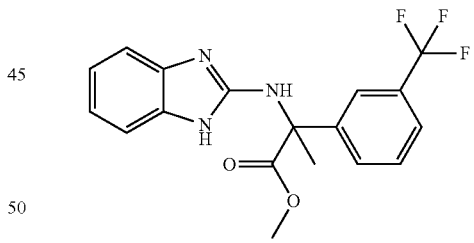

To a stirred solution of methyl 2-{[(2-aminophenyl)carbamothioyl]amino}-2-[3-(trifluoromethyl)phenyl]propanoate (from step 5) (1.37 g, 3.45 mmol) in methanol (30 mL) was added iodoacetic acid (0.77 g, 4.14 mmol) and the reaction mixture was heated at 75° C. for 2 h. The reaction mixture was concentrated under reduced pressure to afford crude product (1.3 g) as a brown gum, which was purified on a GRACE instrument on a pre-packed 24.0 g cartridge and the product fraction was eluted using 1-2% methanol in chloroform as eluent to afford methyl 2-[(1H-1,3-benzodiazol-2-yl)amino]-2-[3-(trifluoromethyl) phenyl]propanoate (0.43 g) as a yellow solid.

¹H NMR (400 MHz, DMSO-d₆) δ 10.65 (s, 1H), 7.84 (t, 2H, J=9.64 Hz), 7.70 (d, 1H, J=7.84 Hz), 7.63 (t, 1H, J=7.80

Hz) 7.49 (s, 1H), 7.19 (dd, 1H, J=4.12, 1.64 Hz), 7.12 (dd, 1H, J=4.84, 2.64 Hz) 6.91-6.85 (m, 2H), 3.64 (s, 3H), 2.06 (s, 3H);
MS: m/z 364.1 (M+1).

Example 26, Step 7: Preparation of 2-[(1H-1,3-benzodiazol-2-yl)amino]-N-methyl-2-[3-(trifluoromethyl)phenyl]propanamide; trifluoroacetic acid

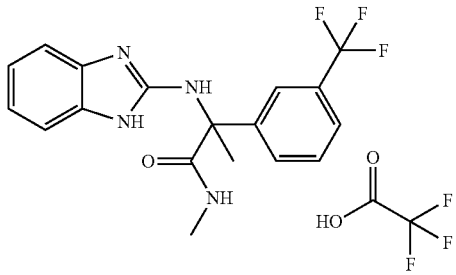

To a solution of methyl 2-[(1H-1,3-benzodiazol-2-yl)amino]-2-[3-(trifluoromethyl) phenyl]propanoate (from step 6) (0.6 g, 1.65 mmol) in acetonitrile (10.0 mL) was added aqueous solution of methyl amine (1.3 g, 16.5 mmol, 40% in water) at 0° C. and the reaction mixture was stirred at ambient temperature for 5 h. The reaction mixture was concentrated under reduced pressure to afford crude product (0.600 g) as a brown gum, which was purified by prep. HPLC. The desired product fraction obtained from prep. HPLC (purified by TFA method) was concentrated under reduced pressure to afford 2-[(1H-1,3-benzodiazol-2-yl)amino]-N-methyl-2-[3-(trifluoromethyl)phenyl]propanamide; trifluoroacetic acid (0.580 g) as a yellowish gum.

$^1$H NMR (400 MHz, DMSO-$d_6$) δ 12.28 (bs, 2H), 9.53 (s, 1H), 8.32 (d, 1H, J=4.52 Hz), 7.93 (d, 1H, J=12.32 Hz), 7.70 (t, 2H, J=7.92 Hz), 7.66 (t, 1H, J=7.88 Hz), 7.42 (dd, 1H, J=6.72, 3.25 Hz), 7.40 (d, 1H, J=3.84 Hz), 7.25 (t, 1H, J=2.76 Hz) 7.23 (d, 1H, J=3.16 Hz), 2.67 (d, 3H, J=4.4 Hz), 2.09 (s, 3H);
MS: m/z 363.1 (M+1).

The above product was resolved into its two isomers by Chiral SFC using Column: Lux A1, Flow rate: 3.0 mL/min, Co-solvent: 30%, Co-solvent name: 0.5% Isopropyl amine in Methanol, Outlet pressure: 100 bar, Injected volume: 3.0 μL, temperature: 35° C. with $CO_2$.

Example 26a: (+)-2-[(1H-1,3-benzodiazol-2-yl)amino]-N-methyl-2-[3-(trifluoromethyl) phenyl]propanamide The (+) enantiomer was the first isomer to elute off the column.
$^1$H NMR (400 MHz, DMSO-$d_6$) δ 10.74 (s, 1H), 8.05 (d, 1H, J=4.28 Hz), 7.80 (s, 1H), 7.75 (d, 1H, J=7.52 Hz), 7.60 (d, 1H, J=7.40 Hz), 7.56 (t, 1H, J=7.68 Hz), 7.31 (s, 1H), 7.13 (s, 1H), 7.06 (s, 1H), 6.84 (t, 2H, J=2.80 Hz), 2.59 (t, 3H, J=4.44 Hz), 2.11 (s, 3H);
MS: m/z 363.1 (M+1);
$[α]_D$ $^{24.9}$ (±) 68.15, (MeOH, C=1.060).

Example 26b: (+2-[(1H-1,3-benzodiazol-2-yl)amino]-N-methyl-2-[3-(trifluoromethyl) phenyl]propanamide The (−) enantiomer was the second to elute off the column
$^1$H NMR (400 MHz, DMSO-$d_6$) δ 10.75 (s, 1H), 8.06 (d, 1H, J=4.48 Hz), 7.81 (s, 1H), 7.75 (d, 1H, J=7.68 Hz), 7.60 (d, 1H, J=7.72 Hz), 7.56 (t, 1H, J=7.68 Hz), 7.32 (s, 1H), 7.12 (s, 1H), 7.09 (s, 1H), 6.85 (t, 1H, J=4.00 Hz), 6.83 (d, 1H, J=3.12 Hz), 2.59 (d, 3H, J=4.44 Hz), 2.11 (s, 3H);
MS: m/z 363.1 (M+1);
$[α]_D$ $^{24.9}$ (−) 62.45, (MeOH, C=1.055).

We claim:
1. A pharmaceutical composition comprising:
a compound of formula (I)

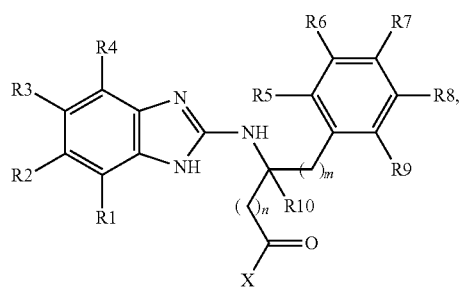

wherein:
n is an integer selected from 0, 1, and 2;
m is an integer selected from 0, 1, and 2;
R1-R4 are independently a group selected from H, halogen, CN, $C_{1-6}$ alkyl, $C_{1-6}$ alkylene-OH, $C_{1-6}$ alkoxy, $OCF_3$, $C_{1-6}$ alkylene-O—$C_{1-6}$ alkyl, $C_{1-6}$ alkylene-S—$C_{1-6}$ alkyl, $C_{3-7}$cycloalkyl, and $NR^cC(=O)$—$C_{1-6}$alkyl wherein $R^c$ is selected from H, $C_{1-6}$ alkyl, and $C_{1-6}$ alkylene-$NR^aR^b$, wherein $R^a$ and $R^b$ are independently a group selected from H, $C_{1-6}$ alkyl, $C_{1-6}$ alkylene-OH, $C_{1-6}$ alkylene-O—$C_{1-6}$ alkyl, $C(=O)$—$C_{1-6}$alkyl, $C(=O)$—$C_{1-6}$alkoxy, $C(=O)$—$C_{1-6}$alkyl-CN, $C(=O)$—$C_{1-6}$alkyl-OH, $C(=O)$—$C_{1-6}$ alkylene-S—$C_{1-6}$ alkyl, $C(=O)$—O—$C_{1-6}$ alkylene-O—$C_{1-6}$ alkyl, $C(=O)$—O—$C_{1-6}$alkyl-CN, $C(=O)$—O—$C_{1-6}$alkyl-OH, $C(=O)$—O—$C_{1-6}$ alkylene-S—$C_{1-6}$ alkyl, $C(=O)$—$NHC_{1-6}$alkyl, $C(=O)$—$NHC_{1-6}$ alkylene-O—$C_{1-6}$ alkyl, $C(=O)$—$NHC_{1-6}$ alkylene-S—$C_{1-6}$ alkyl, $C(=O)$—$NHC_{1-6}$ alkyl-CN, $C(=O)$—$NHC_{1-6}$alkyl-OH, $C(=O)$—$N(C_{1-6}$alkyl$)_2$, $SO_2$—$C_{1-6}$alkyl, $SO_2$—$C_{1-6}$ alkylene-O—$C_{1-6}$ alkyl, $SO_2$—$C_{1-6}$ alkylene-S—$C_{1-6}$ alkyl, $SO_2$—$C_{1-6}$alkyl-CN, $SO_2$—$C_{1-6}$alkyl-OH, and $SO_2$—$C_{1-6}$alkyl-$N(C_{1-6}$alkyl$)_2$;
R5-R9 are independently a group selected from H, halogen, $CH_2F$, $CHF_2$, $CF_3$, CN, $C_{1-6}$ alkyl, $C_{1-6}$ alkylene-OH, OH, $C_{1-6}$ alkoxy, $C_{1-6}$ alkylene-O—$C_{1-6}$ alkyl, $C_{1-6}$ alkylene-S—$C_{1-6}$ alkyl, $C_{3-7}$cycloalkyl, $C(=O)$—O—$C_{1-6}$ alkyl, S—$C_{1-6}$ alkyl, $SCF_3$, $OCF_3$, $OCF_2H$, $OCFH_2$, $OC_{3-7}$cycloalkyl, and $SC_{3-7}$cycloalkyl;
R10 is a group selected from H, $C_{1-6}$ alkyl, $C_{1-6}$alkyl substituted with 1 to 3 Fluorine atoms, and $C_{3-4}$cycloalkyl;
X is selected from
a) OR11, wherein R11 is a group selected from $C_{1-6}$ alkyl, $C_{1-6}$ alkylene-OH, $C_{1-6}$ alkylene-O—$C_{1-6}$ alkyl, $C_{1-6}$ alkylene-S—$C_{1-6}$ alkyl, $C_{1-6}$ alkylene-CN, and $C_{1-6}$ alkylene-$CF_3$; and
b) NR12R13, wherein R12 is a group selected from H, and $C_{1-6}$ alkyl; and
R13 is a group selected from H, $C_{1-6}$ alkyl, OH, $C_{3-7}$ cycloalkyl, $C_{1-6}$ alkoxy, and $C_{2-6}$ alkenyl; or
a pharmaceutically acceptable salt thereof; and
optionally a pharmaceutically acceptable additive.

2. A method for treatment of a cardiac disease, disorder or condition in a mammal, comprising administering to a mammal in need of said treatment, a therapeutically effective amount of at least one compound of formula (I)

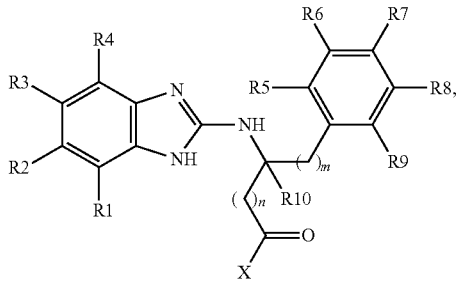

wherein:
n is an integer selected from 0, 1, and 2;
m is an integer selected from 0, 1, and 2;
R1-R4 are independently a group selected from H, halogen, CN, $C_{1-6}$ alkyl, $C_{1-6}$ alkylene-OH, $C_{1-6}$ alkoxy, $OCF_3$, $C_{1-6}$ alkylene-O—$C_{1-6}$ alkyl, $C_{1-6}$ alkylene-S—$C_{1-6}$ alkyl, $C_{3-7}$cycloalkyl, and $NR^cC(=O)$—$C_{1-6}$alkyl wherein $R^c$ is selected from H, $C_{1-6}$ alkyl, and $C_{1-6}$ alkylene-$NR^aR^b$, wherein $R^a$ and $R^b$ are independently a group selected from H, $C_{1-6}$ alkyl, $C_{1-6}$ alkylene-OH, $C_{1-6}$ alkylene-O—$C_{1-6}$ alkyl, $C(=O)$—$C_{1-6}$alkyl, $C(=O)$—$C_{1-6}$alkoxy, $C(=O)$—$C_{1-6}$alkyl-CN, $C(=O)$—$C_{1-6}$alkyl-OH, $C(=O)$—$C_{1-6}$ alkylene-S—$C_{1-6}$ alkyl, $C(=O)$—O—$C_{1-6}$ alkylene-O—$C_{1-6}$ alkyl, $C(=O)$—O—$C_{1-6}$alkyl-CN, $C(=O)$—O—$C_{1-6}$alkyl-OH, $C(=O)$—O—$C_{1-6}$ alkylene-S—$C_{1-6}$ alkyl, $C(=O)$—$NHC_{1-6}$alkyl, $C(=O)$—$NHC_{1-6}$ alkylene-O—$C_{1-6}$ alkyl, $C(=O)$—$NHC_{1-6}$ alkylene-S—$C_{1-6}$ alkyl, $C(=O)$—$NHC_{1-6}$ alkyl-CN, $C(=O)$—$NHC_{1-6}$alkyl-OH, $C(=O)$—$N(C_{1-6}$alkyl$)_2$, $SO_2$—$C_{1-6}$alkyl, $SO_2$—$C_{1-6}$ alkylene-O—$C_{1-6}$ alkyl, $SO_2$—$C_{1-6}$ alkylene-S—$C_{1-6}$ alkyl, $SO_2$—$C_{1-6}$alkyl-CN, $SO_2$—$C_{1-6}$alkyl-OH, and $SO_2$—$C_{1-6}$alkyl-$N(C_{1-6}$alkyl$)_2$;
R5-R9 are independently a group selected from H, halogen, $CH_2F$, $CHF_2$, $CF_3$, CN, $C_{1-6}$ alkyl, $C_{1-6}$ alkylene-OH, OH, $C_{1-6}$ alkoxy, $C_{1-6}$ alkylene-O—$C_{1-6}$ alkyl, $C_{1-6}$ alkylene-S—$C_{1-6}$ alkyl, $C_{3-7}$cycloalkyl, $C(=O)$—O—$C_{1-6}$ alkyl, S—$C_{1-6}$ alkyl, $SCF_3$, $OCF_3$, $OCF_2H$, $OCFH_2$, $OC_{3-7}$cycloalkyl, and $SC_{3-7}$cycloalkyl;
R10 is a group selected from H, $C_{1-6}$ alkyl, $C_{1-6}$alkyl substituted with 1 to 3 Fluorine atoms, and $C_{3-4}$cycloalkyl;
X is selected from
a) OR11, wherein R11 is a group selected from $C_{1-6}$ alkyl, $C_{1-6}$ alkylene-OH, $C_{1-6}$ alkylene-O—$C_{1-6}$ alkyl, $C_{1-6}$ alkylene-S—$C_{1-6}$ alkyl, $C_{1-6}$ alkylene-CN, and $C_{1-6}$ alkylene-$CF_3$; and
b) NR12R13, wherein R12 is a group selected from H, and $C_{1-6}$ alkyl; and
R13 is a group selected from H, $C_{1-6}$ alkyl, OH, $C_{3-7}$ cycloalkyl, $C_{1-6}$ alkoxy, and $C_{2-6}$ alkenyl; or
a pharmaceutically acceptable salt thereof.
3. The method of claim 2, wherein said cardiac disease, disorder or condition in a mammal is selected from the group consisting of cardiac arrhythmia, atrial arrhythmia, ventricular arrhythmia, atrial fibrillation, ventricular fibrillation, tachyarrhythmia, atrial tachyarrhythmia, ventricular tachyarrhythmia, bradyarrhythmias, and an abnormal rhythm arising after cardiac surgery or a cardiac ablation procedure.
4. The pharmaceutical composition of claim 1, wherein m of the compound of formula (I) is selected from 0 and 1.
5. The pharmaceutical composition of claim 1, wherein n of the compound of formula (I) is 1.
6. The pharmaceutical composition of claim 1, wherein n of the compound of formula (I) is 0.
7. The pharmaceutical composition of claim 1, wherein n of the compound of formula (I) is 2.
8. The pharmaceutical composition of claim 1, wherein R1 of the compound of formula (I) is selected from H, $C_{1-6}$ alkyl, $C_{1-6}$ alkylene-OH, halogen, $C_{1-6}$ alkylene-O—$C_{1-6}$ alkyl, and $NR^cC(=O)$—$C_{1-6}$alkyl wherein $R^c$ is selected from H and $C_{1-6}$ alkyl.
9. The pharmaceutical composition of claim 1, wherein R1 of the compound of formula (I) is selected from H, $CH_3$, $CH_2OH$, $CH_2CH_2OH$, Cl, $CH_2$—O—$CH_3$, and NH—C(=O)—$CH_3$.
10. The pharmaceutical composition of claim 1, wherein R2 of the compound of formula (I) is selected from H, $C_{1-6}$ alkyl, halogen, $OCF_3$ and CN.
11. The pharmaceutical composition of claim 1, wherein R2 of the compound of formula (I) is selected from H, F, $OCF_3$, $CH_3$, and CN.
12. The pharmaceutical composition of claim 1, wherein R3 of the compound of formula (I) is selected from H, $C_{1-6}$ alkyl, $C_{1-6}$ alkylene-OH, halogen, $C_{1-6}$ alkylene-O—$C_{1-6}$ alkyl, and $NR^cC(=O)$—$C_{1-6}$alkyl wherein $R^c$ is selected from H and $C_{1-6}$ alkyl.
13. The pharmaceutical composition of claim 1, wherein R3 of the compound of formula (I) is selected from H, $CH_3$, $CH_2OH$, $CH_2CH_2OH$, Cl, $CH_2$—O—$CH_3$, and NH—C(=O)—$CH_3$.
14. The pharmaceutical composition of claim 1, wherein R4 of the compound of formula (I) is selected from H, $C_{1-6}$ alkyl, $C_{1-6}$ alkylene-OH, halogen, $C_{1-6}$ alkylene-O—$C_{1-6}$ alkyl, and $NR^cC(=O)$—$C_{1-6}$alkyl wherein $R^c$ is selected from H and $C_{1-6}$ alkyl.
15. The pharmaceutical composition of claim 1, wherein R4 of the compound of formula (I) is selected from H, $CH_3$, $CH_2OH$, $CH_2CH_2OH$, Cl, $CH_2$—O—$CH_3$, and NH—C(=O)—$CH_3$.
16. The pharmaceutical composition of claim 1, wherein R5 of the compound of formula (I) is selected from H.
17. The pharmaceutical composition of claim 1, wherein R6 of the compound of formula (I) is selected from H, halogen, $CF_3$, $C(=O)$—O—$C_{1-3}$ alkyl, CN, $OCF_3$, S—$C_{1-3}$ alkyl, $SCF_3$ and $C_{1-6}$ alkyl.
18. The pharmaceutical composition of claim 1, wherein R6 of the compound of formula (I) is selected from H, Cl, F, $CF_3$, $CH_3$, $C(=O)$—O—$CH_3$, CN, $OCF_3$, S—$CH_3$, and $SCF_3$.
19. The pharmaceutical composition of claim 1, wherein R7 of the compound of formula (I) is selected from H, halogen, and $C_{1-6}$ alkyl.
20. The pharmaceutical composition of claim 1, wherein R7 of the compound of formula (I) is selected from H, Cl, Br, F, and $CH_3$.
21. The pharmaceutical composition of claim 1, wherein R8 of the compound of formula (I) is selected from H, halogen, $CF_3$, $C(=O)$—O—$C_{1-3}$ alkyl, S—$C_{1-3}$ alkyl, $OCF_3$ and $C_{1-6}$ alkyl.
22. The pharmaceutical composition of claim 1, wherein R8 of the compound of formula (I) is selected from H, Cl, F, $CF_3$, $CH_3$, $C(=O)$—O—$CH_3$, S—$CH_3$, and $OCF_3$.
23. The pharmaceutical composition of claim 1, wherein R9 of the compound of formula (I) is selected from H.

24. The pharmaceutical composition of claim 1, wherein R10 of the compound of formula (I) is selected from H and $C_{1-6}$ alkyl.

25. The pharmaceutical composition of claim 1, wherein X of the compound of formula (I) is selected from OR11.

26. The pharmaceutical composition of claim 1, wherein R11 of the compound of formula (I) is selected from $C_{1-6}$ alkyl.

27. The pharmaceutical composition of claim 1, wherein X of the compound of formula (I) is selected from NR12R13.

28. The pharmaceutical composition of claim 1, wherein R12 of the compound of formula (I) is selected from H and $C_{1-6}$ alkyl.

29. The pharmaceutical composition of claim 1, wherein R13 of the compound of formula (I) is selected from H, $C_{1-6}$ alkyl, $C_{3-7}$ cycloalkyl, $C_{1-6}$ alkoxy, and $C_{2-6}$ alkenyl.

30. The pharmaceutical composition of claim 1, wherein R13 of the compound of formula (I) is selected from H, $CH_3$, $CH_2CH_3$, isopropyl, isobutyl, cyclopropyl, cyclohexyl, $OCH_3$, and propenyl.

31. The pharmaceutical composition of claim 1, wherein the compound of formula (I) is selected from:
- 2-[(1H-1,3-benzodiazol-2-yl)amino]-N,N-dimethyl-2-[3-(trifluoromethyl)phenyl]acetamide,
- 3-[(1H-1,3-benzodiazol-2-yl)amino]-N-methyl-3-[3(trifluoromethyl)phenyl]propanamide,
- 3-[(1H-1,3-benzodiazol-2-yl)amino]-N-(prop-2-en-1-yl)-3-[3-(trifluoromethyl)phenyl]propanamide,
- 3-[(5-fluoro-4-methyl-1H-1,3-benzodiazol-2-yl)amino]-N-methyl-3-[3-(trifluoromethyl)phenyl]propanamide,
- N-methyl-3-[(4-methyl-1H-1,3-benzodiazol-2-yl)amino]-3-[3-(trifluoromethyl)phenyl]propanamide,
- 3-{[4-(2-hydroxyethyl)-1H-1,3-benzodiazol-2-yl]amino}-N-methyl-3-[3-(trifluoromethyl)phenyl]propanamide,
- Methyl 2-[(4-acetamido-1H-1,3-benzodiazol-2-yl)amino]-3-[3-(trifluoromethyl)phenyl]propanoate,
- 2-[(1H-1,3-benzodiazol-2-yl)amino]-N-methyl-3-[3-(trifluoromethyl)phenyl]propanamide,
- 3-[(1H-1,3-benzodiazol-2-yl)amino]-3-(4-fluoro-3,5-dimethylphenyl)-N-methylpropanamide,
- 3-[(1H-1,3-benzodiazol-2-yl)amino]-3-(4-chloro-3-methylphenyl)-N-methylpropanamide,
- 3-[(1H-1,3-benzodiazol-2-yl)amino]-N-methoxy-N-methyl-3-[3-(trifluoromethyl)phenyl]propanamide,
- 3-[(1H-1,3-benzodiazol-2-yl)amino]-N-methyl-3-[3-(methylsulfanyl)phenyl]propanamide,
- 3-[(1H-1,3-benzodiazol-2-yl)amino]-N-methyl-3-[3-(trifluoromethoxy)phenyl]propanamide,
- 3-[(5-fluoro-4-methyl-1H-1,3-benzodiazol-2-yl)amino]-3-[3-(trifluoromethyl)phenyl]propanamide,
- 2-[(1H-1,3-benzodiazol-2-yl)amino]-N-(2-methylpropyl)-2-[3-(trifluoromethyl)phenyl]acetamide,
- 2-[(1H-1,3-benzodiazol-2-yl)amino]-N-cyclopropyl-2-[3-(trifluoromethyl)phenyl]acetamide,
- 3-[(5-fluoro-1H-1,3-benzodiazol-2-yl)amino]-N-methyl-3-[3-(trifluoromethyl)phenyl]propanamide,
- N-methyl-3-{[5-(trifluoromethoxy)-1H-1,3-benzodiazol-2-yl]amino}-3-[3-(trifluoromethyl)phenyl]propanamide,
- 3-{[4-(methoxymethyl)-1H-1,3-benzodiazol-2-yl]amino}-N-methyl-3-[3-(trifluoromethyl)phenyl]propanamide,
- 3-[(4-chloro-1H-1,3-benzodiazol-2-yl)amino]-N-methyl-3-[3-(trifluoromethyl)phenyl]propanamide,
- 3-{[4-(hydroxymethyl)-1H-1,3-benzodiazol-2-yl]amino}-N-methyl-3-{3-[(trifluoromethyl)sulfanyl]phenyl}propanamide,
- 3-[(1H-1,3-benzodiazol-2-yl)amino]-3-(3,4-dichlorophenyl)-N-methylpropanamide,
- 3-[(1H-1,3-benzodiazol-2-yl)amino]-3-(3-cyanophenyl)-N-methylpropanamide,
- Methyl 3-{1-[(1H-1,3-benzodiazol-2-yl)amino]-2-(methylcarbamoyl)ethyl}benzoate,
- 4-[(1H-1,3-benzodiazol-2-yl)amino]-N-methyl-4-[3-(trifluoromethyl)phenyl]butanamide,
- (−)-4-[(1H-1,3-benzodiazol-2-yl)amino]-N-methyl-4-[3-(trifluoromethyl)phenyl]butanamide,
- (+)-4-[(1H-1,3-benzodiazol-2-yl)amino]-N-methyl-4-[3-(trifluoromethyl)phenyl]butanamide,
- 2-[(1H-1,3-benzodiazol-2-yl)amino]-N-methyl-2-[3-(trifluoromethyl)phenyl]propanamide,
- (+)-2-[(1H-1,3-benzodiazol-2-yl)amino]-N-methyl-2-[3-(trifluoromethyl)phenyl]propanamide, and
- (−)-2-[(1H-1,3-benzodiazol-2-yl)amino]-N-methyl-2-[3-(trifluoromethyl)phenyl]propanamide, or a pharmaceutically acceptable salt thereof.

* * * * *